US008546375B2

(12) United States Patent
Bökman-Winiwarter et al.

(10) Patent No.: US 8,546,375 B2
(45) Date of Patent: Oct. 1, 2013

(54) (3-(4-(AMINOMETHYL)PHENOXY OR PHENYLTHIO)AZETIDIN-1-YL)(5-PHENYL-1,3,4-OXADIAZOL-2-YL)METHANONE COMPOUNDS

(75) Inventors: Susanne Doris Margit Bökman-Winiwarter, Mölndal (SE); Marlene Fredenwall, Mölndal (SE); Carl Anders Hogner, Mölndal (SE); Lars Anders Mikael Johansson, Mölndal (SE); Robert Andrew Judkins, Mölndal (SE); Lanna Li, Mölndal (SE); Björn Christian Ingvar Löfberg, Mölndal (SE); Sverker Von Unge, Mölndal (SE)

(73) Assignee: AstraZeneca AB, Södertalje (SE)

(*) Notice: Subject to any disclaimer, the term of this patent is extended or adjusted under 35 U.S.C. 154(b) by 0 days.

(21) Appl. No.: 13/176,554

(22) Filed: Jul. 5, 2011

(65) Prior Publication Data
US 2012/0010189 A1 Jan. 12, 2012

Related U.S. Application Data

(60) Provisional application No. 61/361,585, filed on Jul. 6, 2010.

(51) Int. Cl.
| A61K 31/4245 | (2006.01) |
| C07D 295/155 | (2006.01) |
| C07D 413/12 | (2006.01) |
| C07D 205/04 | (2006.01) |
| C07D 413/14 | (2006.01) |
| C07D 295/096 | (2006.01) |

(52) U.S. Cl.
USPC ...... 514/210.18; 548/143; 548/518; 548/952; 544/138; 544/174; 544/111; 544/367; 544/398; 544/359; 546/209; 546/208; 540/603

(58) Field of Classification Search
None
See application file for complete search history.

(56) References Cited

U.S. PATENT DOCUMENTS

| 4,212,867 | A | 7/1980 | Boesch |
| 7,723,331 | B2 | 5/2010 | Giordanetto et al. |
| 8,110,566 | B2 | 2/2012 | Johansson et al. |
| 2005/0176795 | A1 | 8/2005 | Schwink et al. |
| 2005/0222161 | A1 | 10/2005 | Moriya et al. |
| 2008/0269275 | A1 | 10/2008 | Brown et al. |
| 2008/0300232 | A1 | 12/2008 | Brickmann et al. |
| 2008/0306055 | A1 | 12/2008 | Egner et al. |
| 2009/0076064 | A1 | 3/2009 | Urbanek et al. |

FOREIGN PATENT DOCUMENTS

| EP | 1593667 | 11/2005 |
| JP | 2006176443 | 7/2006 |
| WO | WO 2004/004726 | 1/2004 |
| WO | WO 2005/066132 | 7/2005 |
| WO | WO 2005/070902 | 8/2005 |
| WO | WO 2005/090330 | 9/2005 |
| WO | WO 2006/019833 | 2/2006 |
| WO | WO 2006/044228 | 4/2006 |
| WO | WO 2006/066173 | 6/2006 |
| WO | WO 2006/068594 | 6/2006 |
| WO | WO 2006/125665 | 11/2006 |
| WO | WO 2006/130075 | 12/2006 |
| WO | WO 2006/136924 | 12/2006 |
| WO | WO 2007/011284 | 1/2007 |
| WO | WO 2007/078251 | 7/2007 |
| WO | WO 2008/011453 | 1/2008 |
| WO | WO 2008/020799 | 2/2008 |
| WO | WO 2008/068265 | 6/2008 |
| WO | WO 2008/076562 | 6/2008 |
| WO | WO 2008/131103 | 10/2008 |
| WO | WO 2009/024502 | 2/2009 |
| WO | WO 2009/052062 | 4/2009 |
| WO | WO 2009/135842 | 11/2009 |
| WO | WO 2010/125390 | 11/2010 |
| WO | WO 2010125390 A1 * | 11/2010 |

OTHER PUBLICATIONS

International Search Report and Written Opinion for PCT/GB2010/050698, dated Jul. 30, 2010.
International Search Report and Written Opinion for PCT/GB2011/051256, dated Jan. 23, 2012.
Johansson, "Recent progress in the discovery of melanin-concentrating hormone 1-receptor anatagonists," Expert Opinion in Therapeutic Patents, 21(6): 905-925 (2011).
Mendez-Andino et al., "MCH-R1 antagonists: what is keeping most research programs away from the clinic?," Drug Discovery Today, 12(21/22):972-979 (2007).
Sheng et al., "Design, synthesis and evaluation of 2-phenoxy-indan-1-one derivatives as acetylcholinesterase inhibitors," Bioorganic & Medicinal Chemistry Letters, 15(17):3834-3837 (2005).
Wuitschik et al., "Spirocyclic Oxetanes: synthesis and properties", Angew. Chem. Int. Ed. 47: 4512-4515 (2008).

\* cited by examiner

Primary Examiner — Yong Chu
(74) Attorney, Agent, or Firm — Morgan, Lewis & Bockius LLP

(57) ABSTRACT

Disclosed herein are azetidinyl compounds of formula I,

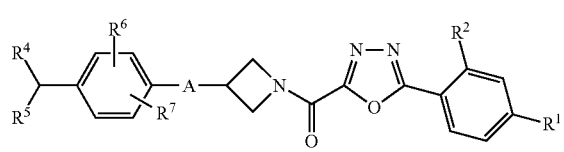

as described herein, pharmaceutical compositions comprising an azetidinyl compound, and a method of using an azetidinyl compound in the treatment or prophylaxis of a melanin-concentrating hormone related disease or condition.

12 Claims, No Drawings

(3-(4-(AMINOMETHYL)PHENOXY OR PHENYLTHIO)AZETIDIN-1-YL)(5-PHENYL-1,3,4-OXADIAZOL-2-YL)METHANONE COMPOUNDS

This application claims the benefit under 35 U.S.C. §119 (e) of Application No. 61/361,585 (US) filed on 6 Jul. 2010, which is herein incorporated by reference in its entirety.

FIELD OF INVENTION

The present invention relates to certain substituted (3-(4-(aminomethyl)phenoxy or phenylthio)azetidin-1-yl)(5-phenyl-1,3,4-oxadiazol-2-yl)methanone compounds of formula I, to processes for preparing such compounds, to their use in the treatment of a melanin-concentrating hormone related disease or condition for example obesity, obesity-related conditions, anxiety and depression, and to pharmaceutical compositions containing them.

BACKGROUND OF THE INVENTION

The actions of melanin-concentrating hormone (MCH) are thought to be involved in anxiety, depression, obesity, and obesity-related disorders. MCH has been found to be a major regulator of eating behaviour and energy homeostasis and is the natural ligand for is the 353-amino acid orphan G-protein-coupled-receptor (GPCR) termed SLC-1 (also known as GPR24). SLC-1 is sequentially homologous to the somatostatin receptors, and is frequently referred to as the "melanin-concentrating hormone receptor" (MCH receptor type 1, MCH1 receptor, or MCHR1).

In mice lacking the MCH1 receptor, there is no increased feeding response to MCH, and a lean phenotype is seen, suggesting that this receptor is responsible for mediating the feeding effect of MCH. MCH receptor antagonists have also been shown to block the feeding effects of MCH, and to reduce body weight & adiposity in diet-induced obese mice. The conservation of distribution and sequence of MCH1 receptors suggest a similar role for this receptor in man and rodent species. Hence, MCH receptor antagonists have been proposed as a treatment for obesity and other disorders characterised by excessive eating and body weight.

Emerging evidence also suggests that MCHR1 plays a role in the regulation of mood and stress. Within the central nervous system, MCHR1 mRNA and protein are distributed in various hypothalamic nuclei including, for example, the paraventricular nucleus (PVN) and the nucleus accumbens shell; and limbic structures including, for example, the hippocampus, septum, amygdala, locus coeruleus and dorsal raphe nucleus, all of which are thought to be involved in the regulation of emotion and stress.

Introduction of MCH into the medial preoptic area has been reported to induce anxiety, although contrary anxiolytic-like effects of MCH injection have also been reported. Injection of MCH into the nucleus accumbens shell, in which MCHR1 is abundant, decreased mobility in a forced swim test in rats, suggesting a depressive effect. Also, it has been reported that MCHR1 antagonists exhibited antidepressant and anxiolytic-like effects in rodent tests, suggesting a role for MCHR1 in depression and anxiety.

MCH antagonists are thus thought likely to provide benefit to numerous people and to have a potential to alleviate anxiety and depression and be useful for treating obesity and to obesity-related conditions.

MCH receptor antagonists having a bicyclic central core are disclosed in WO2006/066173 (benzothiazole or benzoxazole central core) and US2005/0222161 (benzimidazole core).

Our co-pending application WO 2010/0125390 discloses a compound of formula I

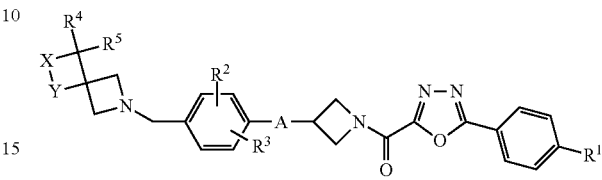

or a pharmaceutically acceptable salt thereof in which
$R^1$ represents H, fluoro, chloro, bromo, cyano, a $C_{1-3}$alkyl group optionally substituted by one or more fluoro, or a $C_{1-2}$alkoxy group optionally substituted by one or more fluoro;
A represents O or S;
$R^2$ and $R^3$ independently represent H, fluoro, chloro, bromo, a $C_{1-4}$alkyl group optionally substituted by one or more fluoro, or a $C_{1-4}$alkoxy group optionally substituted by one or more fluoro; provided that $R^2$ and $R^3$ are not located meta to each other;
$R^4$ and $R^5$ independently represent H or a $C_{1-4}$alkyl group; and
X and Y independently represent O or $CH_2$ with the proviso that X and Y are different; and the use of such compounds in the treatment of a melanin-concentrating hormone related disease or condition for example obesity, obesity-related conditions, anxiety and depression.

SUMMARY OF THE INVENTION

The present invention provides compounds that are MCH receptor antagonists and therefore are likely to be useful in the treatment of anxiety, depression, obesity and obesity-related conditions.

DESCRIPTION OF THE INVENTION

The present invention provides a compound of formula I

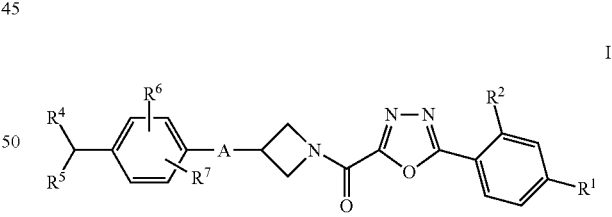

or a pharmaceutically acceptable salt thereof in which
$R^1$ represents H, fluoro, chloro, bromo, cyano, a $C_{1-4}$alkyl group optionally substituted by one or more fluoro, a $C_{1-2}$alkoxy group optionally substituted by one or more fluoro, or a $C_{1-3}$alkylthio group optionally substituted by one or more fluoro;
$R^2$ represents H or fluoro;
$R^4$ represents a group of formula —$NR^aR^b$ in which
a) $R^a$ and $R^b$ independently represent: 1) H 2) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy, a $C_{1-4}$alkoxy group or fluoro 3) a $C_{3-6}$cycloalkyl group optionally substituted by one or more of the following: hydroxy, a $C_{1-4}$alkoxy group or fluoro 4) a $C_{1-4}$alkoxy $C_{2-4}$alkylene group in which the alkylene chain is optionally substituted by one or more $C_{1-4}$alkyl groups or 5) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_{1-4}$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group; or b) $R^a$ and $R^b$ together with the nitrogen atom to which they are attached represent a saturated 4 to 7 membered monocyclic heterocyclic ring optionally containing an additional oxygen, sulphur, SO or $SO_2$ provided that this additional atom or group is always separated from the nitrogen atom by at least two carbon atoms and wherein the ring is optionally substituted by one or more of the following: fluoro, hydroxy, a $C_{1-4}$alkoxy group, a $C_{1-4}$alkoxycarbonyl group, a $C_{3-6}$cycloalkyl group, or a $C_{1-4}$alkyl group optionally substituted by hydroxy or by a $C_{1-4}$alkoxy group or by one or more fluoro, provided that the substituents linked to the ring by a hetero atom are not located at a carbon atom adjacent to any ring hetero atom; or c) $R^a$ and $R^b$ together with the nitrogen atom to which they are attached represent a saturated 4 to 7 membered monocyclic heterocyclic ring containing an additional nitrogen optionally substituted at the additional nitrogen atom by a $C_{1-4}$alkanoyl group, benzoyl, a $C_{1-4}$alkoxycarbonyl group, a $C_{1-4}$alkylsulfonyl group; carbamoyl, N—$C_{1-4}$alkylcarbamoyl, N,N-di$C_{1-4}$alkylcarbamoyl or $C_{1-4}$alkyl group;

$R^5$ represents H or a $C_{1-3}$alkyl group optionally substituted by one or more fluoro or one of the following: hydroxy or a $C_{1-4}$alkoxy group;

$R^6$ and $R^7$ independently represent H, fluoro, chloro, bromo, a $C_{1-4}$alkyl group optionally substituted by one or more fluoro, a $C_{1-4}$alkoxy group optionally substituted by one or more fluoro; provided that $R^6$ and $R^7$ are not located meta to each other; and A represents O or S.

It will be understood that the hydrogen attached to the carbon atom bearing $R^4$ and $R^5$ has been omitted from formula I for clarity. It will also be understood that the term "a saturated 4 to 7 membered monocyclic heterocyclic ring" excludes spirocyclic compounds.

In a particular group of compounds of formula I, A represents O.

In a particular group of compounds of formula I, A represents S.

In a particular group of compounds of formula I, $R^4$ represents a group of formula —$NR^aR^b$ in which $R^a$ and $R^b$ together with the nitrogen atom to which they are attached represent a saturated 4 to 6 membered monocyclic heterocyclic ring optionally containing an additional oxygen, sulphur, SO or $SO_2$ provided that this additional atom or group is always separated from the nitrogen atom by at least two carbon atoms and wherein the ring is optionally substituted by one or more of the following: fluoro, hydroxy, a $C_{1-4}$alkoxy group, a $C_{3-6}$cycloalkyl group, or a $C_{1-4}$alkyl group optionally substituted by hydroxy or by a $C_{1-4}$alkoxy group or by one or more fluoro, provided that the substituents linked to the ring by a hetero atom are not located at a carbon atom adjacent to any ring hetero atom. In a particular group of compounds of formula I, $R^4$ represents a group of formula —$NR^aR^b$ in which $R^a$ represents H and $R^b$ represents: 1) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy, a $C_{1-4}$alkoxy group or fluoro 2) a $C_{3-6}$cycloalkyl group optionally substituted by one or more of the following: hydroxy, a $C_{1-4}$alkoxy group or fluoro 3) a $C_{1-4}$alkoxy $C_{2-4}$alkylene group in which the alkylene chain is optionally substituted by one or more $C_{1-4}$alkyl groups or 4) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_{1-4}$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group.

In another aspect the present invention provides a compound of formula I represented by formula II

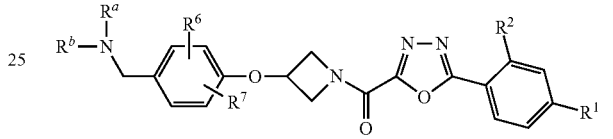

or a pharmaceutically acceptable salt thereof in which $R^1$ represents H, fluoro, chloro, bromo, a $C_{1-4}$alkyl group optionally substituted by one or more fluoro or a $C_{1-2}$alkoxy group optionally substituted by one or more fluoro;

$R^2$ represents H or fluoro;

$R^a$ and $R^b$ independently represent a) $R^a$ and $R^b$ independently represent: 1) H 2) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy or by a $C_{1-4}$alkoxy group or by one or more fluoro 3) a $C_{3-6}$cycloalkyl group optionally substituted by one or more of the following: hydroxy, a $C_{1-4}$alkoxy group or fluoro 4) a $C_{1-4}$alkoxy $C_{2-4}$alkylene group in which the alkylene chain is optionally substituted by one or more $C_{1-4}$alkyl groups or 5) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_{1-4}$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group; or b) $R^a$ and $R^b$ together with the nitrogen atom to which they are attached represent 1) a pyrrolidino ring optionally substituted by one or more of the following: fluoro, a $C_{1-4}$alkoxy group, hydroxy, or a $C_{1-4}$alkyl group optionally substituted by hydroxy, provided that the substituents linked to the ring by a hetero atom are not located at a carbon atom adjacent to the nitrogen atom; or 2) a morpholino ring; or 3) a piperazino ring which is optionally substituted at the additional nitrogen atom by a $C_{1-4}$alkanoyl group; a $C_{1-4}$alkylsulfonyl group or a $C_{1-4}$alkyl group; or 4) an azetidino ring optionally substituted by one or more of the following: fluoro, hydroxy, a $C_{1-4}$alkoxy group, a $C_{3-6}$cycloalkyl group or a $C_{1-4}$alkyl group optionally substituted by hydroxy, by a $C_{1-4}$alkoxy group or by one or more fluoro provided that the substituents linked to the ring by a hetero atom are not located at a carbon atom adjacent to any ring hetero atom; or
5) a piperidino ring optionally substituted by one or more of the following: fluoro, hydroxy, a $C_{1-4}$alkoxy group, a $C_{3-6}$cycloalkyl group, and a $C_{1-4}$alkyl group optionally substituted by hydroxy, by a $C_{1-4}$alkoxy group or by one or more fluoro; $R^6$ and $R^7$ independently represent H, fluoro, chloro, a $C_{1-4}$alkyl group or a $C_{1-4}$alkoxy group provided that $R^6$ and $R^7$ are not located meta to each other.

In another aspect the present invention provides a compound of formula I represented by formula IIA

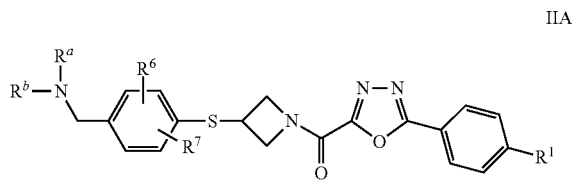

IIA or a pharmaceutically acceptable salt thereof in which
$R^1$ represents H, fluoro, chloro, bromo, a $C_{1-4}$alkyl group optionally substituted by one or more fluoro or a $C_{1-2}$alkoxy group optionally substituted by one or more fluoro;
$R^a$ and $R^b$ independently represent
a) H, a $C_{1-4}$alkyl group, a $C_{3-6}$cycloalkyl group, a $C_{1-4}$alkoxy $C_{2-4}$alkylene group in which the alkylene chain is optionally substituted by one or more $C_{1-4}$alkyl groups or $R^a$ and $R^b$ independently represent a group -L-$R^8$ in which L represents a bond or a $C_{1-4}$alkylene chain optionally substituted by one or more $C_{1-2}$alkyl groups and $R^8$ represents tetrahydrofuryl or tetrahydropyranyl each of which is optionally substituted by one or more of the following: hydroxy, a $C_{1-4}$alkyl group, a $C_{1-4}$alkoxy group or a $C_{1-4}$alkanoyl group; or
b) $R^a$ and $R^b$ together with the nitrogen atom to which they are attached represent
1) a pyrrolidino ring optionally substituted by one or more of the following: a $C_{1-4}$alkoxy group, hydroxy, or a $C_{1-4}$alkyl group optionally substituted by hydroxy provided that the substituents linked to the ring by a hetero atom are not located at a carbon atom adjacent to the nitrogen atom,
2) a morpholino ring or
3) a piperazino ring which is optionally substituted at the additional nitrogen atom by a $C_{1-4}$alkanoyl group; a $C_{1-4}$alkylsulfonyl group or a $C_{1-4}$alkyl group; or
4) an azetidino ring which is optionally substituted by one or more of the following: hydroxy, a $C_{1-4}$alkoxy group, a $C_{3-6}$cycloalkyl group, or a $C_{1-4}$alkyl group optionally substituted by hydroxy or by a $C_{1-4}$alkoxy group provided that the substituents linked to the ring by a hetero atom are not located at a carbon atom adjacent to any ring hetero atom; or
5) a piperidino ring optionally substituted by one or more of the following: fluoro, hydroxy, a $C_{1-4}$alkoxy group, a $C_{3-6}$cycloalkyl group, or a $C_{1-4}$alkyl group optionally substituted by hydroxy or by a $C_{1-4}$alkoxy group or by one or more fluoro;
$R^6$ and $R^7$ independently represent H, fluoro, chloro, a $C_{1-4}$alkyl group or a $C_{1-4}$alkoxy group provided that $R^6$ and $R^7$ are not located meta to each other.
$R^6$ and $R^7$ independently represent H, chloro, fluoro, a $C_{1-4}$alkyl group or a $C_{1-4}$alkoxy group provided that $R^6$ and $R^7$ are not located meta to each other.

In a further embodiment the present invention provides a compound of formula III

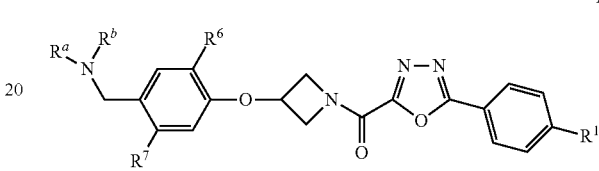

III or a pharmaceutically acceptable salt thereof
in which $R^1$ represents H or methoxy;
$R^a$ and $R^b$ independently represent H or methyl provided that at least one of $R^a$ and $R^b$ represents methyl; and
$R^6$ and $R^7$ independently represent H or methyl provided that at least one of $R^6$ and $R^7$ represents methyl.

In a further embodiment the present invention provides a compound of formula IIIA

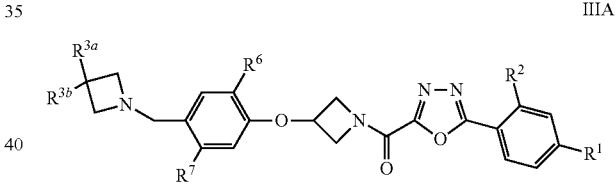

IIIA or a pharmaceutically acceptable salt thereof
in which $R^1$ represents H or methoxy;
in which $R^2$ represents H or fluoro;
$R^6$ and $R^7$ independently represent H, chloro or methyl provided that one of $R^6$ and $R^7$ represents H;
$R^{3a}$ represents H, fluoro, hydroxy or a $C_{1-4}$alkyl group optionally substituted by hydroxy or by one or more fluoro; and
$R^{3b}$ represents H or a $C_{1-4}$alkyl group optionally substituted by hydroxy.

In a further embodiment the present invention provides a compound of formula IIIB

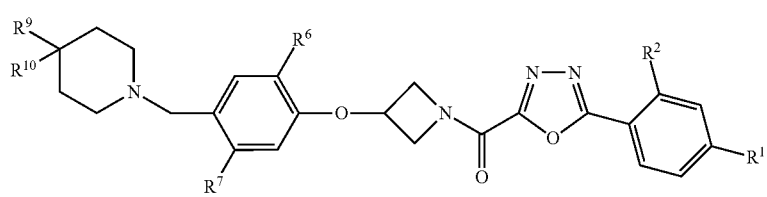

IIIB or a pharmaceutically acceptable salt thereof
in which R¹ represents H or methoxy;
R² represents H or fluoro;
R⁶ and R⁷ independently represent H or methyl provided that only one of R⁶ and R⁷ represents methyl;
R⁹ represents H, fluoro, hydroxy or a $C_{1-4}$alkyl group optionally substituted by hydroxy or by one or more fluoro; and
R¹⁰ represents H or a $C_{1-4}$alkyl group optionally substituted by hydroxy.

In a further embodiment the present invention provides a compound of formula IIIC

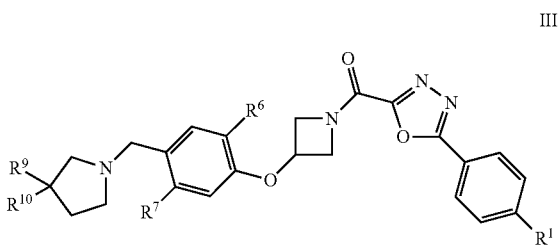

IIIC or a pharmaceutically acceptable salt thereof
in which R¹ represents H or methoxy;
R⁶ and R⁷ independently represent H or methyl provided that only one of R⁶ and R⁷ represents methyl;
R⁹ represents H, fluoro, hydroxy or a $C_{1-4}$alkyl group optionally substituted by hydroxy or by one or more fluoro; and
R¹⁰ represents H or a $C_{1-4}$alkyl group optionally substituted by hydroxy.

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I) (including formulae II, IIA, III, IIIA, IIIB and IIIC). Further, each of the following values may be used in combination with one or more of the other following values to limit the broadest definition, or any sub-definition, of formula (I) (including formulae II, IIA, III, IIIA, IIIB and IIIC).

1) R¹ represents H, chloro, fluoro, methoxy, methyl, cyano, trifluoromethyl, difluoromethoxy, trifluoromethoxy or methylthio.
2) R¹ represents H or methoxy.
3) R² represents H.
4) R⁴ represents azetidino optionally substituted as previously described.
5) R⁴ represents pyrrolidino optionally substituted as previously described.
6) R⁴ represents piperidino optionally substituted as previously described.
7) R⁴ represents morpholino optionally substituted as previously described.
8) R⁴ represents piperazino optionally substituted as previously described.
9) R⁴ represents a di($C_{1-4}$alkylamino) group.
10) R⁴ represents a mono($C_{1-4}$alkyl)amino group.
11) R⁴ represents pyrrolidino, morpholino, 4-methylpiperazin-1-yl, 3-methoxypyrrolidino, 3-hydroxypyrrolidino, 4-acetylpiperazin-1-yl, 4-methylsulfonylpiperazin-1-yl, dimethylamino, methylamino, 3-methoxyazetidin-1-yl, 3-hydroxymethylazetidin-1-yl, 3-cyclopropyl-3-hydroxyazetidin-1-yl, 3-hydroxyazetidin-1-yl, 2-methoxyethyl)(methyl)amino, methyl(tetrahydro-2H-pyran-4-yl)amino, methyl((tetrahydrofuran-3-yl)methyl)amino, cyclopropylamino, 3-(difluoromethyl)-azetidin-1-yl, 4-(hydroxymethyl)-4-methylpiperidin-1-yl, 3-ethyl-3-hydroxyazetidin-1-yl, 3-hydroxy-3-methylazetidin-1-yl; 4-fluoro-4-(hydroxymethyl)piperidin-1-yl, 3-(hydroxymethyl)-3-methylpyrrolidin-1-yl, 4-hydroxyazepan-1-yl, 4-hydroxy-4-methylazepan-1-yl or 4-(hydroxymethyl)piperidin-1-yl.

12) R⁴ represents pyrrolidino, morpholino, 4-methylpiperazin-1-yl, 3-methoxypyrrolidino, 3-hydroxypyrrolidino, 4-acetylpiperazin-1-yl, 4-methylsulfonylpiperazin-1-yl, dimethylamino, methylamino, 3-methoxyazetidin-1-yl, 3-hydroxymethylazetidin-1-yl, 3-cyclopropyl-3-hydroxyazetidin-1-yl, 3-methoxyazetidin-1-yl), 3-hydroxyazetidin-1-yl, 2-methoxyethyl)(methyl)amino, methyl(tetrahydro-2H-pyran-4-yl)amino, methyl((tetrahydrofuran-3-yl)methyl)amino, cyclopropylamino, 3-(difluoromethyl)azetidin-1-yl, 4-(hydroxymethyl)-4-methylpiperidin-1-yl, 3-ethyl-3-hydroxyazetidin-1-yl, 3-hydroxy-3-methylazetidin-1-yl; 4-fluoro-4-(hydroxymethyl)piperidin-1-yl or 4-(hydroxymethyl)-4-methylpiperidin-1-yl.

13) R⁴ represents pyrrolidino, morpholino, 4-methylpiperazin-1-yl 3-methoxypyrrolidino, 3-hydroxypyrrolidino, 4-acetylpiperazin-1-yl, 4-methylsulfonylpiperazin-1-yl or 4-dimethylamino.

14) R⁴ represents pyrrolidino, morpholino, 4-methylpiperazin-1-yl, 4-acetylpiperazin-1-yl or 4-dimethylamino.

15) R⁴ represents dimethylamino.
16) R⁴ represents 3-(difluoromethyl)azetidin-1-yl or 3-hydroxy-3-methylazetidin-1-yl.
17) R⁴ represents 4-(hydroxymethyl)-4-methylpiperidin-1-yl.
18) R⁵ represents H or methyl.
19) R⁵ represents H.
20) R⁶ and R⁷ independently represent H, fluoro, chloro, a $C_{1-4}$alkyl group optionally substituted by one or more fluoro or a $C_{1-4}$alkoxy group.
21) R⁶ and R⁷ independently represent H, fluoro, chloro, methyl, methoxy or trifluoromethyl.
22) R⁶ and R⁷ independently represent H, fluoro, methyl or methoxy.
23) A is O.
24) A is S.
25) R¹ represents H, fluoro, chloro, bromo, a $C_{1-4}$alkyl group optionally substituted by one or more fluoro or a $C_{1-4}$alkoxy group optionally substituted by one or more fluoro.
26) R⁴ represents a group of formula —NR$^a$R$^b$ in which R$^a$ and R$^b$ independently represent
a) H, a $C_{1-4}$alkyl group, a $C_{3-6}$cycloalkyl group, a $C_{1-4}$alkoxy $C_{2-4}$alkylene group in which the alkylene chain is optionally substituted by one or more $C_{1-4}$alkyl groups or R$^a$ represents H, a $C_{1-4}$alkyl group or a $C_{3-6}$cycloalkyl group and R$^b$ independently represent a group -L-R⁸ in which L represents a bond or a $C_{1-4}$alkylene chain optionally substituted by one or more $C_{1-2}$alkyl groups and R⁸ represents tetrahydrofuryl or tetrahydropyranyl each of which is optionally substituted by one or more of the following: hydroxy, a $C_{1-4}$alkyl group, a $C_{1-4}$alkoxy group or a $C_{1-4}$alkanoyl group; or
b) R$^a$ and R$^b$ together with the nitrogen atom to which they are attached represent
1) a pyrrolidino ring optionally substituted by one or more of the following: a $C_{1-4}$alkoxy group, hydroxy, or a $C_{1-4}$alkyl group provided that the substituents linked to the ring by a hetero atom are not located at a carbon atom adjacent to the nitrogen atom, 2) a morpholino ring or
3) a piperazino ring which is optionally substituted at the additional nitrogen atom by a $C_{1-4}$alkanoyl group; a $C_{1-4}$alkylsulfonyl group or a $C_{1-4}$alkyl group; and
4) an azetidino ring which is optionally substituted hydroxy, a $C_{1-4}$alkyl group, a $C_{1-4}$alkoxy group, a $C_{3-6}$cycloalkyl group, or a $C_{1-4}$alkyl group optionally substituted by hydroxy or by a $C_{1-4}$alkoxy group provided that the substituents linked to the ring by a hetero atom are not located at a carbon atom adjacent to any ring hetero atom.
27) $R^4$ represents a group of formula —$NR^aR^b$ in which $R^a$ represents H and $R^b$ represents
a) H, a $C_{1-4}$alkyl group, a $C_{3-6}$cycloalkyl group, a $C_{1-4}$alkoxy $C_{2-4}$alkylene group in which the alkylene chain is optionally substituted by one or more $C_{1-4}$alkyl groups or $R^a$ represents H, a $C_{1-4}$alkyl group or a $C_{3-6}$cycloalkyl group and $R^b$ independently represent a group -L-$R^8$ in which L represents a bond or a $C_{1-4}$alkylene chain optionally substituted by one or more $C_{1-2}$alkyl groups and $R^8$ represents tetrahydrofuryl or tetrahydropyranyl each of which is optionally substituted by one or more of the following: hydroxy, a $C_{1-4}$alkyl group, a $C_{1-4}$alkoxy group or a $C_{1-4}$alkanoyl group; or
b) $R^a$ and $R^b$ together with the nitrogen atom to which they are attached represent
1) a pyrrolidino ring optionally substituted by one or more of the following: a $C_{1-4}$alkoxy group, hydroxy, or a $C_{1-4}$alkyl group provided that the substituents linked to the ring by a hetero atom are not located at a carbon atom adjacent to the nitrogen atom,
2) a morpholino ring or
3) a piperazino ring which is optionally substituted at the additional nitrogen atom by a $C_{1-4}$alkanoyl group; a $C_{1-4}$alkylsulfonyl group or a $C_{1-4}$alkyl group; and
4) an azetidino ring which is optionally substituted hydroxy, a $C_{1-4}$alkyl group, a $C_{1-4}$alkoxy group, a $C_{3-6}$cycloalkyl group, or a $C_{1-4}$alkyl group optionally substituted by hydroxy or by a $C_{1-4}$alkoxy group provided that the substituents linked to the ring by a hetero atom are not located at a carbon atom adjacent to any ring hetero atom.
28) $R^4$ represents a group of formula —$NR^aR^b$ in which $R^a$ and $R^b$ together with the nitrogen atom to which they are attached represent a pyrrolidino ring optionally substituted by one or more of the following: fluoro, a $C_{1-4}$alkoxy group, hydroxy, a $C_{1-4}$alkyl group or a hydroxy$C_{1-4}$alkyl group provided that the substituents linked to the ring by a hetero atom are not located at a carbon atom adjacent to the nitrogen atom.
29) $R^4$ represents a group of formula —$NR^aR^b$ in which $R^a$ and $R^b$ together with the nitrogen atom to which they are attached represent a pyrrolidino ring optionally substituted by one or more of the following: methoxy, hydroxy, methyl or a hydroxymethyl group provided that the substituents linked to the ring by a hetero atom are not located at a carbon atom adjacent to the nitrogen atom.
30) $R^4$ represents a group of formula —$NR^aR^b$ in which $R^a$ and $R^b$ together with the nitrogen atom to which they are attached represent a piperidino ring optionally substituted by one or more of the following: fluoro, a $C_{1-4}$alkoxy group, hydroxy, a $C_{1-4}$alkyl group or a hydroxy$C_{1-4}$alkyl group provided that the substituents linked to the ring by a hetero atom are not located at a carbon atom adjacent to the nitrogen atom.
31) $R^4$ represents a group of formula —$NR^aR^b$ in which $R^a$ and $R^b$ together with the nitrogen atom to which they are attached represent a piperidino ring optionally substituted by one or more of the following: methoxy, hydroxy, methyl or a hydroxymethyl group provided that the substituents linked to the ring by a hetero atom are not located at a carbon atom adjacent to the nitrogen atom.
32) $R^4$ represents a group of formula —$NR^aR^b$ in which $R^a$ and $R^b$ together with the nitrogen atom to which they are attached represent an azepano ring optionally substituted by one or more of the following: fluoro, a $C_{1-4}$alkoxy group, hydroxy, a $C_{1-4}$alkyl group or a hydroxy$C_{1-4}$alkyl group provided that the substituents linked to the ring by a hetero atom are not located at a carbon atom adjacent to the nitrogen atom.
33) $R^4$ represents a group of formula —$NR^aR^b$ in which $R^a$ and $R^b$ together with the nitrogen atom to which they are attached represent an azepano ring optionally substituted by one or more of the following: methoxy, hydroxy, methyl or a hydroxymethyl group provided that the substituents linked to the ring by a hetero atom are not located at a carbon atom adjacent to the nitrogen atom.

The term "a saturated 4 to 7 membered monocyclic heterocyclic ring optionally containing an additional oxygen, sulphur, SO or $SO_2$" includes azetidinyl, pyrrolidyl, morpholinyl, perhydroazepinyl, perhydrooxazepinyl, piperidinyl, or homopiperidinyl each of which may be optionally substituted as previously described. The term "a saturated 4 to 7 membered monocyclic heterocyclic ring containing an additional nitrogen" includes piperazinyl, homopiperazinyl or imidazolidinyl each of which is optionally substituted as previously described.

The term "a carbon linked 4-7 membered saturated monocyclic heterocyclic ring containing 1 or 2 hetero atoms selected from oxygen and nitrogen" includes oxetanyl, tetrahydrofuryl, tetrahydropyranyl, 1,4-dioxanyl, azetidinyl, pyrrolidyl, morpholinyl, perhydroazepinyl, perhydrooxazepinyl, piperidinyl or homopiperidinyl. Each of these rings is optionally substituted as previously described.

The terms "$C_{1-4}$alkyl" refers to a straight or branched chain alkane radical containing from 1 to 4 carbon atoms. Exemplary groups include methyl; ethyl; propyl; isopropyl; 1-methylpropyl; n-butyl, t-butyl; and isobutyl.

The term "$C_{1-4}$ alkoxy" refers to groups of the general formula —$OR^a$, wherein $R^a$ is selected from a $C_{1-4}$alkyl. Exemplary alkoxys include, but are not limited to methoxy, ethoxy, propoxy, isopropoxy, butoxy, t-butoxy or isobutoxy. In a further aspect the present invention provides one or more of the following compounds:
(5-(4-chlorophenyl)-1,3,4-oxadiazol-2-yl)(3-(4-(pyrrolidin-1-ylmethyl)phenoxy)azetidin-1-yl)methanone;
(5-(4-methoxyphenyl)-1,3,4-oxadiazol-2-yl)(3-(4-(pyrrolidin-1-ylmethyl)phenoxy)azetidin-1-yl)methanone;
(5-phenyl-1,3,4-oxadiazol-2-yl)(3-(4-(pyrrolidin-1-ylmethyl)phenoxy)azetidin-1-yl)methanone;
(5-(4-fluorophenyl)-1,3,4-oxadiazol-2-yl)(3-(4-(pyrrolidin-1-ylmethyl)phenoxy)azetidin-1-yl)methanone;
(3-(4-(pyrrolidin-1-ylmethyl)phenoxy)azetidin-1-yl)(5-(4-(trifluoromethyl)phenyl)-1,3,4-oxadiazol-2-yl)methanone;
(3-(4-(pyrrolidin-1-ylmethyl)phenoxy)azetidin-1-yl)(5-p-tolyl-1,3,4-oxadiazol-2-yl)methanone;
(3-(3-methoxy-4-(morpholinomethyl)phenoxy)azetidin-1-yl)(5-phenyl-1,3,4-oxadiazol-2-yl)methanone;
(3-(3-methoxy-4-(morpholinomethyl)phenoxy)azetidin-1-yl)(5-(4-methoxyphenyl)-1,3,4-oxadiazol-2-yl)methanone;
(3-(2-methyl-4-((4-methylpiperazin-1-yl)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(2-methyl-4-((4-methylpiperazin-1-yl)methyl)phenoxy)azetidin-1-yl)methanone;
(3-(2-methyl-4-((4-methylpiperazin-1-yl)methyl)phenoxy)azetidin-1-yl)(5-p-tolyl-1,3,4-oxadiazol-2-yl)methanone;

(5-(4-methoxyphenyl)-1,3,4-oxadiazol-2-yl)(3-(2-methyl-4-(morpholinomethyl)phenoxy)-azetidin-1-yl)methanone;
(3-(2-methyl-4-(morpholinomethyl)phenoxy)azetidin-1-yl)(5-p-tolyl-1,3,4-oxadiazol-2-yl)methanone;
(3-(2-methyl-4-(morpholinomethyl)phenoxy)azetidin-1-yl)(5-phenyl-1,3,4-oxadiazol-2-yl)methanone;
(5-(4-chlorophenyl)-1,3,4-oxadiazol-2-yl)(3-(2-methyl-4-(morpholinomethyl)phenoxy)-azetidin-1-yl)methanone;
(3-(4-((dimethylamino)methyl)-2-methylphenoxy)azetidin-1-yl)(5-phenyl-1,3,4-oxadiazol-2-yl)methanone;
(3-(4-((dimethylamino)methyl)-2-methylphenoxy)azetidin-1-yl)(5-(4-methoxyphenyl)-1,3,4-oxadiazol-2-yl)methanone;
(3-(4-((dimethylamino)methyl)-2-methylphenoxy)azetidin-1-yl)(5-p-tolyl-1,3,4-oxadiazol-2-yl)methanone;
(5-(4-chlorophenyl)-1,3,4-oxadiazol-2-yl)(3-(2-methyl-4-(pyrrolidin-1-ylmethyl)phenoxy)-azetidin-1-yl)methanone;
(3-(4-((dimethylamino)methyl)-3-methylphenoxy)azetidin-1-yl)(5-(4-methoxyphenyl)-1,3,4-oxadiazol-2-yl)methanone;
(3-(4-((dimethylamino)methyl)-3-methylphenoxy)azetidin-1-yl)(5-phenyl-1,3,4-oxadiazol-2-yl)methanone;
(3-(4-((dimethylamino)methyl)-3-methylphenoxy)azetidin-1-yl)(5-p-tolyl-1,3,4-oxadiazol-2-yl)methanone;
1-(4-(4-(1-(5-phenyl-1,3,4-oxadiazole-2-carbonyl)azetidin-3-yloxy)benzyl)piperazin-1-yl)ethanone;
1-(4-(4-(1-(5-(4-methoxyphenyl)-1,3,4-oxadiazole-2-carbonyl)azetidin-3-yloxy)benzyl)piperazin-1-yl)ethanone;
1-(4-(4-(1-(5-(4-chlorophenyl)-1,3,4-oxadiazole-2-carbonyl)azetidin-3-yloxy)benzyl)piperazin-1-yl)ethanone;
(3-(4-((dimethylamino)methyl)-3-fluorophenoxy)azetidin-1-yl)(5-phenyl-1,3,4-oxadiazol-2-yl)methanone;
(3-(4-((dimethylamino)methyl)-3-fluorophenoxy)azetidin-1-yl)(5-(4-methoxyphenyl)-1,3,4-oxadiazol-2-yl)methanone;
(3-(4-((dimethylamino)methyl)-3-fluorophenoxy)azetidin-1-yl)(5-p-tolyl-1,3,4-oxadiazol-2-yl)methanone;
(3-(3-fluoro-4-((4-methylpiperazin-1-yl)methyl)phenoxy)azetidin-1-yl)(5-phenyl-1,3,4-oxadiazol-2-yl)methanone;
(3-(3-fluoro-4-((4-methylpiperazin-1-yl)methyl)phenoxy)azetidin-1-yl)(5-(4-iii methoxyphenyl)-1,3,4-oxadiazol-2-yl)methanone;
(3-(3-fluoro-4-(pyrrolidin-1-ylmethyl)phenoxy)azetidin-1-yl)(5-phenyl-1,3,4-oxadiazol-2-yl)methanone;
(3-(3-fluoro-4-(pyrrolidin-1-ylmethyl)phenoxy)azetidin-1-yl)(5-(4-methoxyphenyl)-1,3,4-oxadiazol-2-yl)methanone;
(3-(4-((dimethylamino)methyl)phenoxy)azetidin-1-yl)(5-phenyl-1,3,4-oxadiazol-2-yl)methanone;
(3-(4-((dimethylamino)methyl)phenoxy)azetidin-1-yl)(5-(4-(methylthio)phenyl)-1,3,4-oxadiazol-2-yl)methanone;
(3-(4-((dimethylamino)methyl)phenoxy)azetidin-1-yl)(5-(4-(trifluoromethyl)phenyl)-1,3,4-oxadiazol-2-yl)methanone;
(5-(4-chlorophenyl)-1,3,4-oxadiazol-2-yl)(3-(4-((dimethylamino)methyl)phenoxy)azetidin-1-yl)methanone;
(5-(4-(difluoromethoxy)phenyl)-1,3,4-oxadiazol-2-yl)(3-(4-((dimethylamino)methyl)-phenoxy)azetidin-1-yl)methanone;
(3-(4-((dimethylamino)methyl)phenoxy)azetidin-1-yl)(5-(4-methoxyphenyl)-1,3,4-oxadiazol-2-yl)methanone;
(3-(4-((dimethylamino)methyl)-2,3-difluorophenoxy)azetidin-1-yl)(5-phenyl-1,3,4-oxadiazol-2-yl)methanone;
(3-(4-((dimethylamino)methyl)-2,3-difluorophenoxy)azetidin-1-yl)(5-(4-methoxyphenyl)-1,3,4-oxadiazol-2-yl)methanone;
(3-(4-(azetidin-1-ylmethyl)phenoxy)azetidin-1-yl)(5-(4-methoxyphenyl)-1,3,4-oxadiazol-2-yl)methanone;
(3-(4-(azetidin-1-ylmethyl)phenoxy)azetidin-1-yl)(5-phenyl-1,3,4-oxadiazol-2-yl)methanone;
(5-(4-(difluoromethoxy)phenyl)-1,3,4-oxadiazol-2-yl)(3-(4-((dimethylamino)methyl)-3-methylphenoxy)azetidin-1-yl)methanone;
(5-(4-chlorophenyl)-1,3,4-oxadiazol-2-yl)(3-(4-((dimethylamino)methyl)-3-methylphenoxy)azetidin-1-yl)methanone;
(5-phenyl-1,3,4-oxadiazol-2-yl)(3-(4-(pyrrolidin-1-ylmethyl)-3-(trifluoromethyl)phenoxy)azetidin-1-yl)methanone;
(5-(4-methoxyphenyl)-1,3,4-oxadiazol-2-yl)(3-(4-(pyrrolidin-1-ylmethyl)-3-(trifluoromethyl)phenoxy)azetidin-1-yl)methanone;
(3-(3-chloro-4-((dimethylamino)methyl)phenoxy)azetidin-1-yl)(5-(4-methoxyphenyl)-1,3,4-oxadiazol-2-yl)methanone;
(3-(3-chloro-4-((dimethylamino)methyl)phenoxy)azetidin-1-yl)(5-phenyl-1,3,4-oxadiazol-2-yl)methanone;
(3-(3-chloro-4-((4-methylpiperazin-1-yl)methyl)phenoxy)azetidin-1-yl)(5-(4-methoxyphenyl)-1,3,4-oxadiazol-2-yl)methanone;
(3-(3-chloro-4-((4-methylpiperazin-1-yl)methyl)phenoxy)azetidin-1-yl)(5-phenyl-1,3,4-oxadiazol-2-yl)methanone;
(5-(4-(difluoromethoxy)phenyl)-1,3,4-oxadiazol-2-yl)(3-(4-((dimethylamino)methyl)-3-fluorophenoxy)azetidin-1-yl)methanone;
(3-(3-methoxy-2-methyl-4-(pyrrolidin-1-ylmethyl)phenoxy)azetidin-1-yl)(5-(4-methoxyphenyl)-1,3,4-oxadiazol-2-yl)methanone;
(3-(3-methyl-4-((methylamino)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(2-methyl-4-((methylamino)methyl)phenoxy)azetidin-1-yl)methanone;
(3-(4-((3-methoxyazetidin-1-yl)methyl)phenoxy)azetidin-1-yl)(5-(4-methoxyphenyl)-1,3,4-oxadiazol-2-yl)methanone;
(3-(4-((3-cyclopropyl-3-hydroxyazetidin-1-yl)methyl)phenoxy)azetidin-1-yl)(5-(4-methoxyphenyl)-1,3,4-oxadiazol-2-yl)methanone;
(3-(2-chloro-4-((3-methoxyazetidin-1-yl)methyl)phenoxy)azetidin-1-yl)(5-phenyl-1,3,4-oxadiazol-2-yl)methanone;
(3-(2-chloro-4-((3-hydroxyazetidin-1-yl)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(4-(pyrrolidin-1-ylmethyl)phenylthio)azetidin-1-yl)methanone;
(3-(4-((dimethylamino)methyl)phenylthio)azetidin-1-yl)(5-phenyl-1,3,4-oxadiazol-2-yl)methanone;
(3-(4-(((2-methoxyethyl)(methyl)amino)methyl)phenylthio)azetidin-1-yl)(5-phenyl-1,3,4-oxadiazol-2-yl)methanone;
(3-(4-((3-methoxyazetidin-1-yl)methyl)phenylthio)azetidin-1-yl)(5-phenyl-1,3,4-oxadiazol-2-yl)methanone;
(3-(4-((methylamino)methyl)phenylthio)azetidin-1-yl)(5-phenyl-1,3,4-oxadiazol-2-yl)methanone;
(3-(4-((methyl(tetrahydro-2H-pyran-4-yl)amino)methyl)phenylthio)azetidin-1-yl)(5-phenyl-1,3,4-oxadiazol-2-yl)methanone;
(3-(4-((methyl((tetrahydrofuran-3-yl)methyl)amino)methyl)phenylthio)azetidin-1-yl)(5-phenyl-1,3,4-oxadiazol-2-yl)methanone;
(3-(4-((cyclopropylamino)methyl)phenylthio)azetidin-1-yl)(5-phenyl-1,3,4-oxadiazol-2-yl)methanone;
(3-(4-((3-(hydroxymethyl)azetidin-1-yl)methyl)phenylthio)azetidin-1-yl)(5-phenyl-1,3,4-oxadiazol-2-yl)methanone;

(3-(4-((3-(difluoromethyl)azetidin-1-yl)methyl)phenoxy)azetidin-1-yl)(5-phenyl-1,3,4-oxadiazol-2-yl)methanone;
(3-(4-((4-(hydroxymethyl)-4-methylpiperidin-1-yl)methyl)-3-methylphenoxy)azetidin-1-yl)(5-phenyl-1,3,4-oxadiazol-2-yl)methanone;
(3-(4-((3-ethyl-3-hydroxyazetidin-1-yl)methyl)phenoxy)azetidin-1-yl)(5-(4-methoxyphenyl)-1,3,4-oxadiazol-2-yl)methanone;
(3-(4-((3-ethyl-3-hydroxyazetidin-1-yl)methyl)phenoxy)azetidin-1-yl)(5-phenyl-1,3,4-oxadiazol-2-yl)methanone;
(3-(4-((3-ethyl-3-hydroxyazetidin-1-yl)methyl)-2-methylphenoxy)azetidin-1-yl)(5-(4-methoxyphenyl)-1,3,4-oxadiazol-2-yl)methanone;
(3-(4-((3-ethyl-3-hydroxyazetidin-1-yl)methyl)-3-methylphenoxy)azetidin-1-yl)(5-(4-methoxyphenyl)-1,3,4-oxadiazol-2-yl)methanone;
(3-(4-((3-ethyl-3-hydroxyazetidin-1-yl)methyl)-2-methylphenoxy)azetidin-1-yl)(5-phenyl-1,3,4-oxadiazol-2-yl)methanone;
(3-(4-((3-ethyl-3-hydroxyazetidin-1-yl)methyl)-3-methylphenoxy)azetidin-1-yl)(5-phenyl-1,3,4-oxadiazol-2-yl)methanone;
(3-(4-((3-hydroxy-3-methylazetidin-1-yl)methyl)phenoxy)azetidin-1-yl)(5-(4-methoxyphenyl)-1,3,4-oxadiazol-2-yl)methanone;
(3-(4-((3-hydroxy-3-methylazetidin-1-yl)methyl)phenoxy)azetidin-1-yl)(5-phenyl-1,3,4-oxadiazol-2-yl)methanone;
(3-(2-chloro-4-((3-hydroxy-3-methylazetidin-1-yl)methyl)phenoxy)azetidin-1-yl)(5-phenyl-1,3,4-oxadiazol-2-yl)methanone;
(3-(2-chloro-4-((3-hydroxy-3-methylazetidin-1-yl)methyl)phenoxy)azetidin-1-yl)(5-(4-methoxyphenyl)-1,3,4-oxadiazol-2-yl)methanone;
(3-(4-((3-hydroxy-3-methylazetidin-1-yl)methyl)-3-methylphenoxy)azetidin-1-yl)(5-(4-methoxyphenyl)-1,3,4-oxadiazol-2-yl)methanone;
(3-(4-((4-fluoro-4-(hydroxymethyl)piperidin-1-yl)methyl)phenoxy)azetidin-1-yl)(5-(4-methoxyphenyl)-1,3,4-oxadiazol-2-yl)methanone;
(3-(4-((4-(hydroxymethyl)-4-methylpiperidin-1-yl)methyl)-3-methylphenoxy)azetidin-1-yl)(5-(4-methoxyphenyl)-1,3,4-oxadiazol-2-yl)methanone;
(3-(4-((4-(hydroxymethyl)-4-methylpiperidin-1-yl)methyl)phenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(+)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(−)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)phenoxy)azetidin-1-yl)(5-phenyl-1,3,4-oxadiazol-2-yl)methanone;
(+)(3-(4-((3-(hydroxymethyl)-3-methylpyrrolidin-1-yl)methyl)phenoxy)azetidin-1-yl)(5-phenyl-1,3,4-oxadiazol-2-yl)methanone;
(−)(3-(4-((3-(hydroxymethyl)-3-methylpyrrolidin-1-yl)methyl)phenoxy)azetidin-1-yl)(5-phenyl-1,3,4-oxadiazol-2-yl)methanone;
(3-(4-((4-hydroxyazepan-1-yl)methyl)phenoxy)azetidin-1-yl)(5-(4-methoxyphenyl)-1,3,4-oxadiazol-2-yl)methanone;
(+)(3-(4-((4-hydroxyazepan-1-yl)methyl)phenoxy)azetidin-1-yl)(5-(4-methoxyphenyl)-1,3,4-oxadiazol-2-yl)methanone;
(−)(3-(4-((4-hydroxyazepan-1-yl)methyl)phenoxy)azetidin-1-yl)(5-(4-methoxyphenyl)-1,3,4-oxadiazol-2-yl)methanone;
(3-(4-((4-hydroxy-4-methylazepan-1-yl)methyl)phenoxy)azetidin-1-yl)(5-phenyl-1,3,4-oxadiazol-2-yl)methanone;
(+)(3-(4-((4-hydroxy-4-methylazepan-1-yl)methyl)phenoxy)azetidin-1-yl)(5-phenyl-1,3,4-oxadiazol-2-yl)methanone;
(−)(3-(4-((4-hydroxy-4-methylazepan-1-yl)methyl)phenoxy)azetidin-1-yl)(5-phenyl-1,3,4-oxadiazol-2-yl)methanone;
(3-(4-((4-hydroxy-4-methylazepan-1-yl)methyl)phenoxy)azetidin-1-yl)(5-(4-methoxyphenyl)-1,3,4-oxadiazol-2-yl)methanone;
(+)(3-(4-((4-hydroxy-4-methylazepan-1-yl)methyl)phenoxy)azetidin-1-yl)(5-(4-methoxyphenyl)-1,3,4-oxadiazol-2-yl)methanone;
(−)(3-(4-((4-hydroxy-4-methylazepan-1-yl)methyl)phenoxy)azetidin-1-yl)(5-(4-methoxyphenyl)-1,3,4-oxadiazol-2-yl)methanone;
(3-(4-((4-(hydroxymethyl)piperidin-1-yl)methyl)phenoxy)azetidin-1-yl)(5-(4-methoxyphenyl)-1,3,4-oxadiazol-2-yl)methanone;
3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(+)(3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(−)(3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone;
(+)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone;
(−)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone; and
(3-(4-((4-ethyl-4-(hydroxymethyl)piperidin-1-yl)methyl)phenoxy)azetidin-1-yl)(5-(4-methoxyphenyl)-1,3,4-oxadiazol-2-yl)methanone;
or a pharmaceutically acceptable salt thereof.

The present invention also provides one of the compounds from the above list or any number of the above compounds between 1 and 106 for example between 1 and 92 or for example between 1 and 83. In another aspect the present invention provides a compound of formula I (including formulae II, IIA, III, IIIA, IIIB and IIIC) as defined in any of the definitions above but excluding any one or more of the compounds in the list of compounds immediately above.

From this point onward in the description a compound of formula I includes in the alternative a compound of each of the following formulae: II, HA, III, IIIA, IIIB and IIIC.

Further described herein is a pharmaceutical composition comprising a compound of formula I, or a pharmaceutically acceptable salt thereof, and a pharmaceutically acceptable carrier and/or diluent.

Yet further described herein is a method for treatment or prophylaxis of a disease or condition in which modulation of the MCH1 receptor is beneficial comprising administering to a warm-blooded animal in need of such treatment or prophylaxis a therapeutically-effective amount of a compound of formula I, or a pharmaceutically acceptable salt thereof.

Yet still further described herein is the use a compound according to formula I, or a pharmaceutically acceptable salt thereof, or mixtures thereof for the treatment or prophylaxis of a disease or condition in which modulation of the MCH1 receptor is beneficial.

Even further described herein is use of a compound according to formula I, or pharmaceutically acceptable salts thereof, or mixtures thereof in the manufacture of a medicament for the treatment or prophylaxis of a disease or condition in which modulation of the MCH1 receptor is beneficial.

Still further described herein is the use a compound of formula I, or a pharmaceutically acceptable salt thereof, as a medicament.

The term "MCHR" refers to the melanin-concentrating hormone receptor protein 1 (MCHR1), unless otherwise stated.

The terms "treat", "treating", and "treatment" refer to modulation of a disease and/or its attendant symptoms.

The terms "prevent", "preventing", and "prevention" refer to decreasing or eliminating a disease and/or its attendant symptoms.

The terms "modulate", "modulates", "modulating", or "modulation", as used herein, refer to, for example, the activation (e.g., agonist activity) or inhibition (e.g., antagonist activity) of at least one MCHR.

The term "pharmaceutically-acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The terms "prophylaxis", as used herein, refer to (i) preventing the development of a disease and/or condition; and/or (ii) protecting against worsening of a disease and/or condition in a situation where the disease and/or condition has developed.

As used herein, the term "MCHR-mediated condition or disease" refers to a condition or disease amenable to modulation by an MCHR active agent.

The term "therapeutically-effective amount" refers to that amount of a compound sufficient to modulate one or more of the symptoms of the condition or disease being treated.

A further embodiment relates to compounds as described herein wherein one or more of the atoms is an isotope of the same element for example $^{11}C$, $^{13}C$, $^{14}C$ or deuterium. In a particular embodiment, the compound is labelled with tritium. Such isotopically labelled compounds are synthesized either by incorporating labelled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

A compound labelled with tritium may be useful in identifying novel medicinal compounds capable of binding to and modulating the activity, by agonism, partial agonism, or antagonism, of an MCH1 receptor. Such tritium-labelled compounds may be used in assays that measure the displacement of such compounds to assess the binding of ligands that bind to MCH1 receptors.

In an even further embodiment, compounds disclosed herein may additionally comprise one or more atoms of an isotope. In a particular form of this embodiment, a compound comprises an isotopic halogen. Such labelled compounds are synthesized by incorporating labelled starting materials by known methods. In a particular embodiment, the isotope is selected from $^{18}F$, $^{123}I$, $^{125}I$, $^{131}I$, $^{75}Br$, $^{76}Br$, $^{77}Br$ or $^{82}Br$. In a more particular embodiment, the isotope is $^{18}F$.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates, or mixtures thereof, of the compounds of formula I. The optically active forms of the compound of the invention may be prepared, for example, by chiral chromatographic separation of a racemate for example using a Chiralpak® IA column (supplied by Chiral Technologies Europe) or a Chiralcel®OJ column (supplied by Chiral Technologies Europe), by synthesis from optically active starting materials or by asymmetric synthesis based on the procedures described hereafter.

It will further be understood that the present invention encompasses tautomers of the compounds of formula I.

It will be understood that certain compounds of the invention may exist in solvated, for example hydrated, as well as unsolvated forms. It will further be understood that the present invention encompasses all such solvated forms of the compounds of formula I.

The compounds of formula I can also form salts. As a result, when a compound of formula I is referred to herein, such reference includes, unless otherwise indicated, salts thereof. In one embodiment, the compounds of formula I form pharmaceutically acceptable salts. In another embodiment, the compounds of formula I form salts that can, for example, be used to isolate and/or purify the compounds of formula I.

Generally, pharmaceutically acceptable salts of a compound in accordance with formula I can be obtained by using standard procedures well known in the art. These standard procedures include, but are not limited to, for example, the reacting of a sufficiently basic compound, such as, for example, an alkyl amine with a suitable acid, such as, for example, hydrochloric acid or acetic acid, to afford a physiologically acceptable anion.

In one embodiment, a compound in accordance with formula I may be converted to a pharmaceutically acceptable salt or solvate thereof, particularly, an acid addition salt, such as, for example, hydrochloride, hydrobromide, phosphate, acetate, fumarate, maleate, tartrate, citrate, methanesulphonate, and p-toluenesulphonate.

In general, the compounds of formula I can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

The term "amino-protecting group" refers to art-recognized moieties capable of attaching to an amino group so as to prevent the amino group from taking place in reactions occurring elsewhere on the molecule containing the amino group. Acceptable amino-protecting groups, include but are not limited to, for example, amino-protecting groups described in "Protective Groups in Organic Synthesis", 2nd edition, John Wiley & Sons, 1991. The amino-protecting group may, for example, be a urethane type protective group (which is also referred to as a carbamate protective group), including but not limited to, for example, arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

Compounds of formula I may be prepared by a) reacting a compound of formula IV

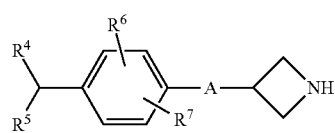

IV in which $R^4$, $R^5$, $R^6$, $R^7$ and A are as previously defined with a compound of formula V

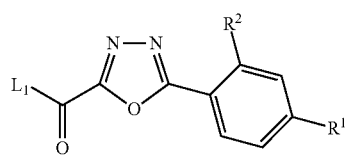

V in which $R^1$ and $R^2$ are as previously defined and $L_1$ represents a leaving group for example a $C_{1-4}$alkoxy group; or b) reacting a compound of formula VI

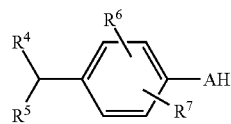

VI in which $R^4$, $R^5$, $R^6$, $R^7$ and A are as previously defined with a compound of formula VII

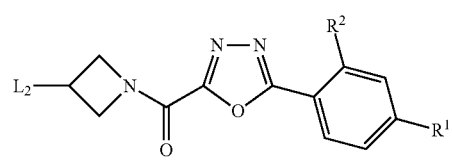

VII in which $R^1$ and $R^2$ are as previously defined and $L_2$ represents a leaving group, for example mesyloxy or tosyloxy, in the presence of a base such as for instance $Cs_2CO_3$, optionally in the presence of a solvent, such as, for example, DMF or DMA, and at a temperature in the range of 0 to 150° C. particularly in the range of 50 to 120° C.; or c) reacting a compound of formula VIII

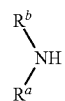

VIII in which $R^a$ and $R^b$ are as previously defined with a compound of formula IX

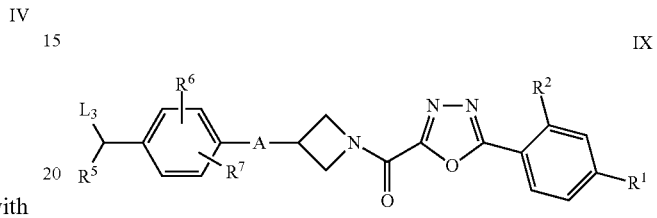

IX in which $R^1$, $R^2$, $R^5$, $R^6$, $R^7$ and A are as previously defined and $L_3$ represents a leaving group for example halo particularly chloro or bromo; optionally in the presence of a solvent, such as, for example, DMF, and optionally in the presence of a base for example an amine for example N-ethyl-N-isopropylpropan-2-amine at a temperature in the range of 0 to 150° C., particularly in the range of 5 to 50° C.; or d) reacting a compound of formula VIII in which $R^a$ and $R^b$ are as previously defined with a compound of formula IX in which $R^1$, $R^2$, $R^5$, $R^6$, $R^7$ and A are as previously defined and $L_3$ represents an oxo group in the presence of a reducing agent, such as for instance sodium triacetoxyborohydride in an appropriate solvent, such as for example, dichloromethane.

If the compound of formula V is an ester, then a compound of formula I can be obtained by reacting a compound of formula IV and an ester of formula V optionally in the presence of a solvent, such as, for example, ethanol and at a temperature in the range of 0 to 150° C. particularly in the range of 50 to 120° C.

Compounds of formula IV and VI may be prepared as shown in scheme 1 below and by methods analogous to those described in the examples.

Scheme 1

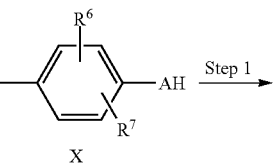

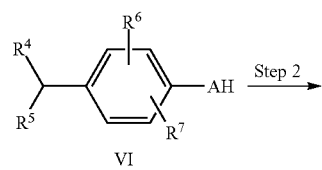

-continued

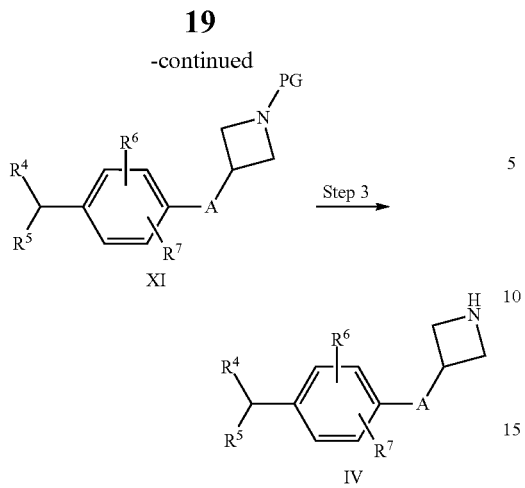

Step 1
A compound in accordance with formula VI can be obtained by reacting a compound of formula VIII in which $R^a$ and $R^b$ are as previously defined with an aldehyde or ketone derivative of formula X in which A, $R^5$, $R^6$ and $R^7$ are as previously defined and a reducing agent, such as for instance, sodium triacetoxyborohydride in an appropriate solvent, such as for example, dichloromethane.

Step 2
A compound in accordance with formula XI can be obtained by reacting a compound of formula VI with an azetidine compound of formula XII,

in which PG represents an amine protecting group, such as for example, tert-butoxycarbonyl and $L_4$ represents a leaving group, for example mesyloxy or tosyloxy in the presence of a base such as for instance $Cs_2CO_3$, in the presence of an appropriate solvent, such as, for example, DMF.

Step 3
A compound in accordance with formula IV can be obtained by treating a compound of formula XI with a deprotecting agent, such as for instance, HCl in an appropriate solvent, such as for example, dichloromethane.

Compounds of formula V may be prepared according to well known procedures, as for instance to those described in *Journal fuer Praktische Chemie*, 327, 109-116 (1985), employing benzohydrazide compounds in accordance with formula XIII,

in which $R^1$ and $R^2$ are as previously defined.

Compounds of formula IX and VII may be prepared as shown in scheme 2 below and by methods analogous to those described in the examples.

Scheme 2

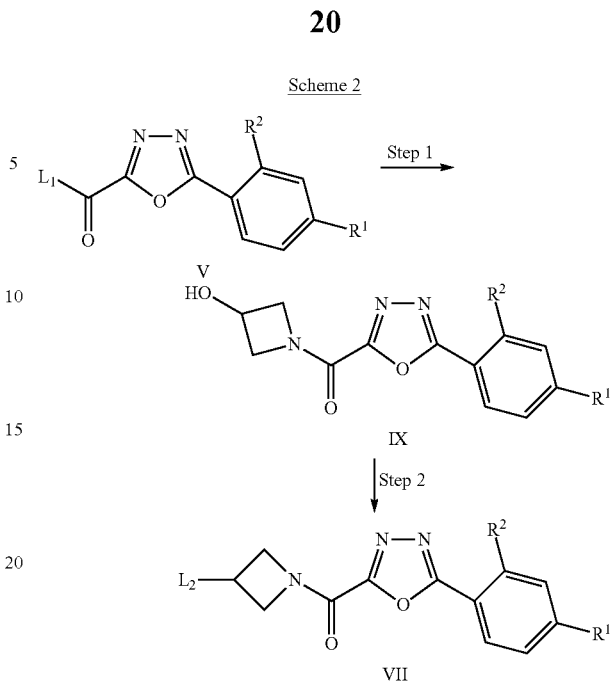

Step 1
A compound in accordance with formula IX can be obtained by reacting a compound of formula V in which $L_1$ and $R^1$ and $R^2$ are as previously defined with 3-hydroxyazetidine or a salt thereof in the presence of a base, such as for instance, triethylamine, optionally in the presence of a catalyst such as for instance sodium cyanide, in an appropriate solvent, such as for example, methanol.

Step 2
A compound in accordance with formula VII, in which $R^1$, $R^2$ and $L_2$ are as previously defined can be obtained by treating a compound of formula IX with an alcohol activating agent such as for instance methanesulfonyl chloride, in the presence of a base, such as for instance triethylamine, in an appropriate solvent such as dichloromethane.

Compounds of formula VIII, X, XII and XIII are either commercially available or may readily be prepared according to well-known procedures for those skilled in the art.

Certain compounds or formulae IV, V, VI, VII, IX and XI are believed to be novel and are herein claimed as a further aspect of the present invention. In a preferred aspect of the invention these compounds are in substantially pure form e.g. greater than 50% pure, particularly greater than 95% pure and more particularly more than 99% pure.

A further embodiment is directed to a method for treatment or prophylaxis of a disease or condition in which modulation of the MCH1 receptor is beneficial comprising administering to a warm-blooded animal in need of such treatment or prophylaxis a therapeutically effective amount of a compound of formula I or a pharmaceutically-acceptable salt thereof.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of an antagonistic compound of formula I.

A further embodiment is directed to the use of a compound in accordance with formula I, or pharmaceutically acceptable salts thereof, or mixtures thereof for the treatment or prophylaxis of a disease or condition in which modulation of the MCH1 receptor is beneficial.

A more particular embodiment relates to the use of antagonistic-compounds of formula I, or a pharmaceutically acceptable salt thereof, for the treatment or prophylaxis of a disease or condition in which modulation of the MCH1 receptor is beneficial.

Yet a further embodiment is directed to the use of a compound in accordance with formula I, or a pharmaceutically acceptable salts thereof, in the manufacture of a medicament for the treatment or prophylaxis of a disease or condition in which modulation of the MCH1 receptor is beneficial.

Still yet a further embodiment is directed to using a compound in accordance with formula I, or a pharmaceutically acceptable salt thereof, as a medicament.

Another embodiment is directed to a pharmaceutical composition comprising a compound in accordance with formula I, or a pharmaceutically acceptable salt thereof and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or pharmaceutically-acceptable salt thereof, for the treatment or prophylaxis of such disease or condition, and at least one pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

In one embodiment, the disease and/or condition for which a compound in accordance with formula I may be used in the treatment of or the prophylaxis of includes, but is not limited to, for example, mood disorders, anxiety disorders, and eating disorders.

Exemplary mood disorders include, but are not limited to, for example, depressive disorder(s), such as, for example, major depressive disorder(s) and dysthymic disorder(s); bipolar depression and/or bipolar mania, such as, for example, bipolar I, including but not limited to those with manic, depressive or mixed episodes, and bipolar II; cyclothymiac's disorder(s); anxious depression; and mood disorder(s) due to a general medical condition.

Exemplary anxiety disorder(s) include, but are not limited to, for example, panic disorder(s) without agoraphobia; panic disorder(s) with agoraphobia; agoraphobia without history of panic disorder(s); specific phobia; social phobia; obsessive-compulsive disorder(s); stress related disorder(s); posttraumatic stress disorder(s); acute stress disorder(s); generalized anxiety disorder(s); and generalized anxiety disorder(s) due to a general medical condition.

Exemplary eating disorders, include, but are not limited to, for example, obesity.

Many of the above conditions and disorder(s) are defined for example in the American Psychiatric Association: Diagnostic and Statistical Manual of Mental Disorders, Fourth Edition, Text Revision, Washington, D.C., American Psychiatric Association, 2000.

Another embodiment is directed to a method for treatment or prophylaxis of a mood disorder, anxiety disorder, or eating disorder comprising administering to a warm-blooded animal in need of such treatment or prophylaxis a therapeutically effective amount of a compound according to formula I, or a pharmaceutically acceptable salt, thereof.

Yet another embodiment is directed to a method for treatment or prophylaxis of at least one mood disorder comprising administering to a warm-blooded animal in need of such treatment or prophylaxis a therapeutically effective amount of a compound according to formula I, or a pharmaceutically acceptable salt, thereof.

Still yet another embodiment is directed to a method for treatment or prophylaxis of at least one anxiety disorder comprising administering to a warm-blooded animal in need of such treatment or prophylaxis a therapeutically effective amount of a compound according to formula I, or a pharmaceutically acceptable salt thereof.

Still an even further embodiment is directed to a method for treatment or prophylaxis of at least one eating disorder comprising administering to a warm-blooded animal in need of such treatment or prophylaxis a therapeutically effective amount of a compound according to formula I, or a pharmaceutically acceptable salt thereof.

Another embodiment provides a method for treatment or prophylaxis of at least one disease or condition selected from anxiety, depression and obesity in a warm-blooded animal, comprising administering to said animal in need of such treatment or prophylaxis a therapeutically effective amount of a compound according to formula I.

Yet another embodiment provides a method for treatment or prophylaxis of anxiety in a warm-blooded animal, comprising administering to said animal in need of such treatment or prophylaxis a therapeutically effective amount of a compound according to formula I.

A further embodiment provides a method for treatment or prophylaxis of general anxiety disorder in a warm-blooded animal, comprising administering to said animal in need of such treatment or prophylaxis a therapeutically effective amount of a compound according to formula I.

Still yet another embodiment provides a method for treatment or prophylaxis of depression in a warm-blooded animal, comprising administering to said animal in need of such treatment or prophylaxis a therapeutically effective amount of a compound according to formula I.

Still yet an even further embodiment provides a method for treatment or prophylaxis of obesity in a warm-blooded animal, comprising administering to said animal in need of such treatment or prophylaxis a therapeutically effective amount of a compound according to formula I.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of an antagonistic compound of formula I.

A further embodiment is directed to a method for treatment or prophylaxis of a disease or condition selected from anxiety, depression and obesity in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of anxiety in a warm-blooded animal, comprising administering to said animal in need of such treatment or prophylaxis a therapeutically effective amount of a compound of formula I or a pharmaceutically-acceptable salt thereof.

Yet a further embodiment is directed to a method for treatment or prophylaxis of general anxiety disorder in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of depression in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of obesity in a warm-blooded animal, comprising administering to said animal in need of such treatment or prophylaxis a therapeutically effective amount of a compound of formula I or a pharmaceutically-acceptable salt thereof.

An even still further embodiment is directed to a compound of with formula I, or a pharmaceutically acceptable salt thereof, for use in the treatment or prophylaxis of a disease or condition in which modulation of the MCH1 receptor is beneficial.

A more particular embodiment relates to an antagonistic-compound of formula I, or a pharmaceutically acceptable salt thereof, for use in the treatment or prophylaxis of a disease or condition in which modulation of the MCH1 receptor is beneficial.

A further embodiment is directed to a compound of formula I, or a pharmaceutically acceptable salt thereof for use in the treatment or prophylaxis of a disease or condition selected from mood disorder, anxiety disorder, and eating disorder.

A still further embodiment is directed to a compound of formula I, or a pharmaceutically acceptable salt thereof, for use in the treatment or prophylaxis of mood disorder.

An even further embodiment is directed to a compound of formula I, or a pharmaceutically acceptable salt thereof for use in the treatment or prophylaxis of anxiety disorder.

An even still further embodiment is directed to a compound of formula I, or a pharmaceutically acceptable salt thereof, for the treatment or prophylaxis of an eating disorder.

Yet a still further embodiment is directed to a compound of formula I, or a pharmaceutically acceptable salt thereof, for use in the treatment or prophylaxis of a disease or condition selected from anxiety, depression and obesity.

Still yet a further embodiment is directed to a compound of formula I, or a pharmaceutically acceptable salt thereof, for use in the treatment or prophylaxis of anxiety.

Yet still a further embodiment is directed to a compound of formula I, or a pharmaceutically acceptable salt thereof, for use in the treatment or prophylaxis of general anxiety disorder.

Even still yet a further embodiment is directed to a compound of formula I, or a pharmaceutically acceptable salt thereof, or mixtures thereof for use in the treatment or prophylaxis of depression.

Yet another embodiment is directed to a compound of formula I, or a pharmaceutically acceptable salt thereof, for use in the treatment or prophylaxis of obesity.

Yet a further embodiment is directed to the use of a compound of formula I, or a pharmaceutically acceptable salt thereof, in the manufacture of a medicament for the treatment or prophylaxis of a disease or condition in which modulation of the MCH1 receptor is beneficial.

A further embodiment is directed to the use of a compound of formula I, or a pharmaceutically acceptable salt thereof, in the manufacture of a medicament for the treatment or prophylaxis of a disease or condition selected from mood disorder, anxiety disorder, and eating disorder.

Yet a further embodiment is directed to using a compound of formula I, or a pharmaceutically acceptable salt thereof, in the manufacture of a medicament for the treatment or prophylaxis of mood disorder.

A still further embodiment is directed to using a compound of formula I, or a pharmaceutically acceptable salt thereof, in the manufacture of a medicament for the treatment or prophylaxis of anxiety disorder.

Still yet a further embodiment is directed to using a compound of formula I, or a pharmaceutically acceptable salt thereof, in the manufacture of a medicament for the treatment or prophylaxis of an eating disorder.

An even further embodiment is directed to using a compound of formula I, or a pharmaceutically acceptable salt thereof, in the manufacture of a medicament for the treatment or prophylaxis of a disease or condition selected from anxiety, depression and obesity.

A still even further embodiment is directed to using a compound of formula I, or a pharmaceutically acceptable salt thereof, in the manufacture of a medicament for the treatment or prophylaxis of anxiety.

A yet even further embodiment is directed to using a compound of formula I, or a pharmaceutically acceptable salt thereof, in the manufacture of a medicament for the treatment or prophylaxis of general anxiety disorder.

A yet still even further embodiment is directed to using a compound of formula I, or a pharmaceutically acceptable salt thereof, in the manufacture of a medicament for the treatment or prophylaxis of depression.

Another embodiment is directed to the use of a compound of formula I, or a pharmaceutically acceptable salt thereof, in the manufacture of a medicament for the treatment or prophylaxis of obesity.

A further embodiment is directed to using a compound of formula I, or a pharmaceutically acceptable salt thereof, for the treatment or prophylaxis insulin resistance, hepatic steatosis (including NASH), fatty liver, or sleep apnea.

Still yet a further embodiment is directed to using a compound of formula I, or a pharmaceutically acceptable salt thereof, as a medicament.

Another embodiment is directed to a pharmaceutical composition comprising a compound of formula I, or a pharmaceutically acceptable salt thereof, and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or a pharmaceutically-acceptable salt thereof, effective for treatment or prophylaxis of such disease or condition, and at least one pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

Yet another embodiment provides at least one process for preparing a compound of Formula I.

In still yet another embodiment, a compound of formula I, or a pharmaceutically acceptable salt thereof, and/or a pharmaceutical composition or formulation comprising a compound of formula I, or a pharmaceutically acceptable salt thereof, may be administered concurrently, simultaneously, sequentially or separately with at least one other pharmaceutically active compound selected from the following:

(i) antidepressants, including, but not limited to, for example, agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine, and equivalents and pharmaceutically active isomer(s) and metabolite(s) thereof;
(ii) atypical antipsychotics including, but not limited to, for example, quetiapine, and pharmaceutically active isomer(s) and metabolite(s) thereof;
(iii) antipsychotics including, but not limited to, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and metabolite(s) thereof;
(iv) anxiolytics including, but not limited to, for example, alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam, and equivalents and pharmaceutically active isomer(s) and metabolite(s) thereof;
(v) anticonvulsants including, but not limited to, for example, carbamazepine, valproate, lamotrogine, gabapentin, and equivalents and pharmaceutically active isomer(s) and metabolite(s) thereof;
(vi) Alzheimer's therapies including, but not limited to, for example, donepezil, memantine, tacrine, and equivalents and pharmaceutically active isomer(s) and metabolite(s) thereof;
(vii) Parkinson's therapies including, but not limited to, for example, deprenyl, L-dopa, Requip, Mirapex, MAOB inhibitors such as selegeline and rasagiline, comP inhibitors such as Tasmar, A-2 inhibitors, dopamine reuptake inhibitors, NMDA antagonists, Nicotine agonists, Dopamine agonists, inhibitors of neuronal nitric oxide synthase, and equivalents and pharmaceutically active isomer(s) and metabolite(s) thereof;
(viii) migraine therapies including, but not limited to, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;
(ix) stroke therapies including, but not limited to, for example, abciximab, activase, NXY-059, citicoline, crobenetine, desmoteplase, repinotan, traxoprodil, and equivalents and pharmaceutically active isomer(s) and metabolite(s) thereof;
(x) urinary incontinence therapies including, but not limited to, for example, darafenacin, falvoxate, oxybutynin, propiverine, robalzotan, solifenacin, tolterodine, and equivalents and pharmaceutically active isomer(s) and metabolite(s) thereof;
(xi) neuropathic pain therapies including, but not limited to, for example, gabapentin, lidoderm, pregablin, and equivalents and pharmaceutically active isomer(s) and metabolite(s) thereof;
(xii) nociceptive pain therapies including, but not limited to, for example, celecoxib, etoricoxib, lumiracoxib, rofecoxib, valdecoxib, diclofenac, loxoprofen, naproxen, paracetamol, and equivalents and pharmaceutically active isomer(s) and metabolite(s) thereof;
(xiii) insomnia therapies including, but not limited to, for example, agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem, and equivalents and pharmaceutically active isomer(s) and metabolite(s) thereof;
(xiv) mood stabilizers including, but not limited to, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof;
(xv) insulin or insulin analogues;
(xvi) insulin secretagogues including sulphonylureas (for example glibenclamide, glipizide), prandial glucose regulators (for example meglitindes e.g. repaglinide and nateglinide);
(xvii) dipeptidyl peptidase IV inhibitors (for example saxagliptin, sitagliptin, aloglitptin or vildagliptin);
(xviii) insulin sensitising agents including PPARgamma agonists (for example pioglitazone and rosiglitazone), and agents with combined PPARalpha and gamma activity;
(xix) agents that modulate hepatic glucose balance (for example biguanides e.g. metformin, fructose 1,6 bisphosphatase inhibitors, glycogen phopsphorylase inhibitors, glycogen synthase kinase inhibitors);
(xx) agents designed to reduce the absorption of glucose from the intestine (for example alpha glucosidase inhibitors e.g. acarbose);
(xxi) agents that prevent the reabsorption of glucose by the kidney (for example SGLT-2 inhibitors for example dapagliflozin or canagliflozin);
(xxii) agents designed to treat the complications of prolonged hyperglycaemia (for example aldose reductase inhibitors);
(xxiii) an anti-obesity compound, for example orlistat (EP 129 748) or sibutramine (GB 2,184,122 and U.S. Pat. No. 4,929,629);
(xxiv) anti-dyslipidaemia agents such as, HMG-CoA reductase inhibitors (eg statins for example rosuvastatin); PPARα agonists (fibrates, e.g. fenofibrate, clofibrate and gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
(xxv) antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
(xxvi) haemostasis modulators such as, antithrombotics, activators of fibrinolysis; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;
(xxvii) agents which antagonise the actions of glucagon;
(xxviii) anti-inflammatory agents, such as non-steroidal anti-inflammatory drugs (eg. aspirin) and steroidal anti-inflammatory agents (eg. cortisone);
(xxix) an antihypertensive compound, for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, an AT-1 receptor blocker, a saluretic, a diuretic or a vasodilator;
(xxx) a PDK inhibitor;
(xxxi) a phytosterol compound;
(xxxii) an 11β HSD-1 inhibitor;
(xxxiii) an UCP-1, 2 or 3 activator;
(xxxiv) a CB1 receptor modulator for example an inverse agonist or an antagonist e.g. rimonabant or taranabant;
(xxxv) an NPY receptor modulator; for example an NPY agonist or an NPY2 agonist or an NPY5 antagonist;
(xxxvi) an MC4r modulator for example an MC4r agonist;
(xxxvii) an MC3r modulator for example an MC3r agonist;
(xxxviii) an orexin receptor modulator for example an antagonist;
(xxxix) modulators of nuclear receptors for example LXR, FXR, RXR, GR, ERRα, β, PPARα, β, γ, δ and RORalpha;
(xl) a DGAT1 inhibitor;
(xli) a DGAT2 inhibitor;
(xlii) a DGAT2 anti-sense oligonucleotide;
(xliii) a fatty acid synthase inhibitor
(xliv) a CETP (cholesteryl ester transfer protein) inhibitor;
(xlv) a cholesterol absorption antagonist;
(xlvi) a MTP (microsomal transfer protein) inhibitor;
(xlvii) probucol;
(xlviii) a GLP-1 agonist;
(xlix) a glucokinase modulator
l) a ghrelin antibody;
li) a ghrelin antagonist;
lii) a GPR119 agonist and
liii) another melanin concentrating hormone (MCH) modulator for example an MCH-1 antagonist;
or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

The above other pharmaceutically active compound, when employed in combination with the compounds of formula I, or pharmaceutically acceptable salts thereof, or mixtures thereof may be used, for example, in the amounts indicated in the Physicians' Desk Reference (PDR) or as otherwise determined by one of ordinary skill in the art.

For the uses, methods, medicaments and compositions mentioned herein the amount of formula I compound, or pharmaceutically acceptable salts thereof, or mixtures thereof used and the dosage administered may vary with the formula I compound, or pharmaceutically acceptable salts, or mixtures thereof employed; and/or the desired mode of administration and/or treatment. However, in general, satisfactory results are obtained when a compound in accordance with formula I, or pharmaceutically acceptable salts, or mixtures thereof is administered at a daily dosage of about 0.1 mg to about 20 mg/kg of animal body weight. Such doses may be given in divided doses 1 to 4 times a day or in a sustained release form. For man, the total daily dose may, for example, range of from about 5 mg to about 1,400 mg, and more particularly from about 10 mg to about 100 mg. Unit dosage forms suitable for oral administration generally comprise, for example, from about 2 mg to about 1,400 mg of at least one compound in accordance with formula I, or pharmaceutically acceptable salts, or mixtures thereof admixed with at least one solid and/or liquid pharmaceutical carrier, lubricant, and/or diluent.

The specific dose level and frequency of dosage for any particular subject, however, may vary and generally depends on a variety of factors, including, but not limited to, for example, the bioavailability of the specific formula I compound(s), or pharmaceutically acceptable salts, or mixtures thereof in the administered form; metabolic stability and length of action of the specific formula I compound(s), or pharmaceutically acceptable salts, or mixtures thereof; species, age, body weight, general health, sex, and diet of the subject; mode and time of administration; rate of excretion; drug combination; and severity of the particular condition.

Compound(s) in accordance with formula I, or pharmaceutically acceptable salts, or mixtures thereof may be administered by any means suitable for the condition to be treated and the quantity of formula I, or pharmaceutically acceptable salts, or mixtures thereof to be delivered.

Compound(s) in accordance with formula I, or pharmaceutically acceptable salts, or mixtures thereof may be administered in the form of a conventional pharmaceutical composition by any route including, but not limited to, for example, orally, intramuscularly, subcutaneously, topically, intranasally, epidurally, intraperitoneally, intrathoracially, intravenously, intrathecally, intracerebroventricularly, and injecting into the joints.

In one embodiment, the route of administration is orally, intravenously or intramuscularly.

A compound of formula I, or pharmaceutically acceptable salts, or mixtures thereof may be used on their own or in the form of appropriate medicinal preparations for enteral or parenteral administration.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, at least one solid, at least one liquid, and mixtures thereof. The solid carrier can also be a diluent, flavoring agent, solubilizer, lubricant, suspending agent, binder, encapsulating material, and/or table disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with at least one finely divided compound of formula I, or pharmaceutically acceptable salts, or mixtures thereof.

A tablet can be prepared by, for example, mixing at least one compound in accordance with formula I, or pharmaceutically acceptable salts, or mixtures thereof in suitable proportions with a pharmaceutically acceptable carrier having the necessary binding properties and compacted into the desired shape and size.

A suppository can be prepared by, for example, mixing at least one compound of formula I, or pharmaceutically acceptable salts, or mixtures thereof with at least one suitable non-irritating excipient that is liquid at rectal temperature but solid at a temperature below rectal temperature, wherein the non-irritating excipient is first melted and the formula I compound dispersed therein. The molten homogeneous mixture in then poured into convenient sized molds and allowed to cool and solidify. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions.

Exemplary liquid pharmaceutical compositions suitable for parenteral administration include, but are not limited to, for example, sterile water or water propylene glycol solutions of at least one compound in accordance with formula I, or pharmaceutically acceptable salts, or mixtures thereof; and aqueous polyethylene glycol solutions of at least one compound in accordance with formula I, or pharmaceutically acceptable salts, or mixtures thereof.

Aqueous solutions for oral administration can be prepared by dissolving at least one compound in accordance with formula I, or pharmaceutically acceptable salts, or mixtures thereof in water and adding suitable colorants, flavoring agents, stabilizers, and/or thickening agents as desired.

Aqueous suspensions for oral administration can be prepared by dispersing at least one finely divided compound of formula I, or pharmaceutically acceptable salts, or mixtures thereof in water together with a viscous material, such as, for example, a natural synthetic gum, resin, methyl cellulose, and sodium carboxymethyl cellulose.

In one embodiment, the pharmaceutical composition contains from about 0.05% to about 99% w (percent by weight) of at least one compound in accordance with formula I, or pharmaceutically acceptable salts, or mixtures thereof. All percentages by weight being based on total composition.

In another embodiment, the pharmaceutical composition contains from about 0.10% to about 50% w (percent by weight) of at least one compound in accordance with formula I, or pharmaceutically acceptable salts, or mixtures thereof. All percentages by weight being based on total composition.

Also provided herein is a process for preparing a pharmaceutical composition comprising mixing or compounding the ingredients together and forming the mixed ingredients into tablets or suppositories; encapsulating the ingredients in capsules; or dissolving the ingredients to form injectable solutions.

Assay Methods:
MCH Binding Assay:

Binding of Melanin Concentrating Hormone (MCH) may be measured with a radioligand-binding assay employing [$^{125}$I]MCH and membranes expressing human Melanin Concentrating Hormone receptor 1 (MCHR1). Ligands that bind to MCHR1 may be identified by their ability to compete with the binding of [$^{125}$I]MCH.

[$^{125}$I]MCH may be purchased from Perkin Elmer (NEK373050UC 25 µCi). Membranes (2.20 mg/mL) may be prepared from CHOK1 cells expressing human MCH receptor 1 such as those obtainable from EuroScreen. Trizma, BSA, NaCl, and MgCl$_2$6H$_2$O may be purchased from Sigma. Human MCH may be purchased from Bachem (0.5 mg, cat #H-1482).

Saturation binding assays may be run in 50 mM Tris, pH 7.4, containing 3 mM MgCl$_2$ and 0.05% BSA. To perform an assay, 100 µL of 2-fold serially diluted radioligand [$^{125}$I]MCH is added to wells of a shallow 96-well plate. This is followed by addition of 100 µL of assay buffer containing membranes at a final protein concentration of 20 µg/mL. The mixture is incubated at room temperature for 1 h before being filtered through a Wallac A-filter treated with 0.1% PEI using a cell harvester (Skatron). Collected membranes are washed 3 times with 300 µL/well of wash buffer (50 mM Tris, pH 7.4, containing 5 mM MgCl$_2$ and 50 mM NaCl), and then dried in air overnight or at 60° C. $^{125}$I is measured by scintillation counting.

[$^{125}$I]MCH binding assays performed in the presence of test compounds, either at fixed or a series of concentrations, may be employed in a ligand competition binding assay. For dose-response assays, compounds may be 3-fold serially diluted in an assay plate to produce a range of concentrations. For single point assays, [$^{125}$I]MCH and membranes may be pre-mixed and then transferred to an assay plates with respective final membrane protein and radioligand concentrations of 20 µg/mL and 0.04 nM.

For analysis of data from saturation binding, cpm are converted to dpm, and nM radioligand concentration is calculated using vendor-provided specific radioactivity.

Saturation binding data may be analyzed using equation (1):

$$B = \frac{B_{max}[[^{125}I]MCH]}{K_d + [[^{125}I]MCH]} \quad (1)$$

where B is concentration of bound ligand, $B_{max}$ is the maximum concentration of bound ligand, and $K_d$ is the dissociation constant for ligand.

Percent inhibition (% Inh) may be calculated using equation (2):

$$\% \ Inh = 100 \bigg/ \left(1 - \frac{(counts_{sample} - counts_{negative})}{(counts_{positive} - counts_{negative})}\right) \quad (2)$$

IC$_{50}$ values may be calculated by conventional methods using non-linear squares analysis.

MCHR1 Receptor Activation Assay:

Melanin Concentrating Hormone Receptor 1 (MCHR1) is a G-protein coupled receptor that interacts with heterotrimeric G proteins containing a G$\alpha_{i/o}$ subunit. Binding of MCH to MCHR1 results in the exchange of GDP for GTP on the G$\alpha_{i/o}$ proteins associated with the activated receptor. This activation can be quantified by measuring the amount of a GTP analog, GTP$\gamma^{35}$S, bound to the membrane-associated receptor. GTP$\gamma^{35}$S is not hydrolyzed by the intrinsic GTPase activity of a G-protein but instead forms a stable complex. Activation of MCH1 receptors may thus be quantified by measuring the amount of GTP$\gamma^{35}$S bound to membranes prepared from cells expressing such receptors. Membranes may be isolated by filtration or may be bound on SPA beads (Amersham). Bound GTP$\gamma^{35}$S may then be quantified by determining the amount of $^{35}$S present. Inhibition of MCH binding by a competing ligand may thus be assessed by a decrease in the amount of GTP$\gamma^{35}$S bound to membranes in the presence of such a competing ligand.

IC$_{50}$ Values

The compounds of the examples when tested in the above referenced assays had an IC$_{50}$ value of less than about 100 nM. The IC$_{50}$ values for the Example compounds are set forth in Table 1 hereinbelow.

TABLE 1

| Example No. | GTP$\gamma^{35}$S IC$_{50}$ (nM) |
|---|---|
| 1 | 7 |
| 2 | 25 |
| 3 | 27 |
| 4 | 20 |
| 5 | 15 |
| 6 | 19 |

TABLE 1-continued

| Example No. | GTPγ$^{35}$S IC$_{50}$ (nM) |
|---|---|
| 7 | 21 |
| 8 | 27 |
| 9 | 44 |
| 10 | 41 |
| 11 | 51 |
| 12 | 30 |
| 13 | 29 |
| 14 | 30 |
| 15 | 10 |
| 16 | 20 |
| 17 | 25 |
| 18 | 25 |
| 19 | 6.5 |
| 20 | 24 |
| 21 | 22 |
| 22 | 25 |
| 23 | 99 |
| 24 | 44 |
| 25 | 34 |
| 26 | 30 |
| 27 | 21 |
| 28 | 27 |
| 29 | 86 |
| 30 | 40 |
| 31 | 20 |
| 32 | 15 |
| 33 | 34 |
| 34 | 18 |
| 35 | 19 |
| 36 | 13 |
| 37 | 17 |
| 38 | 27 |
| 39 | 49 |
| 40 | 27 |
| 41 | 25 |
| 42 | 26 |
| 43 | 11 |
| 44 | 10 |
| 45 | 16 |
| 46 | 18 |
| 47 | 19 |
| 48 | 18 |
| 49 | 37 |
| 50 | 35 |
| 51 | 19 |
| 52 | 24 |
| 53 | 28 |
| 54 | 31 |
| 55 | 22 |
| 56 | 13 |
| 57 | 18 |
| 58 | 29 |
| 59 | 11 |
| 60 | 19 |
| 61 | 22 |
| 62 | 13 |
| 63 | 23 |
| 64 | 12 |
| 65 | 20 |
| 66 | 10 |
| 67 | 23 |
| 68 | 21 |
| 69 | 22 |
| 70 | 20 |
| 71 | 23 |
| 72 | 15 |
| 73 | 14 |
| 74 | 18 |
| 75 | 17 |
| 76 | 23 |
| 77 | 40 |
| 78 | 42 |
| 79 | 34 |
| 80 | 23 |
| 81 | 25 |
| 82 | 22 |
| 83 | 25 |
| 84 | 17 |
| 85 | 19 |
| 86 | 15 |
| 87 | 8.1 |
| 88 | 17 |
| 89 | 22 |
| 90 | 16 |
| 91 | 11 |
| 92 | 15 |

The following compounds did not have an IC$_{50}$ value below 100 nM: (3-(4-((bis(2-methoxyethyl)amino)methyl)phenoxy)azetidin-1-yl)(5-phenyl-1,3,4-oxadiazol-2-yl)methanone, (3-(3-(difluoromethoxy)-4-((dimethylamino)methyl)phenoxy)azetidin-1-yl)(5-(4-methoxyphenyl)-1,3,4-oxadiazol-2-yl)methanone, [3-[4-[(dicyclopropylamino)methyl]-3-methyl-phenoxy]azetidin-1-yl]-(5-phenyl-1,3,4-oxadiazol-2-yl)methanone and (3-(4-((oxetan-3-ylamino)methyl)phenoxy)azetidin-1-yl)(5-s phenyl-1,3,4-oxadiazol-2-yl)methanone. In one embodiment these compounds are excluded from the present invention by a proviso.

Certain compounds of the invention are particularly advantageous because they exhibit selectivity between their MCH activity and their hERG activity.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

In general, the compounds of Formula I can be prepared in accordance with the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art. Combinatorial techniques can be employed in the preparation of compounds, for example, where the intermediates possess groups suitable for these techniques.

The following abbreviations are employed herein: ACN: acetonitrile; APCI: atmospheric pressure chemical ionization; aq.: aqueous; BOC: 1,1-dimethylethoxycarbonyl; Cs$_2$CO$_3$: cesium carbonate; DCM: dichloromethane; DIAD: diisopropylazodicarboxylate; DIBAL-H: diisobutylaluminium hydride; DIPEA: N,N-diisopropylethylamine; DMSO: dimethyl sulfoxide; EDCI: 1-(3-Dimethylaminopropyl)-3-ethylcarbodiimide hydrochloride; Et$_2$O: diethyl ether; EtOAc: ethyl acetate; EtOH: ethanol; h: hour(s); HPLC: high performance liquid chromatography; HCl: hydrochloric acid where a molarity is given or hydrogen chloride gas when a solvent other than water is used; H$_2$O: water; K$_2$CO$_3$: potassium carbonate; LC: liquid chromatography; MeOH: methanol; MgSO$_4$: magnesium sulfate; min: minutes; MS: mass spectrum; NaCl: Sodium chloride; NH$_4$Cl: ammonia hydrochloride; NaHCO$_3$: sodium bicarbonate; Na$_2$SO$_4$: Sodium sulfate; NH$_3$: Ammonia; NMR: nuclear magnetic resonance; psi: pounds per square inch; RT: room temperature; sat.:

saturated; TBTU: 2-(1H-benzo[d][1,2,3]triazol-1-yl)-1,1,3,3-tetramethylisouronium tetrafluoroborate; TEA: triethylamine; TFA: trifluoroacetic acid; and THF: tetrahydrofuran.

Melting points can be measured using melting point equipment or by differential scanning calorimery (DSC).

LC/MS HPLC method: Waters Acquity HPLC Column Acquity HPLC BEH C18, 1.7 um, 2.1×100 mm. Gradient 5-95% acetonitrile in ammonium carbonate buffer at pH10 (40 mM $NH_3$+6.5 mM $H_2CO_3$) in 5.8 minutes at 60° C. Flow 0.8 mL/min.

Chemical IUPAC names are generated by software provided by CambridgeSoft Corporation, Cambridge, Mass. 02140, USA.

Example 1

(5-(4-Chlorophenyl)-1,3,4-oxadiazol-2-yl)(3-(4-(pyrrolidin-1-ylmethyl)phenoxy)azetidin-1-yl)methanone

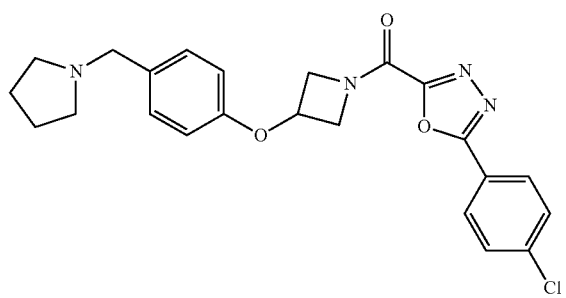 [SMILES: O=C(c1nnc(-c2ccc(Cl)cc2)o1)N1CC(Oc2ccc(CN3CCCC3)cc2)C1]

1A. tert-butyl 3-(4-(pyrrolidin-1-ylmethyl)phenoxy)azetidine-1-carboxylate

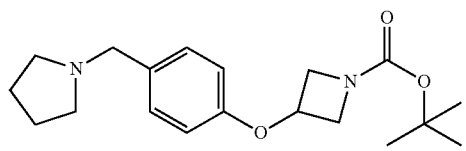 [SMILES: CC(C)(C)OC(=O)N1CC(Oc2ccc(CN3CCCC3)cc2)C1]

A mixture of NaH (55-65% disp. in oil, 0.62 g, 14.3 mmol) in dry DMF (20 mL) under nitrogen was cooled by an ice-bath. A solution of 4-(pyrrolidin-1-ylmethyl)phenol—see e.g. Bioorganic & Medicinal Chemistry Letters, 15, 3834-3837 (2005)—(2.1 g, 11.9 mmol) in DMF (20 mL) was added drop-wise. The mixture was stirred for one h and then tert-butyl 3-[(methylsulfonyl)oxy]azetidine-1-carboxylate (3.9 g, 15.5 mmol) in DMF (10.0 mL) was added. The mixture was heated to 80° C. overnight and then cooled to RT. Water (150 mL) was added and the mixture was extracted three times with EtOAc (100 mL). The combined organic solutions were washed with brine, dried ($MgSO_4$) and evaporated. The residue was purified twice by column chromatography on $SiO_2$ using 10-100% EtOAc/heptane as eluent. The product was further purified using 0.5% $NH_3$ in MeOH/DCM as eluent. There was obtained 2.5 g (64%) of 1A. $^1$H NMR (600 MHz, $CDCl_3$): δ 1.43 (s, 9H), 1.77 (s, 4H), 2.47 (s, 4H), 3.54 (s, 2H), 3.95-4.02 (m, 2H), 4.24-4.30 (m, 2H), 4.82-4.88 (m, 1H), 6.67 (d, 2H), 7.23 (d, 2H).

1B. 1-(4-(azetidin-3-yloxy)benzyl)pyrrolidine

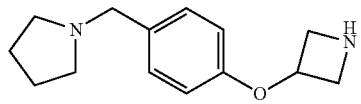

A solution of 1A (5.2 g, 15.5 mmol) in DCM (50 mL) was treated with TFA (10 g, 88 mmol) and stirred at RT for 17 h. The reaction mixture was concentrated and then co-evaporated using DCM. The residue was dissolved in water and the pH adjusted to pH 10 by adding NaOH. The solution was extracted several times with DCM and the organic solutions were filtered through a phase separator. The solvent was removed by evaporation. There was obtained 3.1 g (85%) of 1B as an oil. $^1$H NMR (500 MHz, $CDCl_3$): δ 1.69-1.83 (m, 4H), 2.43-2.57 (m, 4H), 3.53 (s, 2H), 3.73-3.81 (m, 2H), 3.87-3.92 (m, 2H), 4.93-5.01 (m, 1H), 6.68 (d, 2H), 7.20 (d, 2H).

1. 2-(4-Chlorophenyl)-5-({3-[4-(pyrrolidin-1-ylmethyl)phenoxy]azetidin-1-yl}carbonyl)-1,3,4-oxadiazole A mixture of 1B (1.0 g, 4.3 mmol) and ethyl 5-(4-chlorophenyl)-1,3,4-oxadiazole-2-carboxylate—see e.g. WO97/05131—(1.2 g, 4.7 mmol) was heated at 120° C. for 4 h. The residue was purified by column chromatography on $SiO_2$ using 5% triethylamine in EtOAc as eluent. There was obtained 0.46 g (24%) of 1 as a solid. $^1$H NMR (500 MHz, $CDCl_3$): δ 1.69-1.88 (m, 4H), 2.38-2.69 (m, 4H), 3.57 (s, 2H), 4.26-4.38 (m, 1H), 4.61-4.68 (m, 1H), 4.72-4.79 (m, 1H), 5.05-5.20 (m, 2H), 6.74 (d, 2H), 7.29 (d, 2H), 7.52 (d, 2H), 8.10 (d, 2H), MS (APCI+) m/z 439 [M+H]$^+$, LC purity: 96%.

Example 2

(5-(4-Methoxyphenyl)-1,3,4-oxadiazol-2-yl)(3-(4-(pyrrolidin-1-ylmethyl)phenoxy)azetidin-1-yl)methanone

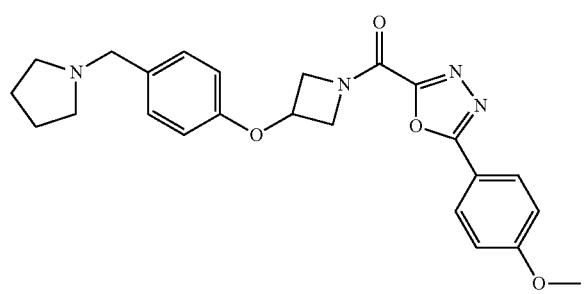

A mixture of 1B (62 mg, 0.27 mmol) and ethyl 5-(4-methoxyphenyl)-1,3,4-oxadiazole-2-carboxylate—see e.g. Journal fuer Praktische Chemie, 327, 109-16 (1985)—(79 mg, 0.32 mmol) was dissolved in ethanol (3 mL). The mixture was refluxed for 3 h. The solvent was removed by evaporation and the residue was partitioned between DCM and aqueous NaHCO₃ (sat.). The mixture was filtered through a phase separator and the solvent was removed by evaporation. The product was crystallized from cold methanol. There was obtained 65 mg (56%) of 2 as a white solid. ¹H NMR (500 MHz, CDCl₃): δ 1.72-1.84 (m, 4H), 2.41-2.54 (m, 4H), 3.57 (s, 2H), 3.90 (s, 3H), 4.28-4.34 (m, 1H), 4.59-4.69 (m, 1H), 4.71-4.80 (m, 1H), 5.02-5.18 (m, 2H), 6.72 (d, 2H), 7.04 (d, 2H), 7.27 (d, 2H), 8.10 (d, 2H), MS (APCI+) m/z 435 [M+H]⁺, LC purity: 97%.

Example 3

(5-Phenyl-1,3,4-oxadiazol-2-yl)(3-(4-(pyrrolidin-1-ylmethyl)phenoxy)azetidin-1-yl)methanone

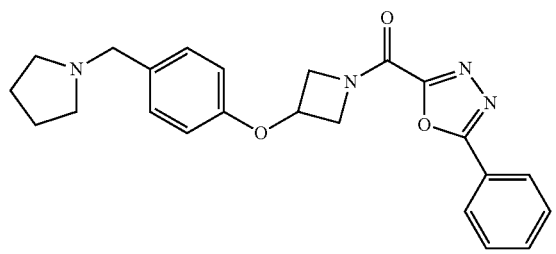 [SMILES: O=C(c1nnc(-c2ccccc2)o1)N1CC(Oc2ccc(CN3CCCC3)cc2)C1]

A mixture of 1B (200 mg, 0.86 mmol) and ethyl 5-phenyl-1,3,4-oxadiazole-2-carboxylate—commercially available—(244 mg, 1.12 mmol) was dissolved in ethanol (3 mL). The mixture was heated in a microwave oven at 120° C. for 45 min. Upon cooling, the product precipitated from the solution and was further cooled in a refrigerator over night. The crystals were filtered off, washed with cold methanol and dried. There was obtained 226 mg (65%) of 3 as a white solid. ¹H NMR (500 MHz, CDCl₃): δ 1.73-1.84 (m, 4H), 2.43-2.55 (m, 4H), 3.57 (s, 2H), 4.29-4.38 (m, 1H), 4.60-4.69 (m, 1H), 4.72-4.80 (m, 1H), 5.02-5.18 (m, 2H), 6.73 (d, 2H), 7.24-7.30 (m, 2H), 7.50. 7.62 (m, 3H), 8.17 (d, 2H), MS (APCI+) m/z 405 [M+H]⁺, LC purity: 96%.

Example 4

(5-(4-Fluorophenyl)-1,3,4-oxadiazol-2-yl)(3-(4-(pyrrolidin-1-ylmethyl)phenoxy)azetidin-1-yl)methanone

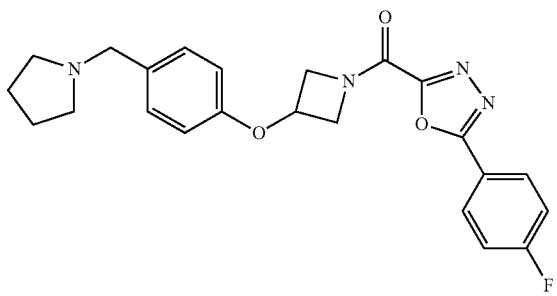 [SMILES: O=C(c1nnc(-c2ccc(F)cc2)o1)N1CC(Oc2ccc(CN3CCCC3)cc2)C1]

A mixture of 1B (200 mg, 0.86 mmol) and ethyl 5-(4-fluorophenyl)-1,3,4-oxadiazole-2-carboxylate—commercially available—(264 mg, 1.12 mmol) was dissolved in ethanol (3 mL). The mixture was heated in a microwave oven at 120° C. for 30 min. Upon cooling, the product precipitated from the solution and was further cooled in a refrigerator for 30 min. The crystals were filtered off, washed with cold methanol and dried. There was obtained 219 mg (60%) of 4 as a white solid. ¹H NMR (500 MHz, CDCl₃): δ 1.71-1.84 (m, 4H), 2.43-2.54 (m, 4H), 3.56 (s, 2H), 4.29-4.39 (m, 1H), 4.59-4.69 (m, 1H), 4.71-4.81 (m, 1H), 5.02-5.17 (m, 2H), 6.70-6.76 (m, 2H), 7.19-7.30 (m, 4H), 8.15-8.21 (m, 2H), MS (APCI+) m/z 423 [M+H]⁺, LC purity: 96%.

Example 5

(3-(4-(Pyrrolidin-1-ylmethyl)phenoxy)azetidin-1-yl)(5-(4-(trifluoromethyl)phenyl)-1,3,4-oxadiazol-2-yl)methanone formate

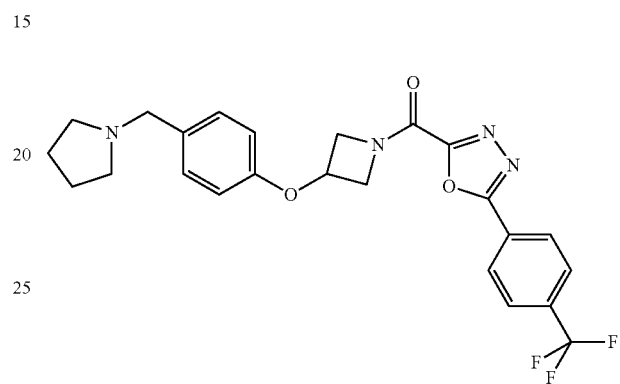

A mixture of 1B (200 mg, 0.86 mmol) and ethyl 5-(4-trifluoromethylphenyl)-1,3,4-oxadiazole-2-carboxylate—commercially available—(320 mg, 1.12 mmol) was dissolved in ethanol (4 mL). The mixture was heated in a microwave oven at 120° C. for 25 min. The solvent was removed by evaporation. The residue was purified by preparative chromatography on a Kromasil C8 column (10 μm 250× 20 ID mm) using a gradient of 10-80% acetonitrile in water/acetonitrile/formic acid (95/5/0.2), 100 mL/min. Fractions were collected, pooled and freeze dried. There was obtained 250 mg (56%) of 5 as a white solid. ¹H NMR (500 MHz, CDCl₃): δ 1.97-2.09 (m, 4H), 3.05-3.29 (m, 4H), 4.12 (s, 2H), 4.28-4.37 (m, 1H), 4.61-4.70 (m, 1H), 4.70-4.80 (m, 1H), 5.03-5.19 (m, 2H), 6.79 (d, 2H), 7.41 (d, 2H), 7.79 (d, 2H), 8.27 (d, 2H), 8.44 (s, 1H) MS (APCI+) m/z 473 [M+H]⁺, LC purity: 98%.

Example 6

(3-(4-(Pyrrolidin-1-ylmethyl)phenoxy)azetidin-1-yl)(5-p-tolyl-1,3,4-oxadiazol-2-yl)methanone hydrochloride

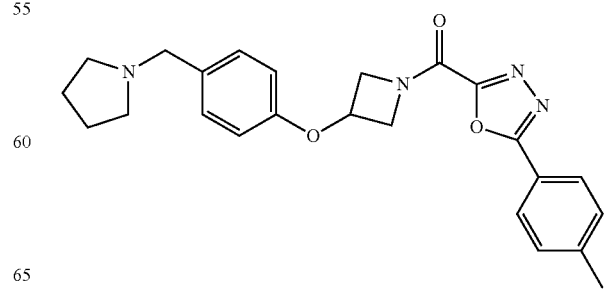

6A. Ethyl 2-(2-(4-methylbenzoyl)hydrazinyl)-2-oxoacetate

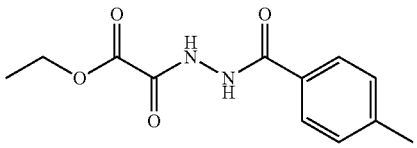 [SMILES: CCOC(=O)C(=O)NNC(=O)c1ccc(C)cc1]

4-Methylbenzohydrazide (6 g, 40 mmol) was dissolved in DCM (100 mL) and triethylamine (7.3 g, 80 mmol) was added. The solution was cooled with an ice-bath and ethyl chloro(oxo)acetate (5.5 g, 40 mmol) was added dropwise. After completed addition the reaction was stirred at 0° C. for 1 h and at rt for 2 h. The reaction mixture was washed with 0.2 M HCl, aqueous NaHCO$_3$ solution (sat.) and brine. The organic solution was filtered through a phase separator and the solvent was removed by evaporation. There was obtained 8.1 g (81%) of 6A as a white solid. $^1$H NMR (400 MHz, CDCl$_3$): δ 1.36 (t, 3H), 2.38 (s, 3H), 4.35 (q, 2H) 7.21 (d, 2H), 7.73 (d, 2H).

6B. Ethyl 5-p-tolyl-1,3,4-oxadiazole-2-carboxylate

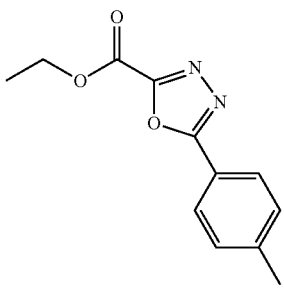 [SMILES: CCOC(=O)c1nnc(-c2ccc(C)cc2)o1]

6A (8.1 g, 32.4 mmol) was dissolved in toluene (200 ml) and pyridine (2.6 mL, 32.4 mmol). Thionyl chloride (9.6 g, 81 mmol) was added and the reaction was refluxed for 8 h. The solvent was evaporated and the residue was partitioned between DCM and aqueous NaHCO$_3$ (sat.). The organic phase was further washed with 0.1 M HCl and aqueous NaHCO$_3$ (sat.), filtered through a phase separator and the solvent was removed by evaporation. There was obtained 7.0 g (93%) of 6B as an off white solid. $^1$H NMR (400 MHz, CDCl$_3$): δ 1.48 (t, 3H), 2.44 (s, 3H), 4.54 (q, 2H), 7.34 (d, 2H), 8.04 (d, 2H).

6C. 2-(4-Methylphenyl)-5-({3-[4-pyrrolidin-1-ylmethyl)phenoxy]azetidin-1-yl}carbonyl)-1,3,4-oxadiazole hydrochloride A mixture of 1B (0.12 g, 0.52 mmol) and ethyl 5-(4-methylphenyl)-1,3,4-oxadiazole-2-carboxylate 6B (0.13 g, 0.57 mmol) was heated at 120° C. for 2.5 h. The residue was purified by column chromatography on SiO$_2$ using 2-5% NH$_3$ in MeOH/DCM as eluent. The solvent was removed by evaporation and to the residue was added a solution of HCl in diethyl ether. After one hour the formed precipitate was isolated by filtration There was obtained 0.12 g (50%) of 6 as a solid. $^1$H NMR (400 MHz, DMSO-d$_6$): δ 1.82-2.08 (m, 4H), 2.52 (s, 3H) 4.06-4.29 (m, 3H), 4.58-4.81 (m, 2H), 5.12-5.34 (m, 2H), 7.04 (d, 2H), 7.48-7.62 (m, 4H), 8.05 (d, 2H), MS (APCI+) m/z 419 [M+H]$^+$, LC purity: 93%.

Example 7

(3-(3-Methoxy-4-(morpholinomethyl)phenoxy)azetidin-1-yl)(5-phenyl-1,3,4-oxadiazol-2-yl)methanone

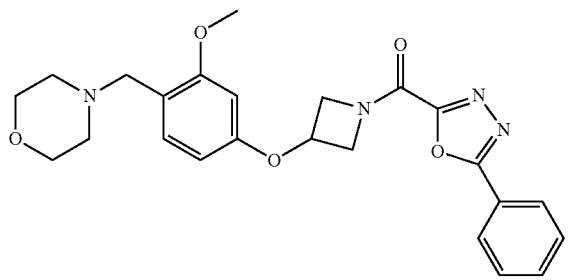 [SMILES: COc1cc(OC2CN(C(=O)c3nnc(-c4ccccc4)o3)C2)ccc1CN1CCOCC1]

7A. 3-Methoxy-4-(morpholinomethyl)phenol

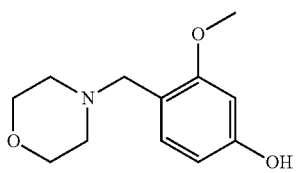 [SMILES: COc1cc(O)ccc1CN1CCOCC1]

A mixture of 4-hydroxy-2-methoxybenzaldehyde (1.0 g, 6.57 mmol) and morpholine (2.0 g, 23.0 mmol) in 50 ml dichloroethane was stirred at rt for 1 h. Sodium triacetoxyborohydride (2.0 g, 9.44 mmol) was added in portions over 20 minutes. The reaction mixture was stirred at rt over night. Aqueous NaHCO$_3$ (sat.) was added, the phases were separated and the aqueous phase was extracted with DCM once. The solvent was removed by evaporation and the residue was purified by column chromatography on SiO$_2$ using 5% triethylamine in EtOAc as eluent. There was obtained 1.19 g (81%) of 7A iii as a solid. $^1$H NMR (500 MHz, CDCl$_3$): δ 2.41-2.71 (m, 4H), 3.52 (s, 2H), 3.72 (s, 3H), 3.69-3.79 (m, 4H), 6.27 (d, 1H), 6.32 (s, 1H), 7.10 (d, 1H).

7B. tert-Butyl 3-(3-methoxy-4-(morpholinomethyl)phenoxy)azetidine-1-carboxylate

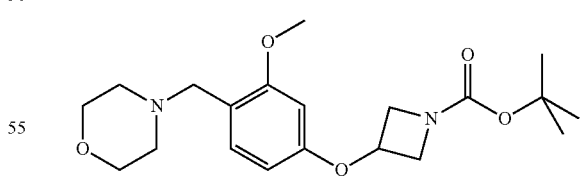

A mixture of NaH (55-65% disp. in oil, 0.30 g, 6.88 mmol) in dry DMF (5 mL) under nitrogen was cooled by a water-bath. A solution of 7A (1.17 g, 5.24 mmol) in DMF (10 mL) was added drop-wise over 15 minutes. The mixture was stirred for one h and then tert-butyl 3-[(methylsulfonyl)oxy]azetidine-1-carboxylate (1.7 g, 6.77 mmol) in DMF (10 mL) was added. The mixture was heated to 80° C. for 3 days and then cooled to RT. Water and some aqueous NaOH were added and the mixture was extracted three times with EtOAc.

The combined organic solutions were dried (MgSO$_4$) and evaporated. The residue was purified by column chromatography on SiO$_2$ using 5% triethylamine in EtOAc as eluent. There was obtained 2.1 g (104%) of 7B as a colorless oil. $^1$H NMR (500 MHz, CDCl$_3$): δ 1.45 (s, 9H), 2.39-2.56 (m, 4H), 3.48 (s, 2H), 3.65-3.75 (m, 4H), 3.79 (s, 3H), 3.95-4.04 (m, 2H), 4.23-4.33 (m, 2H), 4.82-4.91 (m, 1H), 6.19 (d, 1H), 6.38 (s, 1H), 7.21 (d, 1H).

7C.
4-(4-(Azetidin-3-yloxy)-2-methoxybenzyl)morpholine

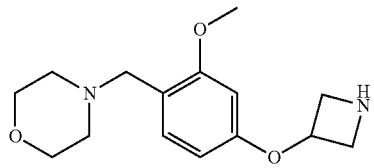 [SMILES: COc1cc(OC2CNC2)ccc1CN1CCOCC1]

A solution of 7B (2.1 g, 5.47 mmol) in DCM (20 mL) was treated with TFA (10 g, 88 mmol) and stirred at RT for 2 h. The reaction mixture was concentrated and the residue was dissolved in aqueous NaHCO$_3$ (sat.) and extracted several times with DCM and the organic solutions were filtered through a phase separator. The solvent was removed by evaporation and the residue was purified by column chromatography on SiO$_2$ using 10% triethylamine and 10% MeOH in EtOAc as eluent. There was obtained 1.0 g (66%) of 7C as a colorless oil. $^1$H NMR (500 MHz, CDCl$_3$): δ 2.40-2.53 (m, 4H), 3.47 (s, 2H), 3.66-3.74 (m, 4H), 3.78 (s, 3H), 3.77-3.84 (m, 2H), 3.89-3.97 (m, 2H), 4.94-5.04 (m, 1H), 6.23 (d, 1H), 6.37 (s, 1H), 7.19 (d, 1H).

7. 4-[2-Methoxy-4-({1-[(5-phenyl-1,3,4-oxadiazol-2-yl)carbonyl]azetidin-3-yl}oxy)benzyl]morpholine A mixture of 7C (0.25 g, 0.90 mmol), ethyl 5-phenyl-1,3,4-oxadiazole-2-carboxylate (0.22 g, 1.00 mmol) and EtOH (2 mL) was heated in a microwave oven at 120° C. for 60 min. The mixture was left over-night at RT. The formed precipitate was isolated by filtration and then washed with EtOH. There was obtained 0.18 g (45%) of 7 as a solid. $^1$H NMR (500 MHz, CDCl$_3$): δ 2.33-2.66 (m, 4H), 3.50 (s, 2H), 3.65-3.78 (m, 4H), 3.81 (s, 3H), 4.29-4.39 (m, 1H), 4.59-4.70 (m, 1H), 4.72-4.80 (m, 1H), 5.02-5.19 (m, 2H), 6.25 (d, 1H), 6.42 (s, 1H), 7.26 (s, 1H), 7.50-7.63 (m, 3H), 8.13-8.20 (m, 2H), MS (APCI+) m/z 451 [M+H]$^+$, LC purity: 99%.

Example 8

(3-(3-Methoxy-4-(morpholinomethyl)phenoxy)azetidin-1-yl)(5-(4-methoxyphenyl)-1,3,4-oxadiazol-2-yl)methanone

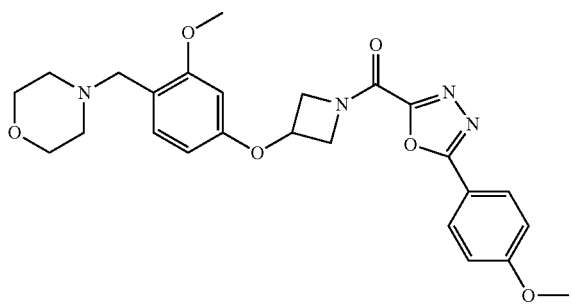 [SMILES: COc1ccc(-c2nnc(C(=O)N3CC(Oc4ccc(CN5CCOCC5)c(OC)c4)C3)o2)cc1]

Using a similar protocol as described in Example 7 employing 7C (0.25 g, 0.90 mmol) and ethyl 5-(4-methoxyphenyl)-1,3,4-oxadiazole-2-carboxylate (0.25 g, 1.00 mmol) as starting materials afforded 0.23 g (54%) of 8 as a solid. $^1$H NMR (500 MHz, CDCl$_3$): δ 2.40-2.55 (m, 4H), 3.50 (s, 2H), 3.68-3.77 (m, 4H), 3.80 (s, 3H), 3.89 (s, 3H), 4.28-4.36 (m, 1H), 4.59-4.78 (m, 2H), 5.02-5.17 (m, 2H), 6.21-6.28 (m, 1H), 6.39-6.44 (m, 1H), 7.02 (d, 2H), 7.25 (s, 1H), 8.10 (d, 2H), MS (APCI+) m/z 481 [M+H]$^+$, LC purity: 98%.

Example 9

(3-(2-Methyl-4-((4-methylpiperazin-1-yl)methyl)phenoxy)azetidin-1-yl)(5-phenyl-1,3,4-oxadiazol-2-yl)methanone

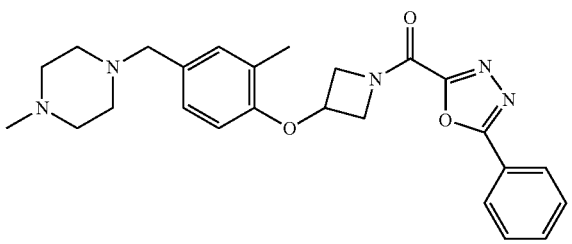 [SMILES: Cc1cc(CN2CCN(C)CC2)ccc1OC1CN(C(=O)c2nnc(-c3ccccc3)o2)C1]

9A.
2-Methyl-4-((4-methylpiperazin-1-yl)methyl)phenol

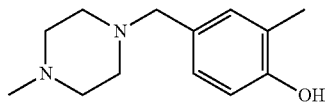

A mixture of 4-hydroxy-3-methylbenzaldehyde (3.27 g, 24 mmol) and 1-methylpiperazine (2.7 g, 27.0 mmol) in dichloroethane (100 mL) was stirred at rt for 30 min. Sodium triacetoxyborohydride (6.2 g, 29 mmol) was added in portions and the reaction mixture was stirred at rt over night. A further portion of 1-methylpiperazine was added and stirring was continued for 24 h. Aqueous NaHCO$_3$ (sat.) was added, the phases were separated and the aqueous phase was saturated with sodium chloride and extracted with DCM twice. The combined organic solutions were dried (MgSO$_4$) and evaporated and the residue was purified by column chromatography on SiO$_2$ using 0-20% MeOH in EtOAc:MeOH 95:5 as eluent. There was obtained 3.50 g (66%) of 9A as a solid. $^1$H NMR (500 MHz, CDCl$_3$): δ 2.21 (2, 3H), 2.29 (s, 3H), 2.32-2.72 (bm, 8H), 3.42 (s, 2H), 6.55 (d, 1H), 6.90 (d, 1H), 7.02 (s, 1H).

9B. tert-Butyl 3-(2-methyl-4-((4-methylpiperazin-1-yl)methyl)phenoxy)azetidine-1-carboxylate

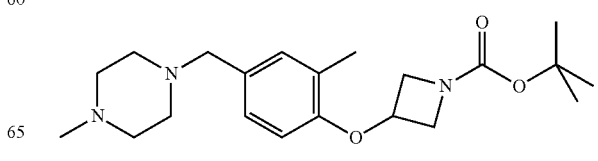

A mixture of NaH (55-65% disp. in oil, 0.50 g, 11.5 mmol) in dry DMF (10 mL) under nitrogen was cooled by an ice-water bath. A solution of 9A (2.0 g, 9.1 mmol) in DMF (15 mL) was added drop-wise over 15 minutes. The mixture was stirred for 15 minutes and then tert-butyl 3-[(methylsulfonyl)oxy]azetidine-1-carboxylate (3.0 g, 11.8 mmol) in DMF (15 mL) was added. The mixture was heated to 80° C. over night and then cooled to RT. Water and some aqueous NaOH were added and the mixture was extracted three times with DCM. The combined organic solutions were dried (MgSO$_4$) and evaporated. The residue was purified by column chromatography on SiO$_2$ using 5% triethylamine in EtOAc as eluent. There was obtained 2.18 g (64%) of 9B as a colorless oil. $^1$H NMR (500 MHz, CDCl$_3$): δ 1.45 (s, 9H), 2.22 (s, 3H), 2.28 (s, 3H), 2.30-2.63 (bm, 8H), 3.40 (s, 2H), 3.96-4.04 (m, 2H), 4.24-4.34 (m, 2H), 4.79-4.89 (m, 1H), 6.37 (d, 1H), 7.03 (d, 1H), 7.11 (s, 1H).

9C. 1-(4-(Azetidin-3-yloxy)-3-methylbenzyl)-4-methylpiperazine

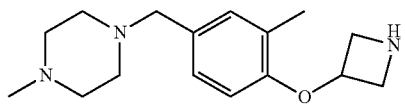 [SMILES: Cc1cc(CN2CCN(C)CC2)ccc1OC1CNC1]

A solution of 9B (2.18 g, 5.81 mmol) in DCM (40 mL) was treated with TFA (10 g, 88 mmol) and stirred at 0° C. for 3 h. The reaction mixture was concentrated and the residue was dissolved in aqueous NaHCO$_3$ (sat.) and extracted several times with DCM. The organic solutions were filtered through a phase separator. The solvent was removed by evaporation and the residue was purified by column chromatography on SiO$_2$ using 10% triethylamine and 10% MeOH in EtOAc as eluent. There was obtained 1.44 g (90%) of 9C as a colorless oil. $^1$H NMR (500 MHz, CDCl$_3$): δ 2.22 (s, 3H), 2.28 (s, 3H), 2.27-2.70 (bm, 8H), 3.40 (s, 2H), 3.75-3.85 (m, 2H), 3.88-3.98 (m, 2H), 4.92-5.02 (m, 1H), 6.43 (d, 1H), 7.01 (d, 1H), 7.09 (s, 1H).

9. 1-Methyl-4-[3-methyl-4-({1-[5-phenyl-1,3,4-oxadiazol-2-yl)carbonyl]azetidin-3-yl}oxy)benzyl]piperazine A mixture of 9C (200 mg, 0.74 mmol), ethyl 5-phenyl-1,3,4-oxadiazole-2-carboxylate (0.17 g, 0.77 mmol) and toluene (20 mL) was boiled under reflux for 6 h. The mixture was partly concentrated and then further boiled under reflux for 30 h. The solvent was removed by evaporation and the residue was purified by preparative chromatography on a Kromasil C8 column using a gradient of acetonitrile in water/acetic acid (0.2%). Pure fractions were combined and the solvent was removed by evaporation and then by freeze drying. There was obtained 140 mg (41%) of 9 as a foam. $^1$H NMR (500 MHz, DMSO-d$_6$): δ 2.13 (s, 3H), 2.19 (s, 3H), 2.20-2.45 (bm, 8H), 2.54 (s, 2H), 4.05-4.15 (m, 1H), 4.49-4.69 (m, 2H), 5.04-5.20 (m, 2H), 6.67 (d, 1H), 7.01-7.14 (m, 2H), 7.60-7.75 (m, 3H), 8.07 (d, 2H), MS (APCI+) m/z 448 [M+H]$^+$, LC purity: 99%.

Example 10

(5-(4-Methoxyphenyl)-1,3,4-oxadiazol-2-yl)(3-(2-methyl-4-((4-methylpiperazin-1-yl)methyl)phenoxy)azetidin-1-yl)methanone

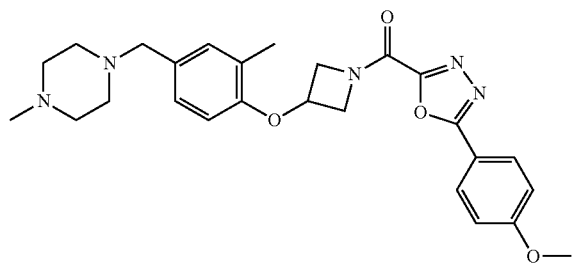

A mixture of 9C (0.20 g, 0.74 mmol), ethyl 5-(4-methoxyphenyl)-1,3,4-oxadiazole-2-carboxylate (0.18 g, 0.73 mmol) and toluene (3 mL) was heated in a microwave oven at 130° C. for 1 h and then at 140° C. for 2 h. The solvent was removed by evaporation and the residue was purified by preparative chromatography on a Kromasil C8 column using a gradient of acetonitrile in water/acetic acid (0.2%). Pure fractions were combined and the solvent was removed by evaporation and then by freeze drying. There was obtained 0.31 g (88%) of 10 as a foam. $^1$H NMR (500 MHz, CDCl$_3$): δ 2.23 (s, 3H), 2.30 (s, 3H), 2.30-2.75 (bm, 8H), 3.42 (s, 2H), 3.84 (s, 3H) 4.27-4.37 (m, 1H), 4.59-4.80 (m, 2H), 4.99-5.17 (m, 2H), 6.43 (d, 1H), 7.97-7.17 (m, 4H), 8.09 (d, 2H), MS (APCI+) m/z 478 [M+H]$^+$, LC purity: 98%.

Example 11

(3-(2-Methyl-4-((4-methylpiperazin-1-yl)methyl)phenoxy)azetidin-1-yl)(5-p-tolyl-1,3,4-oxadiazol-2-yl)methanone

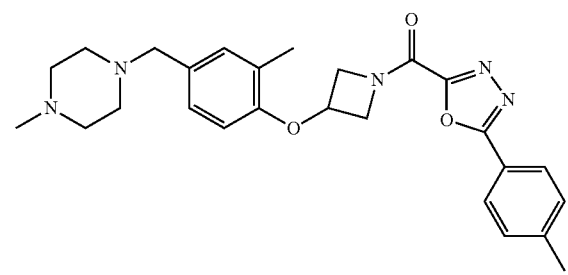

Using a similar protocol as described in Example 10 employing 9C (0.20 g, 0.73 mmol) and 6B (0.19 g, 0.82 mmol) as starting materials afforded 0.26 g (77%) of 11 as a foam. $^1$H NMR (500 MHz, CDCl$_3$): δ 2.24 (s, 3H), 2.33 (s, 3H), 2.44 (s, 3H) 2.36-2.76 (bm, 8H), 3.44 (s, 2H), 4.29-4.37 (m, 1H), 4.61-4.80 (m, 2H), 5.01-5.18 (m, 2H), 6.44 (d, 1H), 7.03-7.17 (m, 2H), 7.33 (d, 2H), 8.05 (d, 2H), MS (APCI+) m/z 462 [M+H]+, LC purity: 96%.

Example 12

(5-(4-Methoxyphenyl)-1,3,4-oxadiazol-2-yl)(3-(2-methyl-4-(morpholinomethyl)-phenoxy)azetidin-1-yl)methanone

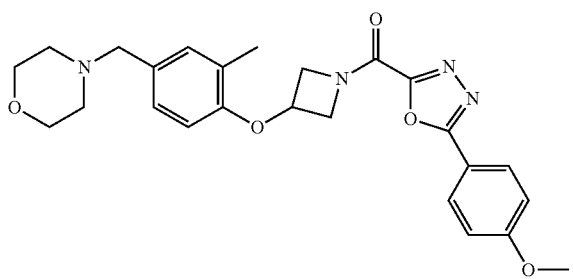 [SMILES: COc1ccc(-c2nnc(C(=O)N3CC(Oc4ccc(CN5CCOCC5)cc4C)C3)o2)cc1]

12A. tert-butyl 3-(2-methyl-4-(morpholinomethyl) phenoxy)azetidine-1-carboxylate

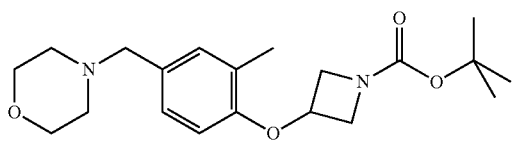 [SMILES: Cc1cc(CN2CCOCC2)ccc1OC1CN(C(=O)OC(C)(C)C)C1]

A mixture of NaH (55-65% disp. in oil, 0.55 g, 12.5 mmol) in dry DMF (10 mL) under nitrogen was cooled by an ice-bath. A solution of 2-methyl-4-(morpholin-4-ylmethyl)phenol—see WO 2006133567—(2.0 g, 9.6 mmol) in DMF (25 mL) was added drop-wise over 10 minutes. The mixture was stirred for one hour and then tert-butyl 3-[(methylsulfonyl) oxy]azetidine-1-carboxylate (3.2 g, 12.5 mmol) in DMF (15 mL) was added. The mixture was heated to 80° C. over night and then cooled to RT. Water (150 mL) was added and the mixture was extracted three times with EtOAc (100 mL). The residue was purified by column chromatography on SiO$_2$ using 10-75% EtOAc/heptane as eluent. The product was further purified using 0.5% NH$_3$ in MeOH/DCM as eluent. There was obtained 2.6 g (75%) of 12A as an oil. $^1$H NMR (400 MHz, CDCl$_3$): δ 1.45 (s, 9H), 2.22 (s, 3H), 2.34-2.49 (m, 4H), 3.40 (s, 2H), 3.62-3.76 (m, 4H), 3.94-4.07 (m, 2H), 4.23-4.35 (m, 2H), 4.79-4.92 (m, 1H), 6.38 (d, 1H), 7.03 (d, 1H), 7.11 (s, 1H).

12B. 4-(4-(Azetidin-3-yloxy)-3-methylbenzyl)morpholine

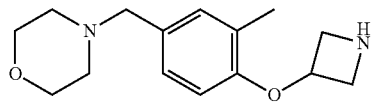 [SMILES: Cc1cc(CN2CCOCC2)ccc1OC1CNC1]

A solution of 12A (2.6 g, 7.17 mmol) in MeOH (10 mL) was treated with HCl in MeOH (40 ml, 50 mmol) and stirred at RT over night. The reaction mixture was concentrated and the residue was dissolved in water (15 mL). The solution was washed with EtOAc. DCM (100 mL) was added to the aqueous phase and then aqueous K$_2$CO$_3$ (sat., 20 mL) was added. The two phases were separated and organic solution was filtered through a phase separator. The solvent was removed by evaporation. There was obtained 1.8 g (96%) of 12B as a colorless oil. $^1$H NMR (600 MHz, CDCl$_3$): δ 2.21 (s, 3H), 2.33-2.48 (m, 4H), 3.38 (s, 2H), 3.63-3.73 (m, 4H), 3.74-3.84 (m, 2H), 3.87-3.96 (m, 2H), 4.91-5.02 (m, 1H), 6.43 (d, 1H), 7.01 (d, 1H), 7.09 (s, 1H).

12. 4-{4-[(1-{[5-(4-Methoxyphenyl)-1,3,4-oxadiazol-2-yl]carbonyl}azetidin-3-yl)oxy]-3-methylbenzyl}morpholine A mixture of 12B (0.18 g, 0.69 mmol) and ethyl 5-(4-methoxyphenyl)-1,3,4-oxadiazole-2-carboxylate (0.19 g, 0.75 mmol) was heated to 120° C. for 3 h using an oil-bath. Ethanol (0.1 mL) was added and the mixture was further heated to 120° C. for 30 min. The product was purified by column chromatography eluting with DCM and then with MeOH/DCM (0.5-2%). There was obtained 0.23 g (71%) of 12 as a solid. $^1$H NMR (600 MHz, CDCl$_3$): δ 2.22 (s, 3H), 2.33-2.50 (m, 4H), 3.39 (s, 2H) 3.60-3.77 (m, 4H), 3.86 (s, 3H), 4.26-4.36 (m, 1H), 4.57-4.78 (m, 2H), 4.99-5.16 (m, 2H), 6.42 (d, 1H), 6.99 (d, 2H), 7.05 (d, 1H), 7.12 (s, 1H), 8.07 (d, 2H), MS (APCI+) m/z 465 [M+H]+, LC purity: 99%.

Example 13

(3-(2-Methyl-4-(morpholinomethyl)phenoxy)azetidin-1-yl)(5-p-tolyl-1,3,4-oxadiazol-2-yl)methanone

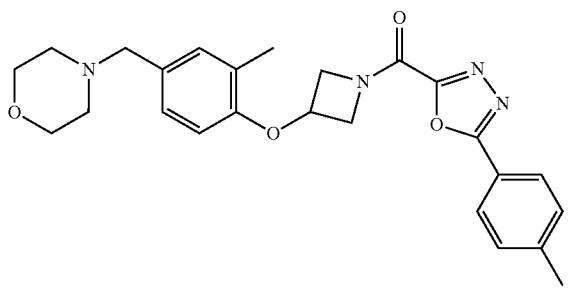 [SMILES: Cc1ccc(-c2nnc(C(=O)N3CC(Oc4ccc(CN5CCOCC5)cc4C)C3)o2)cc1]

Using a similar protocol as described in Example 12 employing 12B (0.18 g, 0.69 mmol) and 6B (0.18 g, 0.75 mmol) as starting materials afforded 0.22 g (72%) of 13 as a solid. $^1$H NMR (600 MHz, CDCl$_3$): δ 2.23 (s, 3H), 2.34-2.48 (m, 7H), 3.39 (s, 2H) 3.64-3.74 (m, 4H), 4.27-4.36 (m, 1H), 4.60-4.77 (m, 2H), 5.01-5.15 (m, 2H), 6.43 (d, 1H), 7.06 (d, 1H), 7.13 (s, 1H), 7.31 (d, 2H), 8.02 (d, 2H), MS (APCI+) m/z 449 [M+H]⁺, LC purity: 99%.

Example 14

(3-(2-Methyl-4-(morpholinomethyl)phenoxy)azetidin-1-yl)(5-phenyl-1,3,4-oxadiazol-2-yl)methanone

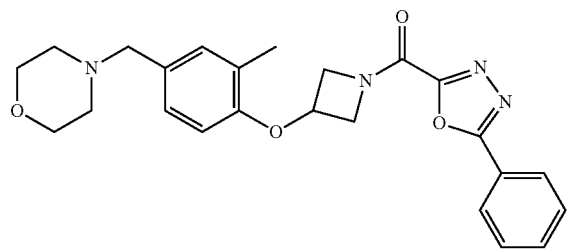 [SMILES: Cc1cc(CN2CCOCC2)ccc1OC1CN(C(=O)c2nnc(-c3ccccc3)o2)C1]

Using a similar protocol as described in Example 12 employing 12B (0.17 g, 0.65 mmol) and ethyl 5-phenyl-1,3,4-oxadiazole-2-carboxylate (0.16 g, 0.71 mmol) as starting materials afforded 0.20 g (72%) of 14 as a solid. ¹H NMR (400 MHz, CDCl₃): δ 2.18 (s, 3H), 2.23-2.53 (m, 4H), 3.34 (s, 2H) 3.50-3.81 (m, 4H), 4.16-4.38 (m, 1H), 4.48-4.80 (m, 2H), 4.88-5.20 (m, 2H), 6.26-6.50 (m, 1H), 6.89-7.17 (m, 2H), 7.33. 7.65 (m, 3H), 7.95-8.23 (m, 2H), MS (APCI+) m/z 435 [M+H]⁺, LC purity: 99%.

Example 15

(5-(4-Chlorophenyl)-1,3,4-oxadiazol-2-yl)(3-(2-methyl-4-(morpholinomethyl)phenoxy)azetidin-1-yl)methanone

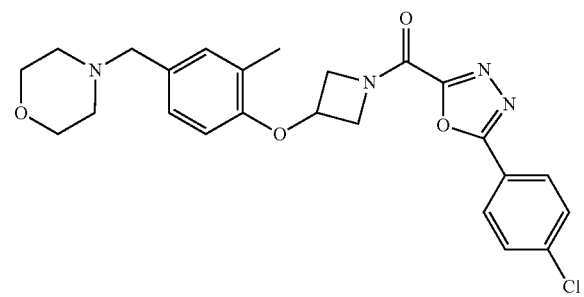 [SMILES: Cc1cc(CN2CCOCC2)ccc1OC1CN(C(=O)c2nnc(-c3ccc(Cl)cc3)o2)C1]

Using a similar protocol as described in Example 12 employing 12B (0.17 g, 0.65 mmol) and ethyl 5-(4-chlorophenyl)-1,3,4-oxadiazole-2-carboxylate (0.18 g, 0.71 mmol) as starting materials afforded 0.24 g (79%) of 15 as a solid. ¹H NMR (600 MHz, CDCl₃): δ 2.23 (s, 3H), 2.36-2.48 (m, 4H), 3.40 (s, 2H) 3.65-3.74 (m, 4H), 4.29-4.37 (m, 1H), 4.62-4.78 (m, 2H), 5.02-5.16 (m, 2H), 6.43 (d, 1H), 7.06 (d, 1H), 7.14 (s, 1H), 7.51 (d, 2H), 8.09 (d, 2H), MS (APCI+) m/z 469 [M+H]⁺, LC purity: 99%.

Example 16

(3-(4-((Dimethylamino)methyl)-2-methylphenoxy)azetidin-1-yl)(5-phenyl-1,3,4-oxadiazol-2-yl)methanone

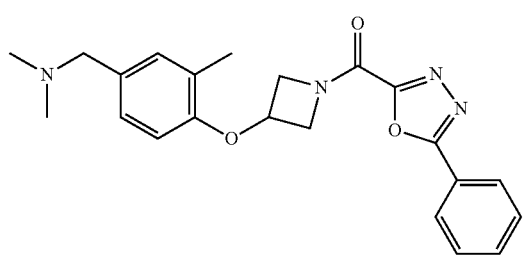 [SMILES: Cc1cc(CN(C)C)ccc1OC1CN(C(=O)c2nnc(-c3ccccc3)o2)C1]

16A. tert-Butyl 3-(4-((dimethylamino)methyl)-2-methylphenoxy)azetidine-1-carboxylate formate

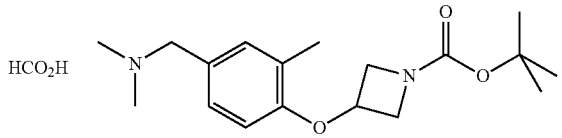 [SMILES: "HCO2H" ; Cc1cc(CN(C)C)ccc1OC1CN(C(=O)OC(C)(C)C)C1]

A mixture of NaH (55-65% disp. in oil, 0.35 g, 8.7 mmol) in dry DMF (10 mL) under nitrogen was cooled by an ice-bath. A solution of 4-[(dimethylamino)methyl]-2-methylphenol—commercially available—(1.1 g, 6.7 mmol) in DMF (5 mL) was added drop-wise over 10 minutes. The mixture was stirred for 30 minutes and then tert-butyl 3-[(methylsulfonyl)oxy]azetidine-1-carboxylate (1.84 g, 7.3 mmol) in DMF (5 mL) was added. The mixture was heated to 80° C. over night and then cooled to RT. Water (100 mL) was added and the mixture was extracted three times with EtOAc (50 mL). The combined organic phases were dried through a phase separator and the solvent was removed by evaporation. The residue was purified by preparative chromatography on a Kromasil C8 column (10 μm 250×20 ID mm) using a gradient of 10-50% acetonitrile in water/acetonitrile/formic acid (95/5/0.2), 100 mL/min. Fractions were collected, pooled and concentrated in vacuo. DCM was added and the solution was filtered through a phase separator and concentrated by evaporation. There was obtained 1.93 g (91%) of 16A as a colourless oil. ¹H NMR (500 MHz, CDCl₃): δ 1.45 (s, 9H), 2.37 (s, 3H), 2.62 (s, 6H), 3.97 (s, 2H), 3.92-4.04 (m, 2H), 4.24-4.35 (m, 2H), 4.81-4.92 (m, 1H), 6.59 (d, 1H), 6.62 (s, 1H), 7.35 (d, 1H), 8.42 (s, 1H).

16B. 1-(4-(Azetidin-3-yloxy)-3-methylphenyl)-N,N-dimethylmethanamine

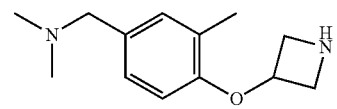 [SMILES: Cc1cc(CN(C)C)ccc1OC1CNC1]

Intermediate 16A (1.9 g, 5.93 mmol) was dissolved in a 4.0 M solution of HCl in MeOH (30 mL) and the reaction mixture was stirred at RT overnight. The mixture was concentrated and the residue was dissolved in water. The aqueous solution was basified to pH=10 with aqueous NaOH (1.0 M) and then extracted with DCM (4×30 mL). The combined organic phases were filtered through a phase separator and the solvent was removed by evaporation. There was obtained 1.02 g (78%) of 16B as a colorless oil. $^1$H NMR (500 MHz, CDCl$_3$): δ 2.21 (s, 6H), 2.33 (s, 3H), 3.30 (s, 2H), 3.73-3.84 (m, 2H), 3.85-3.96 (m, 2H), 4.91-5.03 (m, 1H), 6.52 (d, 1H), 6.58 (s, 1H), 7.11 (d, 1H).

16. N,N-dimethyl-1-[3-methyl-4-({1-[(5-phenyl-1,3,4-oxadiazol-2-yl)carbonyl]azetidin-3-yl}oxy)phenyl]methanamine Intermediate 16B (0.25 g, 1.13 mmol) was mixed with ethyl 5-phenyl-1,3,4-oxadiazole-2-carboxylate (0.27 g, 1.25 mmol) in a microwave vial, which then was sealed. The mixture was melted in a preheated oil bath and then stirred at 120° C. for 15 min using the oil bath. EtOH (0.2 mL) was added to the reaction mixture via a syringe and the mixture was stirred at 120° C. for another 3 h. To the mixture was added EtOH (5 mL) and the precipitate was stirred at rt for 20 min. The precipitate was filtered, washed with EtOH (20 mL) and then with Et$_2$O (3 mL). The product was dried in vacuo. There was obtained 0.26 g (57%) of 16 as a solid. $^1$H NMR (500 MHz, CDCl$_3$): δ 2.23 (s, 6H), 2.35 (s, 3H), 3.32 (s, 2H), 4.29-4.37 (m, 1H), 4.60-4.69 (m, 1H), 4.71-4.79 (m, 1H), 5.02-5.17 (m, 2H), 6.52-6.57 (m, 1H), 6.61 (s, 1H), 7.17 (d, 1H), 7.50-7.62 (m, 3H), 8.17 (d, 2H), MS (APCI+) m/z 393 [M+H]$^+$, LC purity: 98%.

Example 17

(3-(4-((Dimethylamino)methyl)-2-methylphenoxy)azetidin-1-yl)(5-(4-methoxyphenyl)-1,3,4-oxadiazol-2-yl)methanone

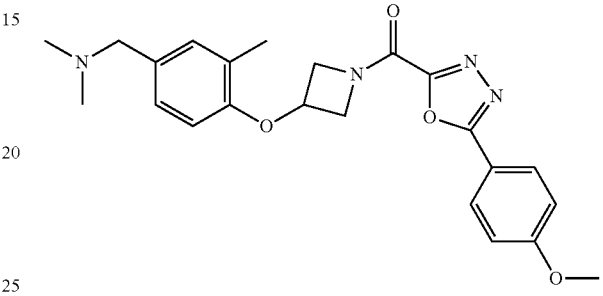

Using a similar protocol as described in Example 16 employing 16B (0.23 g, 1.04 mmol) and ethyl 5-(4-methoxyphenyl)-1,3,4-oxadiazole-2-carboxylate (0.28 g, 1.14 mmol) as starting materials afforded 0.25 g (56%) of 17 as a solid which was crystallised from ethanol, m.p. 137° C. $^1$H NMR (500 MHz, CDCl$_3$): δ 2.24 (s, 6H), 2.35 (s, 3H), 3.33 (s, 2H), 3.89 (s, 3H), 4.27-4.37 (m, 1H), 4.59-4.68 (m, 1H), 4.70-4.78 (m, 1H), 5.01-5.16 (m, 2H), 6.52-6.58 (m, 1H), 6.59-6.63 (m, 1H), 7.02 (d, 2H), 7.17 (d, 1H), 8.10 (d, 2H), MS (APCI+) m/z 423 [M+H]$^+$, LC purity: 94%.

Example 18

(3-(4-((Dimethylamino)methyl)-2-methylphenoxy)azetidin-1-yl)(5-p-tolyl-1,3,4-oxadiazol-2-yl)methanone

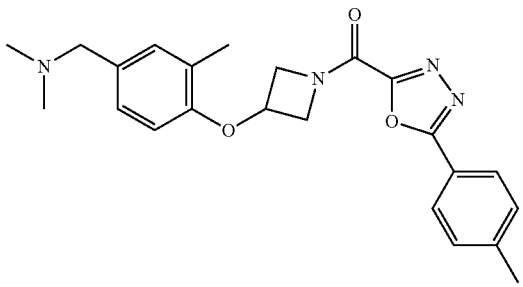

Using a similar protocol as described in Example 16 employing 16B (0.22 g, 1.00 mmol) and 6B (0.26 g, 1.10 mmol) as starting materials afforded 0.21 g (52%) of 18 as a solid. $^1$H NMR (500 MHz, CDCl$_3$): δ 2.25 (s, 6H), 2.35 (s, 3H), 2.45 (s, 3H), 3.35 (s, 2H), 4.284.37 (m, 1H), 4.59-4.68 (m, 1H), 4.70-4.78 (m, 1H), 5.02-5.17 (m, 2H), 6.5 (d, 1H), 6.61 (s, 1H), 7.18 (d, 1H), 7.34 (d, 2H), 8.05 (d, 2H), MS (APCI+) m/z 407 [M+H]+, LC purity: 95%.

Example 19

(5-(4-Chlorophenyl)-1,3,4-oxadiazol-2-yl)(3-(2-methyl-4-(pyrrolidin-1-ylmethyl)phenoxy)azetidin-1-yl)methanone

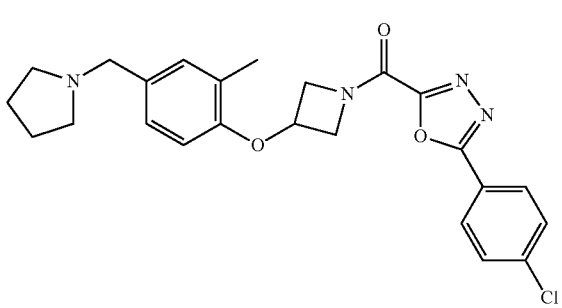 [SMILES: Cc1cc(CN2CCCC2)ccc1OC1CN(C(=O)c2nnc(-c3ccc(Cl)cc3)o2)C1]

19A. tert-butyl 3-(2-methyl-4-(pyrrolidin-1-ylmethyl)phenoxy)azetidine-1-carboxylate

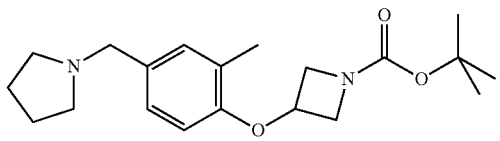 [SMILES: Cc1cc(CN2CCCC2)ccc1OC1CN(C(=O)OC(C)(C)C)C1]

A mixture of NaH (55-65% disp. in oil, 0.14 g, 3.4 mmol) in dry DMF (10 mL) under nitrogen was cooled by an ice-bath. A solution of 4-[(dimethylamino)methyl]-2-methylphenol—see WO 2006136924—(0.5 g, 2.6 mmol) in DMF (5 mL) was added drop-wise over 10 minutes. The mixture was stirred for 30 minutes and then tert-butyl 3-[(methylsulfonyl)oxy]azetidine-1-carboxylate (1.84 g, 7.3 mmol) in DMF (5 mL) was added. The mixture was heated to 80° C. over night and then cooled to RT. Water (100 mL) was added and the mixture was extracted three times with EtOAc (50 mL). The combined organic phases were filtered through a phase separator and the solvent was removed by evaporation. The residue was purified by preparative chromatography on a Kromasil C8 column (10 μm 250×20 ID mm) using a gradient of 10-50% acetonitrile in water/acetonitrile/formic acid (95/5/0.2), 100 mL/min. Fractions were collected, pooled and concentrated in vacuo. DCM was added and the solution was filtered through a phase separator and concentrated by evaporation. There was obtained 0.75 g (82%) of 19A as a colourless oil. ¹H NMR (500 MHz, CDCl₃): δ 1.45 (s, 9H), 1.92-2.08 (m, 4H), 2.37 (s, 3H), 3.01-3.20 (m, 4H), 3.91-4.03 (m, 2H), 4.08 (s, 2H), 4.23-4.35 (m, 2H), 4.79-4.91 (m, 1H), 6.58 (d, 1H), 6.61 (s, 1H), 7.38 (d, 1H), 8.49 (s, 1H).

19B. 1-(4-(Azetidin-3-yloxy)-3-methylbenzyl)pyrrolidine

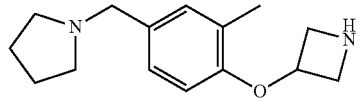 [SMILES: Cc1cc(CN2CCCC2)ccc1OC1CNC1]

Intermediate 19A (0.75 g, 2.15 mmol) was dissolved in a 4.0 M solution of HCl in MeOH (20 mL) and the reaction mixture was stirred at RT over night. The mixture was concentrated and the residue was dissolved in water. The solution was basified to pH=10 with aqueous NaOH (1.0 M) and extracted with DCM (4×30 mL). The combined organic phases were filtered through a phase separator and the solvent was removed by evaporation. There was obtained 0.43 g (72%) of 19B as a colorless oil. ¹H NMR (500 MHz, CDCl₃): δ 1.71-1.83 (m, 4H), 2.33 (s, 3H), 2.43-2.55 (m, 4H), 3.52 (s, 2H), 3.73-3.85 (m, 2H), 3.85-3.96 (m, 2H), 4.91-5.03 (m, 1H), 6.52 (d, 1H), 6.57 (s, 1H), 7.17 (d, 1H).

19. 2-(4-Chlorophenyl)-5-({3-[2-methyl-4-(pyrrolidin-1-ylmethyl)phenoxy]azetidin-1-yl}carbonyl)-1,3,4-oxadiazole Using a similar protocol as described in Example 16 employing 19B (0.20 g, 0.80 mmol) and ethyl 5-(4-chlorophenyl)-1,3,4-oxadiazole-2-carboxylate (0.22 g, 0.88 mmol) as starting materials afforded 0.21 g (46%) of 19 as a solid. ¹H NMR (500 MHz, CDCl₃): δ 1.72-1.84 (m, 4H), 2.35 (s, 3H), 2.43-2.58 (m, 4H), 3.54 (s, 2H), 4.28-4.36 (m, 1H), 4.59-4.68 (m, 1H), 4.70-4.78 (m, 1H), 5.02-5.16 (m, 2H), 6.55 (d, 1H), 6.60 (s, 1H), 7.23 (d, 1H), 7.52 (d, 2H), 8.11 (d, 2H), MS (APCI+) m/z 453 [M+H]+, LC purity: 94%.

Example 20

(3-(4-((Dimethylamino)methyl)-3-methylphenoxy)azetidin-1-yl)(5-(4-methoxyphenyl)-1,3,4-oxadiazol-2-yl)methanone

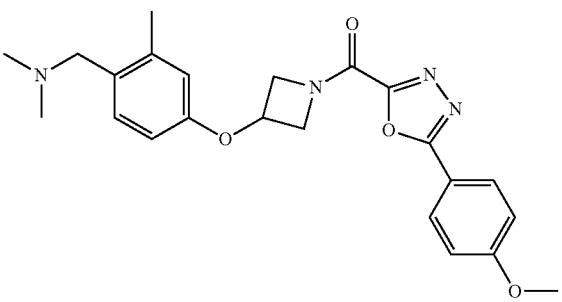

20A. 4-((Dimethylamino)methyl)-3-methylphenol

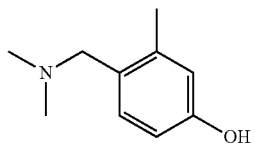

To a mixture of 4-hydroxy-2-methylbenzaldehyde (5.0 g, 37 mmol) and dimethylamine hydrochloride (12 g, 147 mmol) in DCM (200 mL), triethylamine (10 mL, 73 mmol) was added. Sodium triacetoxyborohydride (9.3 g, 44 mmol) was added in portions and the reaction mixture was stirred at rt over night. Water (20 mL) was added and the solution was concentrated by evaporation. THF (100 mL) and aqueous $NaHCO_3$ (sat., 30 mL) was added and the two phases were separated. NaCl (3-4 g) was added to the aqueous phase and it was extracted twice with THF (50 mL). The combined solutions were evaporated. EtOAc (150 mL) was added to the residue and the two phases were separated. The organic phase was dried ($Na_2SO_4$) and evaporated to dryness. There was obtained 5.8 g (96%) of 20A as an oil. $^1$H NMR (600 MHz, DMSO-$d_6$): δ 2.08 (s, 6H), 2.21 (s, 3H), 3.19 (s, 2H), 6.49 (d, 1H), 6.54 (s, 1H), 6.92 (d, 1H).

20B. tert-Butyl 3-(4-((dimethylamino)methyl)-3-methylphenoxy)azetidine-1-carboxylate

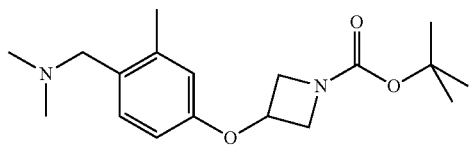 [SMILES: Cc1cc(OC2CN(C(=O)OC(C)(C)C)C2)ccc1CN(C)C]

A mixture of NaH (55-65% disp. in oil, 1.0 g, 23 mmol) in dry DMF (25 mL) under nitrogen was cooled by an ice-bath. A solution of 20A (2.9 g, 18 mmol) in DMF (20 mL) was added drop-wise over 10 minutes. The mixture was stirred for one hour and then tert-butyl 3-[(methylsulfonyl)oxy]azetidine-1-carboxylate (5.3 g, 21 mmol) in DMF (15 mL) was added. The mixture was heated to 80° C. over night and then cooled to RT. Water (200 mL) was added and the mixture was extracted three times with EtOAc (100 mL). The combined organic phases were dried ($MgSO_4$) and the solvent was removed by evaporation. The residue was purified by column chromatography on $SiO_2$ using 5-75% EtOAc/heptane as eluent. The product was further purified using 0.5% $NH_3$ in MeOH/DCM as eluent. There was obtained 3.1 g (55%) of 20B as a semi-solid. $^1$H NMR (600 MHz, CDCl$_3$): δ 1.44 (s, 9H), 2.21 (s, 6H), 2.32 (s, 3H), 3.29 (s, 2H), 3.93-4.02 (m, 2H), 4.21-4.32 (m, 2H), 4.79-4.89 (m, 1H), 6.48 (d, 1H), 6.55 (s, 1H), 7.12 (d, 1H).

20C. 1-(4-(Azetidin-3-yloxy)-2-methylphenyl)-N,N-dimethylmethanamine

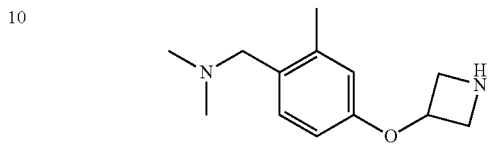

Intermediate 20B (3.1 g, 9.7 mmol) was dissolved in MeOH (10 mL) and HCl in MeOH (1.25 M, 50 mL) was added. The reaction mixture was stirred at RT overnight. The mixture was concentrated, the residue was dissolved in water (15 mL) and DCM (100 mL) was added. While stirring an aqueous solution of $K_2CO_3$ (sat., 30 mL) was added and the two phases were separated through a phase separator. The solvent was removed by evaporation. There was obtained 1.96 g (92%) of 20C as a colorless oil. $^1$H NMR (600 MHz, CDCl$_3$): δ 2.21 (s, 6H), 2.32 (s, 3H), 3.29 (s, 2H), 3.71-3.83 (m, 2H), 3.84-3.95 (m, 2H), 4.92-5.02 (m, 1H), 6.51 (d, 1H), 6.57 (s, 1H), 7.10 (d, 1H).

20. 1-{-4-[(1-{[5-(4-Methoxyphenyl)-1,3,4-oxadiazol-2-yl]carbonyl}azetidin-3-yl)oxy]-2-methylphenyl}-N,N-dimethylmethanamine Using a similar protocol as described in Example 16 employing 20C (0.16 g, 0.73 mmol) and ethyl 5-(4-methoxyphenyl)-1,3,4-oxadiazole-2-carboxylate (0.20 g, 0.80 mmol) as starting materials afforded 0.23 g (74%) of 20 as a solid. $^1$H NMR (600 MHz, CDCl$_3$): δ 2.21 (s, 6H), 2.33 (s, 3H), 3.30 (s, 2H), 3.87 (s, 3H), 4.27-4.35 (m, 1H), 4.58-4.66 (m, 1H), 4.69-4.76 (m, 1H), 5.00-5.15 (m, 2H), 6.53 (d, 1H), 6.58 (s, 1H), 7.00 (d, 2H), 7.14 (d, 1H), 8.08 (d, 2H), MS (APCI+) m/z 423 [M+H]$^+$, LC purity: 98%.

Example 21

(3-(4-((Dimethylamino)methyl)-3-methylphenoxy)azetidin-1-yl)(5-phenyl-1,3,4-oxadiazol-2-yl)methanone

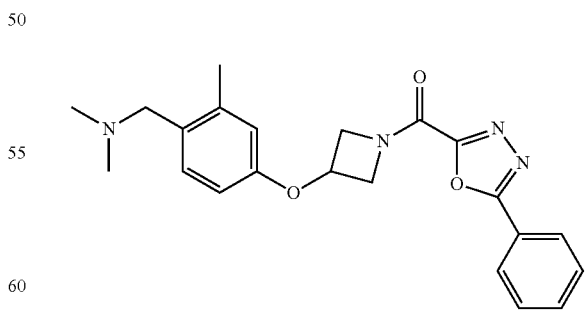

Intermediate 20C (0.16 g, 0.73 mmol) and ethyl 5-phenyl-1,3,4-oxadiazole-2-carboxylate (0.17 g, 0.80 mmol) were mixed together in a microwave vial. The vial was sealed and the mixture was then stirred at 120° C. for 2 hours using an oil bath. The mixture was cooled to room temperature. The product was purified by column chromatography eluting with DCM and MeOH (saturated with ammonia)/DCM (gradient, 0.5-2%). The solvent was removed by evaporation and the semi solid residue was triturated with Et₂O. There was obtained 0.27 g (93%) of the product as a crystalline solid m.p. 135° C. ¹H NMR (600 MHz, CDCl₃): δ 2.21 (s, 6H), 2.34 (s, 3H), 3.31 (s, 2H), 4.28-4.35 (m, 1H), 4.59-4.67 (m, 1H), 4.70-4.78 (m, 1H), 5.01-5.15 (m, 2H), 6.54 (d, 1H), 6.60 (s, 1H), 7.15 (d, 1H), 7.49-7.62 (m, 3H), 8.16 (d, 2H), MS (APCI+) m/z 393 [M+H]⁺, LC purity: 99%.

Example 22

(3-(4-((Dimethylamino)methyl)-3-methylphenoxy) azetidin-1-yl)(5-p-tolyl-1,3,4-oxadiazol-2-yl)methanone

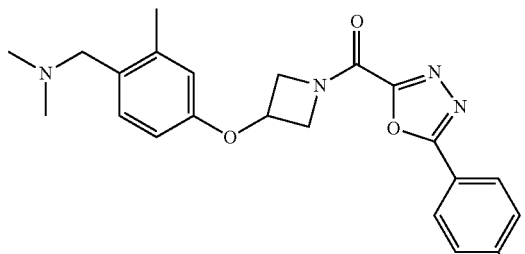 [SMILES: Cc1cc(OC2CN(C(=O)c3nnc(-c4ccccc4)o3)C2)ccc1CN(C)C]

Using a similar protocol as described in Example 21 employing 20C (0.16 g, 0.73 mmol) and 6B (0.19 g, 0.80 mmol) as starting materials afforded 0.24 g (83%) of 22 as a solid. ¹H NMR (400 MHz, CDCl₃): δ 2.22 (s, 6H), 2.35 (s, 3H), 2.44, (s, 3H), 3.31 (s, 2H), 4.28-4.36 (m, 1H), 4.59-4.68 (m, 1H), 4.70-4.78 (m, 1H), 5.00-5.16 (m, 2H), 6.54 (d, 1H), 6.60 (s, 1H), 7.16 (d, 1H), 7.33 (d, 2H), 8.04 (d, 2H), MS (APCI+) m/z 407 [M+H]⁺, LC purity: 98%.

Example 23

1-(4-(4-(1-(5-Phenyl-1,3,4-oxadiazole-2-carbonyl) azetidin-3-yloxy)benzyl)piperazin-1-yl)ethanone

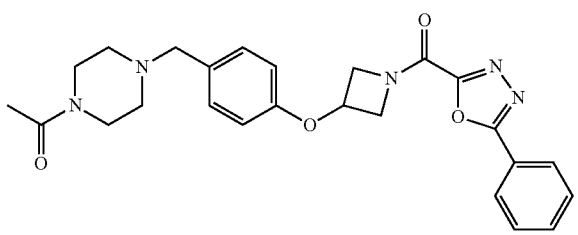 [SMILES: CC(=O)N1CCN(Cc2ccc(OC3CN(C(=O)c4nnc(-c5ccccc5)o4)C3)cc2)CC1]

23A. tert-butyl 3-(4-((4-acetylpiperazin-1-yl)methyl) phenoxy)azetidine-1-carboxylate

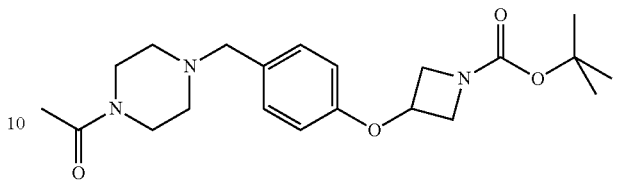

In a microwave vial, 4-[(4-acetylpiperazin-1-yl)methyl] phenol (1.0 g, 4.3 mmol)—see EP 50298—, tert-butyl 3-[(methylsulfonyl)oxy]azetidine-1-carboxylate (1.0 g, 4.0 mmol) and Cs₂CO₃ (1.5 g, 4.6 mmol) together with DMF (10 mL) was added. The mixture was heated in a microwave oven at 140° C. for 60 minutes. Water (40 mL) was added and the suspension was extracted with twice with EtOAc (50 mL). The combined organic phases were washed with brine, dried (Na₂CO₃) and the solvent was removed by evaporation. The residue was co-evaporated with toluene. There was obtained 1.5 g (68%) of 23A.

23B. 1-(4-(4-(Azetidin-3-yloxy)benzyl)piperazin-1-yl)ethanone

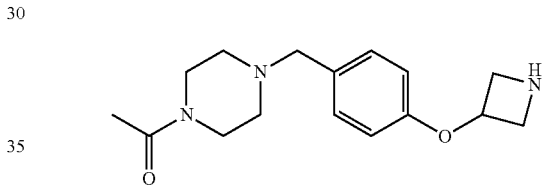

Intermediate 23A (1.5 g, 2.7 mmol) was dissolved in MeOH (20 mL), a 4.0 M solution of HCl in MeOH (2 mL) was added and the reaction mixture was stirred at RT for one hour. The mixture was concentrated and the residue was co-evaporated with EtOH several times. The residue was triturated with THF and then DCM (50 mL) and aqueous K₂CO₃ (5 g dissolved in 5 mL water) were added. After phases were separation, the organic phase was dried (Na₂CO₃) and the solvent was removed by evaporation. There was obtained 0.55 g (71%) of 23B.

23. 1-Acetyl-4-[4-({1-[5-phenyl-1,3,4-oxadiazol-2-yl)carbonyl]azetidin-3-yl}oxy)benzyl]piperazine 23B (0.16 g, 0.53 mmol) and ethyl 5-phenyl-1,3,4-oxadiazole-2-carboxylate (0.11 g, 0.50 mmol) were mixed together in a microwave vial together with toluene (3 mL). The mixture was heated in a microwave oven at 140° C. for 30 min. The solvent was removed by evaporation. The product was purified by preparative chromatography on a Kromasil C8 column eluting with acetonitrile and 0.1 M NH₄OAc. The combined fractions were concentrated and the aqueous solution was pH adjusted to pH 9 with 1M NaOH. The mixture was extracted with EtOAc and the organic layer was dried over Na₂SO₄. The solvent was removed by evaporation. There was obtained 24 mg (10%) of the product as a foam. ¹H NMR (400 MHz, CDCl₃): δ 2.08 (s, 3H), 2.32-2.47 (m, 4H), 3.37-3.54 (m, 4H), 3.62 (s, 2H), 4.29-4.40 (m, 1H), 4.59-4.70 (m, 1H), 4.71-4.82 (m, 1H), 5.02-5.19 (m, 2H), 6.74 (d, 2H), 7.26 (d, 2H), 7.49-7.64 (m, 3H), 8.16 (d, 2H), MS (APCI+) m/z 462 [M+H]+, LC purity: 93%.

Example 24

1-(4-(4-(1-(5-(4-Methoxyphenyl)-1,3,4-oxadiazole-2-carbonyl)azetidin-3-yloxy)benzyl)piperazin-1-yl)ethanone

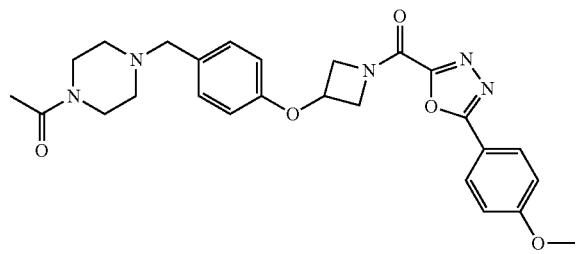 [SMILES: COc1ccc(-c2nnc(C(=O)N3CC(Oc4ccc(CN5CCN(C(C)=O)CC5)cc4)C3)o2)cc1]

Using a similar protocol as described in Example 23 employing 23B (0.16 g, 0.53 mmol) and ethyl 5-(4-methoxyphenyl)-1,3,4-oxadiazole-2-carboxylate (0.12 g, 0.50 mmol) as starting materials afforded 62 mg (24%) of 24 as a foam. ¹H NMR (400 MHz, CDCl₃): δ 2.08 (s, 3H), 2.36-2.45 (m, 4H), 3.40-3.51 (m, 4H), 3.57-3.56 (m, 2H), 3.89 (s, 3H), 4.29-4.37 (m, 1H), 4.59-4.69 (m, 1H), 4.70-4.79 (m, 1H), 5.02-5.16 (m, 2H), 6.74 (d, 2H), 7.02 (d, 2H), 7.25 (d, 2H), 8.10 (d, 2H), MS (APCI+) m/z 492 [M+H]+, LC purity: 99%.

Example 25

1-(4-(4-(1-(5-(4-Chlorophenyl)-1,3,4-oxadiazole-2-carbonyl)azetidin-3-yloxy)benzyl)piperazin-1-yl)ethanone

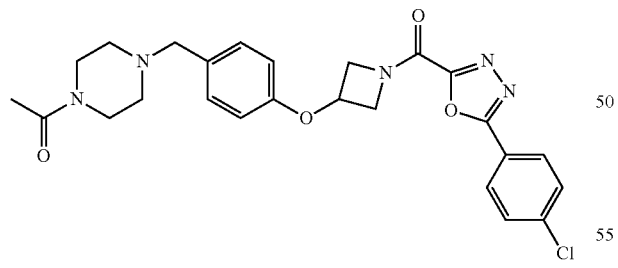

Using a similar protocol as described in Example 23 employing 23B (0.16 g, 0.53 mmol) and ethyl 5-(4-chlorophenyl)-1,3,4-oxadiazole-2-carboxylate (0.12 g, 0.50 mmol) as starting materials afforded 7 mg (3%) of 25 as a foam. ¹H NMR (400 MHz, CDCl₃): δ 1.95 (s, 3H), 2.19-2.36 (m, 4H), 3.24-3.41 (m, 4H), 3.47 (s, 2H), 4.13-4.25 (m, 1H), 4.47-4.67 (m, 2H), 4.91-5.06 (m, 2H), 6.62 (d, 2H), 7.13 (d, 2H), 7.40 (d, 2H), 7.97 (d, 2H), LC purity: 95%.

Example 26

(3-(4-((Dimethylamino)methyl)-3-fluorophenoxy)azetidin-1-yl)(5-phenyl-1,3,4-oxadiazol-2-yl)methanone

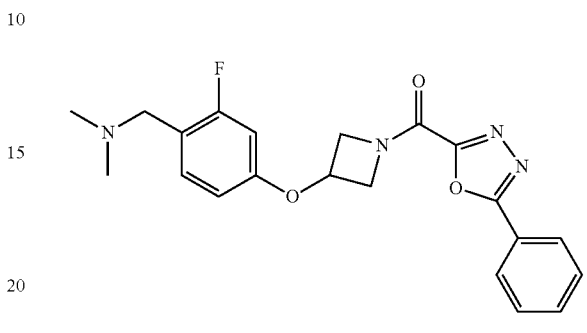

26A. 4-((Dimethylamino)methyl)-3-fluorophenol

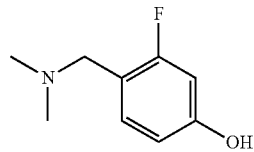

2-Fluoro-4-hydroxybenzaldehyde (3.0 g, 21 mmol) was dissolved in dichloroethane (80 mL). The mixture was cooled by an ice-bath and dimethylamine was bubbled through the solution for 20 minutes. The solution was stirred at 0° C. for 30 minutes. Sodium triacetoxyborohydride (5.4 g, 26 mmol) was added in portions and the reaction mixture was stirred at rt over night. Water (50 mL) was added to the reaction, the slurry was transferred to a reparatory funnel and the aqueous phase was basified to pH=10 with 0.5 M NaOH. The phases were difficult to separate and thus some MeOH and brine were added. The aqueous phase was extracted several times with DCM and the combined organic phases were filtered through a phase separator and the solvent was removed by evaporation. There was obtained 2.5 g (70%) of 26A as a solid. ¹H NMR (500 MHz, CDCl₃): δ 2.33 (s, 6H), 3.49 (s, 2H), 6.32-6.40 (m, 2H), 7.00-7.07 (m, 1H).

26B. tert-Butyl 3-(4-((dimethylamino)methyl)-3-fluorophenoxy)azetidine-1-carboxylate

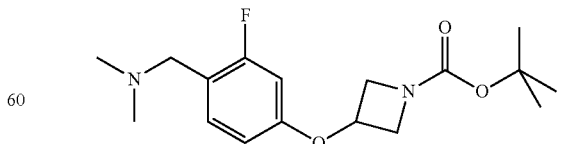

A mixture of NaH (55-65% disp. in oil, 0.31 g, 7.7 mmol) in dry DMF (10 mL) under nitrogen was cooled by an ice-bath. A solution of 26A (1.0 g, 5.9 mmol) in DMF (10 mL) was added drop-wise over 10 minutes. The mixture was stirred for 30 minutes and then tert-butyl 3-[(methylsulfonyl)oxy]azetidine-1-carboxylate (1.63 g, 6.5 mmol) in DMF (10 mL) was added. The mixture was heated to 80° C. over night and then cooled to RT. Water (100 mL) was added and the mixture was extracted three times with EtOAc (50 mL). The combined organic phases were filtered through a phase separator and the solvent was removed by evaporation. The residue was purified by preparative chromatography on a Kromasil C8 column (10 µm 250×20 ID mm) using a gradient of 10-50% acetonitrile in water/acetonitrile/formic acid (95/5/0.2), 100 mL/min. Fractions were collected, pooled and concentrated in vacuo. DCM was added and the solution was filtered through a phase separator and concentrated by evaporation. There was obtained 1.2 g (55%) of 26B as a solid. $^1$H NMR (500 MHz, CDCl$_3$): δ 1.45 (s, 9H), 2.58 (s, 6H), 3.90 (s, 2H), 3.95-4.05 (m, 2H), 4.25-4.35 (m, 2H), 4.81-4.92 (m, 1H), 6.45-6.65 (m, 2H), 7.35-7.45 (m, 1H), 8.42 (s, 1H).

26C. 1-(4-(Azetidin-3-yloxy)-2-fluorophenyl)-N,N-dimethylmethanamine

Intermediate 26B (1.2 g, 3.7 mmol) was dissolved in a 4.0 M solution of HCl in MeOH (20 mL) and the reaction mixture was stirred at RT over for four hours. The mixture was concentrated and the residue was dissolved in water. The aqueous solution was basified to pH=10 with aqueous NaOH (1.0 M) and extracted with DCM (4×30 mL). The combined organic phases were filtered through a phase separator and the solvent was removed by evaporation. There was obtained 0.71 g (86%) of 26C as a colorless oil. $^1$H NMR (500 MHz, CDCl$_3$): δ 2.24 (s, 6H), 3.41 (s, 2H), 3.73-3.83 (m, 2H), 3.87-3.97 (m, 2H), 4.90-5.02 (m, 1H), 6.41-6.55 (m, 2H), 7.16-7.24 (m, 1H).

26. 1-[2-Fluoro-4-({1-[5-phenyl-1,3,4-oxadiazol-2-yl)carbonyl]azetidin-3-yl}oxy)phenyl]-N,N-dimethylmethanamine Using a similar protocol as described in Example 16 employing 26B (0.20 g, 0.90 mmol) and ethyl 5-phenyl-1,3,4-oxadiazole-2-carboxylate (0.21 g, 0.96 mmol) as starting materials afforded 0.30 g (86%) of 26 as a solid. $^1$H NMR (500 MHz, CDCl$_3$): δ 2.25 (s, 6H), 3.44 (s, 2H), 4.29-4.37 (m, 1H), 4.61-4.70 (m, 1H), 4.72-4.80 (m, 1H), 5.02-5.18 (m, 2H), 6.47-6.57 (m, 2H), 7.23-7.31 (m, 2H), 7.49-7.63 (m, 3H), 8.16 (d, 2H), MS (APCI+) m/z 397 [M+H]$^+$, LC purity: 98%.

Example 27

(3-(4-((Dimethylamino)methyl)-3-fluorophenoxy)azetidin-1-yl)(5-(4-methoxyphenyl)-1,3,4-oxadiazol-2-yl)methanone

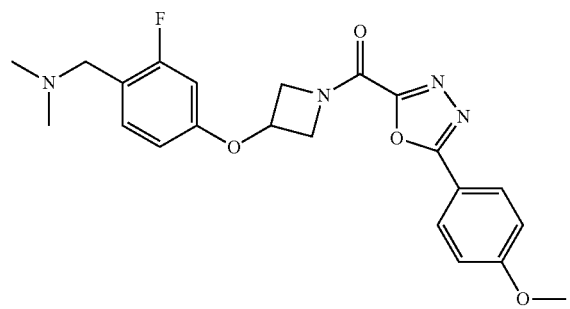

Using a similar protocol as described in Example 16 employing 26B (0.18 g, 0.79 mmol) and ethyl 5-(4-methoxyphenyl)-1,3,4-oxadiazole-2-carboxylate (0.22 g, 0.87 mmol) as starting materials afforded 0.12 g (37%) of 27 as a solid. $^1$H NMR (500 MHz, CDCl$_3$): δ 2.25 (s, 6H), 3.44 (s, 2H), 3.89 (s, 3H), 4.28-4.36 (m, 1H), 4.60-4.69 (m, 1H), 4.71-4.79 (m, 1H), 5.01-5.17 (m, 2H), 6.47-6.58 (m, 2H), 7.02 (d, 2H), 7.23-7.31 (m, 2H), 8.10 (d, 2H), MS (APCI+) m/z 427 [M+H]$^+$, LC purity: 99%.

Example 28

(3-(4-((Dimethylamino)methyl)-3-fluorophenoxy)azetidin-1-yl)(5-p-tolyl-1,3,4-oxadiazol-2-yl)methanone

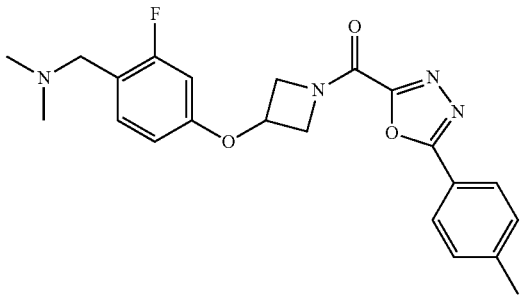

Using a similar protocol as described in Example 16 employing 26B (0.20 g, 0.87 mmol) and 6B (0.22 g, 0.96 mmol) as starting materials afforded 0.10 g (29%) of 28 as a solid. $^1$H NMR (500 MHz, CDCl$_3$): δ 2.26 (s, 6H), 2.45 (s, 3H), 3.44 (s, 2H), 4.28-4.36 (m, 1H), 4.61-4.69 (m, 1H), 4.72-4.80 (m, 1H), 5.01-5.17 (m, 2H), 6.47-6.58 (m, 2H), 7.22-7.30 (m, 2H), 7.31-7.37 (m, 2H), 8.05 (d, 2H), MS (APCI+) m/z 411 [M+H]+, LC purity: 98%.

Example 29

(3-(3-Fluoro-4-((4-methylpiperazin-1-yl)methyl)phenoxy)azetidin-1-yl)(5-phenyl-1,3,4-oxadiazol-2-yl)methanone

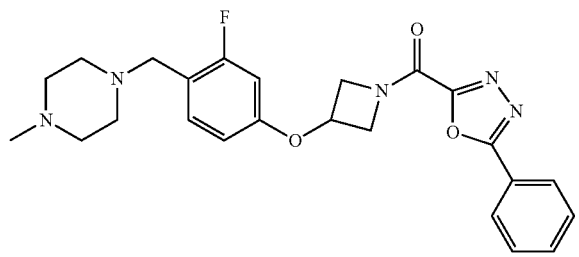 [SMILES: CN1CCN(Cc2ccc(OC3CN(C(=O)c4nnc(-c5ccccc5)o4)C3)cc2F)CC1]

29A.
1-(2-fluoro-4-methoxybenzyl)-4-methylpiperazine

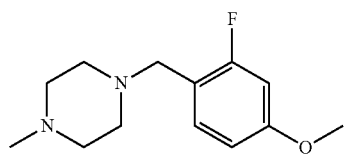

2-Fluoro-4-methoxybenzaldehyde (6.0 g, 39 mmol) was dissolved in dichloroethane (100 mL) and 1-methylpiperazine (4.5 g, 45 mmol) was added and the solution was stirred at rt for 30 minutes. Sodium triacetoxyborohydride (10 g, 47 mmol) was added in portions and the reaction mixture was stirred at rt over night. Aqueous $Na_2CO_3$ (sat.) was added to the reaction and the phases were separated. The aqueous phase were extracted twice with DCM and the combined organic phases were filtered through a phase separator and the solvent was removed by evaporation. There was obtained 9.3 g (100%) of 29A as a brown oil. $^1$H NMR (500 MHz, CDCl$_3$): δ 2.28 (s, 3H), 2.30-2.70 (bm, 8H), 3.53 (s, 2H), 3.78 (s, 3H), 6.53-6.71 (m, 2H), 7.17-7.27 (m, 1H).

29B.
3-Fluoro-4-((4-methylpiperazin-1-yl)methyl)phenol

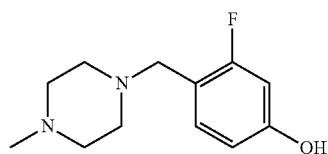 [SMILES: CN1CCN(Cc2ccc(O)cc2F)CC1]

29A (3.1 g, 13 mmol) was dissolved in HBr (conc., 25 mL) and the mixture was refluxed for 5 hours. Solid $Na_2CO_3$ was added to neutralize the mixture which then was extracted with EtOAc. The organic phase was dried (MgSO$_4$) and the solvent was evaporated to give 0.7 g residue. Solid NaCl was added to the aqueous phase which was further extracted with THF. The organic phases were combined and the solvent was removed by evaporation to give 2.7 g of a brown semi-solid. A mixture of THF/EtOAc was added and the product crystallized and was filtered off. There was obtained 1.3 g (45%) of 29B. $^1$H NMR (500 MHz, CDCl$_3$): δ 2.48 (s, 3H), 3.00-3.70 (bm, 8H), 3.43 (s, 2H), 6.48-6.61 (m, 2H), 7.08-7.17 (m, 1H).

29C. tert-Butyl 3-(3-fluoro-4-((4-methylpiperazin-1-yl)methyl)phenoxy)azetidine-1-carboxylate

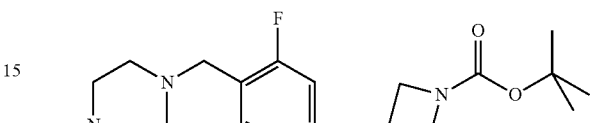

A mixture of NaH (55-65% disp. in oil, 0.50 g, 11.5 mmol) in dry DMF (10 mL) under nitrogen was cooled by an ice-bath. A solution of 29B (1.3 g, 5.8 mmol) in DMF (25 mL) was added drop-wise over 10 minutes. The mixture was stirred for 20 minutes and then tert-butyl 3-[(methylsulfonyl)oxy]azetidine-1-carboxylate (1.7 g, 6.9 mmol) in DMF (15 mL) was added. The mixture was heated to 80° C. for six days and then cooled to RT. Water and some aqueous NaOH was added and the mixture was extracted three times with EtOAc. The combined organic solutions were dried (MgSO$_4$) and evaporated. The residue was purified by column chromatography on SiO$_2$ using 5% triethylamine in EtOAc as eluent. There was obtained 0.98 g (45%) of 29C as a colorless oil. $^1$H NMR (500 MHz, CDCl$_3$): δ 1.45 (s, 9H), 2.28 (s, 3H), 2.28-2.72 (bm, 8H), 3.52 (s, 2H), 3.91-4.03 (m, 2H), 4.22-4.33 (m, 2H), 4.76-4.89 (m, 1H), 6.39-6.52 (m, 2H), 7.19-7.28 (m, 1H).

29D. 1-(4-(Azetidin-3-yloxy)-2-fluorobenzyl)-4-methylpiperazine

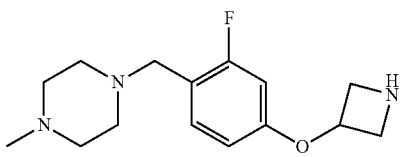 [SMILES: CN1CCN(Cc2ccc(OC3CNC3)cc2F)CC1]

A solution of 29C (0.9 g, 2.4 mmol) in DCM (20 mL) was treated with TFA (10 g, 88 mmol) and stirred at 0° C. for 4 h. The reaction mixture was concentrated and the residue was dissolved in aqueous NaHCO$_3$ (sat.). The mixture was extracted three times with DCM and the organic solutions were filtered through a phase separator. The solvent was removed by evaporation. There was obtained 0.21 g (32%) of 29D as a colorless oil. $^1$H NMR (500 MHz, CDCl$_3$): δ 2.28 (s, 3H), 2.28-2.68 (bm, 8H), 3.52 (s, 2H), 3.69-3.85 (m, 2H), 3.85-4.02 (m, 2H), 4.88-5.03 (m, 1H), 6.36-6.58 (m, 2H), 7.15-7.27 (m, 1H).

29. 1-[2-Fluoro-4-({1-[(5-phenyl-1,3,4-oxadiazol-2-yl)carbonyl]azetidin-3-yl}oxy)benzyl]-4-methylpiperazine Using a similar protocol as described in Example 10 employing 29D (0.10 g, 0.36 mmol) and ethyl 5-phenyl-1,3, 4-oxadiazole-2-carboxylate (0.10 g, 0.46 mmol) as starting materials afforded 67 mg (41%) of 29 as a foam. $^1$H NMR (500 MHz, DMSO-$d_6$): δ 2.10 (s, 3H), 2.12-2.50 (bm, 8H), 3.43 (s, 2H), 4.05-4.16 (m, 1H), 4.50-4.70 (m, 2H), 5.03-5.23 (m, 2H), 6.68-6.84 (m, 2H), 7.25-7.37 (m, 1H), 7.57-7.75 (m, 3H), 8.00-8.13 (m, 2H), MS (APCI+) m/z 452 [M+H]$^+$, LC purity: 97%.

Example 30

(3-(3-Fluoro-4-((4-methylpiperazin-1-yl)methyl) phenoxy)azetidin-1-yl)(5-(4-methoxyphenyl)-1,3,4-oxadiazol-2-yl)methanone Using a similar protocol as described in Example 10 employing 29D (0.10 g, 0.36 mmol) and ethyl 5-(4-methoxyphenyl)-1,3,4-oxadiazole-2-carboxylate (0.11 g, 0.43 mmol) as starting materials afforded 52 mg (30%) of 29 as a foam.

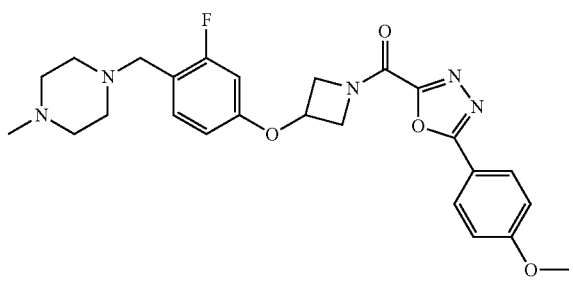

$^1$H NMR (500 MHz, MeOD): δ 2.27 (s, 3H), 2.20-2.70 (bm, 8H), 3.56 (s, 2H), 3.90 (s, 3H), 4.16-4.27 (m, 1H), 4.63-4.75 (m, 2H), 5.08-5.26 (m, 2H), 6.62-6.77 (m, 2H), 7.12 (d, 2H), 7.30-7.40 (m, 1H), 8.08 (d, 2H), MS (APCI+) m/z 482 [M+H]$^+$, LC purity: 97%.

Example 31

(3-(3-Fluoro-4-(pyrrolidin-1-ylmethyl)phenoxy)azetidin-1-yl)(5-phenyl-1,3,4-oxadiazol-2-yl)methanone

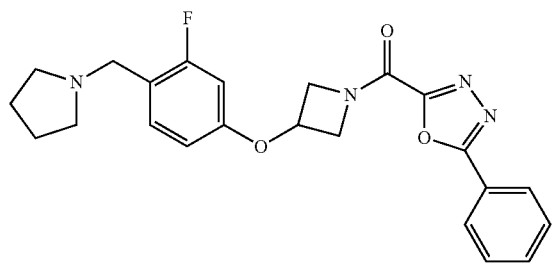 [SMILES: O=C(c1nnc(-c2ccccc2)o1)N1CC(Oc2ccc(CN3CCCC3)c(F)c2)C1]

31A. 3-Fluoro-4-(pyrrolidin-1-ylmethyl)phenol

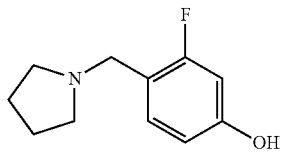 [SMILES: Oc1ccc(CN2CCCC2)c(F)c1]

To a solution of 2-fluoro-4-hydroxybenzaldehyde (0.42 g, 3.00 mmol) in DCM (15 mL) was added pyrrolidine (0.26 g, 3.60 mmol). After stirring for 20 min, sodium triacetoxyborohydride (0.76 g, 3.60 mmol) was added and the reaction mixture was stirred overnight. The mixture was then diluted with DCM and transferred to a separatory funnel. Water was added, basified to pH 9-10 with a 0.1 M solution of NaOH and extracted 6 times with DCM. The organic layer was dried (phase separator) and concentrated in vacuo. There was obtained 0.55 g (94%) of 31A as a solid. $^1$H NMR (500 MHz, CDCl$_3$): δ 1.85 (s, 4H), 2.70 (s, 4H), 3.60 (s, 2H), 6.25 (m, 2H), 7.00 (m, 1H).

31B. tert-Butyl 3-(3-fluoro-4-(pyrrolidin-1-ylmethyl) phenoxy)azetidine-1-carboxylate

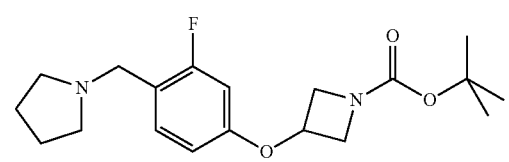 [SMILES: CC(C)(C)OC(=O)N1CC(Oc2ccc(CN3CCCC3)c(F)c2)C1]

Using a similar protocol as described in Example 29C employing 31A (6.6 g, 33.8 mmol) and tert-butyl 3-(methylsulfonyloxy)azetidine-1-carboxylate (10.2 g, 40.6 mmol) as starting materials afforded 9.4 g (80%) of 31B as a solid. $^1$H NMR (500 MHz, CDCl$_3$): δ 1.45 (s, 9H), 1.77 (m, 4H), 2.52 (m, 4H), 3.61 (s, 2H), 3.99 (m, 2H), 4.27 (m, 2H), 4.84 (m, 1H), 6.43 (dd, 1H), 6.49 (dd, 1H), 7.27 (t, 1H), MS (APCI+) m/z 351 [M+H]$^+$.

31C. 1-(4-(Azetidin-3-yloxy)-2-fluorobenzyl)pyrrolidine

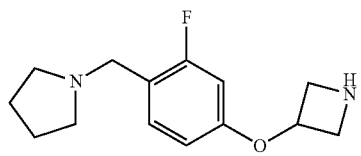 [SMILES: Fc1cc(OC2CNC2)ccc1CN1CCCC1]

Using a similar protocol as described in Example 29D employing 31B (9.44 g, 26.9 mmol) as starting material afforded 6.05 g (90%) of 31C as an oil. $^1$H NMR (500 MHz, CDCl$_3$): δ 1.77 (m, 4H), 2.52 (m, 4H), 3.61 (s, 2H), 3.77 (m, 2H), 3.91 (m, 2H), 4.95 (m, 1H), 6.45 (m, 1H), 6.52 (m, 1H), 7.25 (m, 1H), MS (APCI+) m/z 251 [M+H]$^+$.

31. (3-(3-Fluoro-4-(pyrrolidin-1-ylmethyl)phenoxy) azetidin-1-yl)(5-phenyl-1,3,4-oxadiazol-2-yl)methanone Using a similar protocol as described in Example 16 employing 31C (0.11 g, 0.44 mmol) and ethyl 5-phenyl-1,3, 4-oxadiazole-2-carboxylate (0.10 g, 0.48 mmol) as starting materials afforded 130 mg (71%) of 31 as a solid. $^1$H NMR (500 MHz, CDCl$_3$): δ 1.80 (s, 4H), 2.50 (s, 4H), 3.65 (s, 2H), 4.30 (m, 1H), 4.65 (m, 1H), 4.75 (m, 1H), 5.05 (m, 1H), 5.15 (m, 1H), 6.50 (m, 2H), 7.30 (t, 1H), 7.55 (m, 3H), 8.20 (d, 2H), MS (APCI+) m/z 423 [M+H]$^+$, LC purity: 95%.

Example 32

(3-(3-Fluoro-4-(pyrrolidin-1-ylmethyl)phenoxy)azetidin-1-yl)(5-(4-methoxyphenyl)-1,3,4-oxadiazol-2-yl)methanone

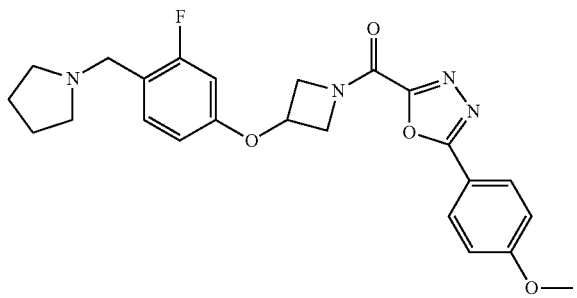 [SMILES: COc1ccc(-c2nnc(C(=O)N3CC(Oc4ccc(CN5CCCC5)c(F)c4)C3)o2)cc1]

Using a similar protocol as described in Example 16 employing 31C (2.10 g, 8.40 mmol) and ethyl 5-(4-methoxyphenyl)-1,3,4-oxadiazole-2-carboxylate (2.30 g, 9.23 mmol) as starting materials afforded 2.90 g (76%) of 32 as a solid. $^1$H NMR (500 MHz, CDCl$_3$): δ 1.78 (s, 4H), 2.54 (s, 4H), 3.63 (s, 2H), 3.89 (s, 3H), 4.32 (dd, 1H), 4.64 (dd, 1H), 4.74 (dd, 1H), 5.05 (m, 1H), 5.12 (dd, 1H), 6.51 (m, 2H), 7.02 (d, 2H), 7.31 (t, 1H), 8.10 (d, 2H), MS (APCI+) m/z 453 [M+H]$^+$, LC purity: 96%.

Example 33

(3-(4-((Dimethylamino)methyl)phenoxy)azetidin-1-yl)(5-phenyl-1,3,4-oxadiazol-2-yl)methanone

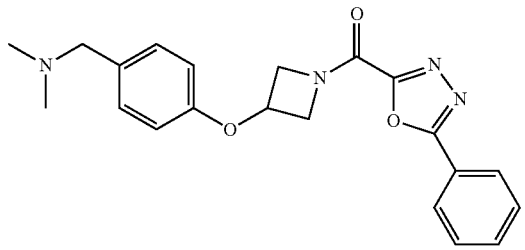 [SMILES: CN(C)Cc1ccc(OC2CN(C(=O)c3nnc(-c4ccccc4)o3)C2)cc1]

33A. tert-Butyl 3-(4-((dimethylamino)methyl)phenoxy)azetidine-1-carboxylate

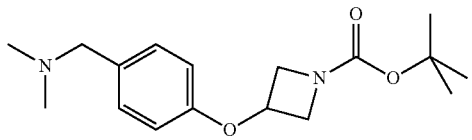 [SMILES: CN(C)Cc1ccc(OC2CN(C(=O)OC(C)(C)C)C2)cc1]

Using a similar protocol as described in Example 29C employing 4-((dimethylamino)methyl)phenol (8.4 g, 55.5 mmol) and tert-butyl 3-(methylsulfonyloxy)azetidine-1-carboxylate (16.8 g, 66.7 mmol) as starting materials afforded 14.8 g (75%) of 33A as an oil. $^1$H NMR (500 MHz, CDCl$_3$): δ 1.40 (s, 9H), 2.55 (s, 6H), 3.90 (s, 2H), 4.00 (m, 2H), 4.30 (m, 2H), 4.85 (m, 1H), 6.75 (d, 2H), 7.35 (d, 2H), MS (APCI+) m/z 307 [M+H]$^+$.

33B. 1-(4-(Azetidin-3-yloxy)phenyl)-N,N-dimethylmethanamine

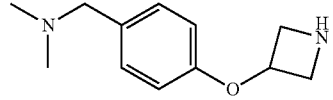

Using a similar protocol as described in Example 29D employing 33A (0.14 g, 0.51 mmol) as starting material afforded 0.10 g (95%) of 33B as an oil. MS (APCI+) m/z 207 [M+H]$^+$.

33. (3-(4-((Dimethylamino)methyl)phenoxy)azetidin-1-yl)(5-phenyl-1,3,4-oxadiazol-2-yl)methanone Using a similar protocol as described in Example 16 employing 33B (0.10 g, 0.48 mmol) and ethyl 5-phenyl-1,3,4-oxadiazole-2-carboxylate (0.12 g, 0.53 mmol) as starting materials afforded 69 mg (38%) of 33 as a solid. $^1$H NMR (500 MHz, CDCl$_3$): δ 2.24 (s, 6H), 3.37 (s, 2H), 4.34 (dd, 1H), 4.65 (dd, 1H), 4.77 (dd, 1H), 5.10 (m, 2H), 6.74 (d, 2H), 7.24 (m, 2H), 7.55 (m, 3H), 8.15 (d, 2H), MS (APCI+) m/z 379 [M+H]$^+$, LC purity: 95%.

Example 34

(3-(4-((Dimethylamino)methyl)phenoxy)azetidin-1-yl)(5-(4-(methylthio)phenyl)-1,3,4-oxadiazol-2-yl)methanone

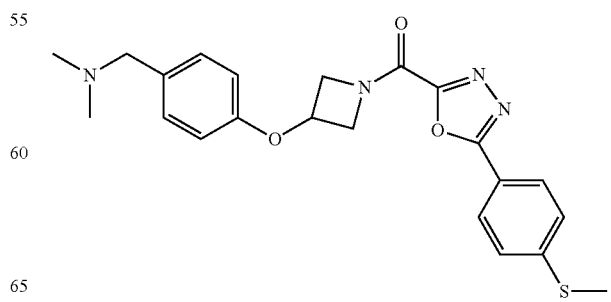

Using a similar protocol as described in Example 16 employing 33B (0.12 g, 0.58 mmol) and ethyl 5-(4-(methylthio)phenyl)-1,3,4-oxadiazole-2-carboxylate—see e.g. WO93/13083—(0.17 g, 0.64 mmol) as starting materials afforded 81 mg (33%) of 34 as a solid. $^1$H NMR (500 MHz, CDCl$_3$): δ 2.22 (s, 6H), 2.53 (s, 3H), 3.36 (s, 2H), 4.32 (dd, 1H), 4.63 (dd, 1H), 4.73 (dd, 1H), 5.09 (m, 2H), 6.72 (d, 2H), 7.23 (d, 2H), 7.33 (d, 2H), 8.03 (d, 2H), MS (APCI+) m/z 425 [M+H]$^+$, LC purity: 94%.

Example 35

(3-(4-((dimethylamino)methyl)phenoxy)azetidin-1-yl)(5-(4-(trifluoromethyl)phenyl)-1,3,4-oxadiazol-2-yl)methanone

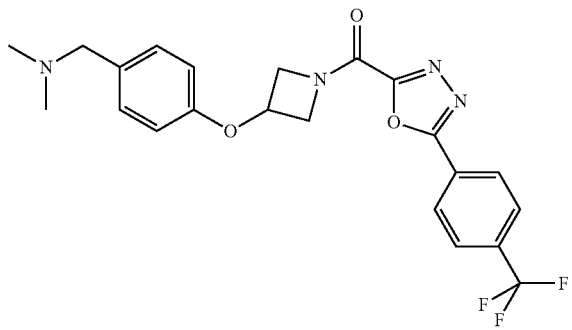 [SMILES: CN(C)Cc1ccc(OC2CN(C(=O)c3nnc(-c4ccc(C(F)(F)F)cc4)o3)C2)cc1]

Using a similar protocol as described in Example 16 employing 33B (0.21 g, 0.75 mmol) and ethyl 5-(4-(trifluoromethyl)phenyl)-1,3,4-oxadiazole-2-carboxylate (0.24 g, 0.84 mmol) as starting materials afforded 150 mg (44%) of 35 as a solid. $^1$H NMR (500 MHz, CD$_3$OD): δ 2.25 (s, 6H), 3.45 (s, 2H), 4.22 (dd, 1H), 4.69 (m, 2H), 5.17 (m, 2H), 6.86 (d, 2H), 7.29 (d, 2H), 7.92 (d, 2H), 8.33 (d, 2H), MS (APCI+) m/z 447 [M+H]$^+$, LC purity: 94%.

Example 36

(5-(4-Chlorophenyl)-1,3,4-oxadiazol-2-yl)(3-(4-((dimethylamino)methyl)phenoxy)azetidin-1-yl)methanone

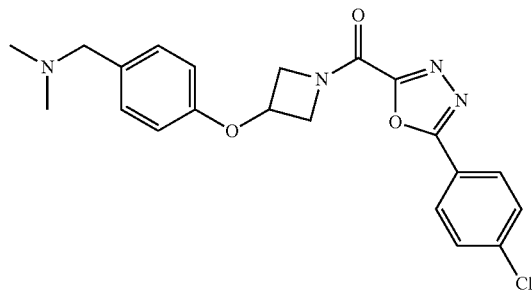 [SMILES: CN(C)Cc1ccc(OC2CN(C(=O)c3nnc(-c4ccc(Cl)cc4)o3)C2)cc1]

Intermediate 33B (0.19 g, 0.92 mmol) was dissolved in DCM (3 mL) and then ethyl 5-(4-chlorophenyl)-1,3,4-oxadiazole-2-carboxylate (0.23 g, 0.92 mmol) was added. Trimethylaluminum (0.51 mL, 2 M in hexane, 1.0 mmol) was added under nitrogen. The reaction mixture was stirred at RT overnight. The mixture was cooled in an ice-bath and carefully quenched with water. The mixture was filtered through celite and washed with water followed by DCM. The filtrates were transferred to a separatory funnel and the organic layer was separated, dried (phase separator) and evaporated. DMSO (5 mL) and ethanol (5 mL) were added and the mixture was filtered. The product was purified using preparative HPLC (gradient: 30-75% acetonitrile over 30 min, 0.2% aqueous ammonium acetate buffer). The product fractions were pooled and evaporated. DCM was added and the solution was dried (phase separator) and concentrated in vacuo. There was obtained 0.23 g (59%) of 36 as a solid. $^1$H NMR (500 MHz, CDCl$_3$): δ 2.29 (s, 6H), 3.44 (s, 2H), 4.34 (dd, 1H), 4.65 (d, 1H), 5.10 (m, 2H), 6.75 (d, 2H), 7.27 (d, 2H), 7.52 (d, 2H), 8.11 (d, 2H), MS (APCI+) m/z 413 [M+H]$^+$, LC purity: 93%.

Example 37

(5-(4-(Difluoromethoxy)phenyl)-1,3,4-oxadiazol-2-yl)(3-(4-((dimethylamino)methyl)phenoxy)azetidin-1-yl)methanone

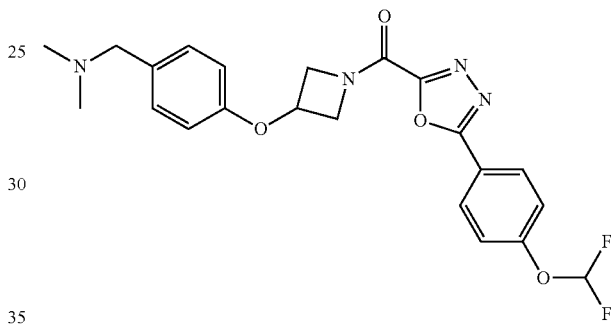

37A. Ethyl 5-(4-(difluoromethoxy)phenyl)-1,3,4-oxadiazole-2-carboxylate

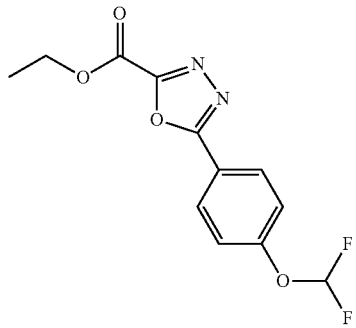 [SMILES: CCOC(=O)c1nnc(-c2ccc(OC(F)F)cc2)o1]

Using similar protocols as described in Example 6A and Example 6B employing 4-difluoromethoxy benzoic acid hydrazide (2.0 g, 10 mmol) as starting material afforded 2.5 g (89%) of 37A as a solid. $^1$H NMR (500 MHz, CDCl$_3$): δ 1.49 (t, 3H), 4.55 (m, 2H), 6.60 (t, 1H), 7.27 (d, 2H), 8.19 (d, 2H).

37. (5-(4-(Difluoromethoxy)phenyl)-1,3,4-oxadiazol-2-yl)(3-(4-((dimethylamino)methyl)phenoxy)azetidin-1-yl)methanone Using a similar protocol as described in Example 36 employing 33B (0.19 g, 0.92 mmol) and 37A (0.26 g, 0.92 mmol) as starting materials afforded 62 mg (15%) of 37 as a solid. $^1$H NMR (500 MHz, CDCl$_3$): δ 2.27 (s, 6H), 3.44 (s, 2H), 4.35 (dd, 1H), 4.66 (dd, 1H), 4.77 (dd, 1H), 5.10 (m, 2H), 6.62 (t, 1H), 6.75 (d, 2H), 7.28 (m, 4H), 8.19 (d, 2H), MS (APCI+) m/z 445 [M+H]$^+$, LC purity: 94%.

Example 38

(3-(4-((Dimethylamino)methyl)phenoxy)azetidin-1-yl)(5-(4-methoxyphenyl)-1,3,4-oxadiazol-2-yl)methanone

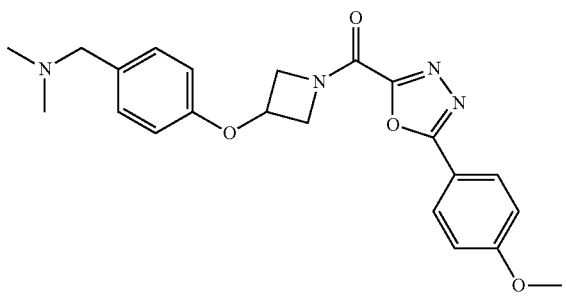

Using a similar protocol as described in Example 16 employing 33B (0.15 g, 0.73 mmol) and ethyl 5-(4-methoxyphenyl)-1,3,4-oxadiazole-2-carboxylate (0.18 g, 0.73 mmol) as starting materials afforded 180 mg (61%) of 38 as a solid. $^1$H NMR (500 MHz, CD$_3$OD): δ 2.23 (s, 6H), 3.37 (s, 2H), 3.90 (s, 3H), 4.33 (dd, 1H), 4.63 (m, 1H), 4.76 (dd, 1H), 5.10 (m, 2H), 6.74 (d, 2H), 7.02 (d, 2H), 7.24 (d, 2H), 8.10 (d, 2H), MS (APCI+) m/z 409 [M+H]$^+$, LC purity: 92%.

Example 39

(3-(4-((Dimethylamino)methyl)-2,3-difluorophenoxy)azetidin-1-yl)(5-phenyl-1,3,4-oxadiazol-2-yl)methanone

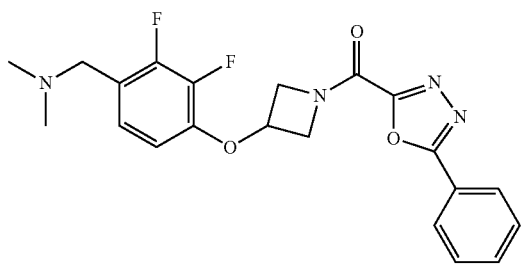 [SMILES: CN(C)Cc1ccc(OC2CN(C(=O)c3nnc(-c4ccccc4)o3)C2)c(F)c1F]

39A. 1-(4-(azetidin-3-yloxy)-2,3-difluorophenyl)-N,N-dimethylmethanamine dihydrochloride

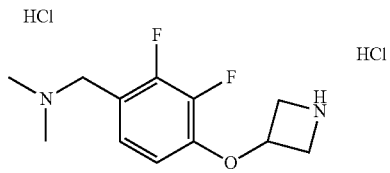 [SMILES: Cl ; CN(C)Cc1ccc(OC2CNC2)c(F)c1F ; Cl]

Using similar protocols as described in Examples 20A, 20B and 20C employing 2,3-difluoro-4-hydroxybenzaldehyde and dimethylamine as starting material afforded 0.67 g (69%) of 39A as a solid. $^1$H NMR (500 MHz, DMSO-d$_6$): δ 2.69 (s, 6H), 4.04 (m, 2H), 4.28 (s, 2H), 4.45 (m, 2H), 5.20 (m, 1H), 6.97 (t, 1H), 7.52 (t, 1H), 9.53 (b, 1H), 9.59 (b, 1H), 11.05 (b, 1H), MS (APCI+) m/z 243 [M+H]$^+$.

39. (3-(4-((Dimethylamino)methyl)-2,3-difluorophenoxy)azetidin-1-yl)(5-phenyl-1,3,4-oxadiazol-2-yl)methanone Using a similar protocol as described in Example 36 employing 39A (0.32 g, 1.00 mmol) and ethyl 5-phenyl-1,3,4-oxadiazole-2-carboxylate (0.24 g, 1.10 mmol) as starting materials afforded 65 mg (15%) of 39 as a solid. $^1$H NMR (500 MHz, CDCl$_3$): δ 2.27 (s, 6H), 3.46 (s, 2H), 4.39 (dd, 1H), 4.65 (dd, 1H), 4.82 (m, 1H), 5.13 (m, 2H), 6.52 (t, 1H), 7.04 (t, 1H), 7.54 (t, 2H), 7.60 (t, 1H), 8.16 (d, 2H), MS (APCI+) m/z 415 [M+H]$^+$, LC purity: 89%.

Example 40

(3-(4-((Dimethylamino)methyl)-2,3-difluorophenoxy)azetidin-1-yl)(5-(4-methoxyphenyl)-1,3,4-oxadiazol-2-yl)methanone

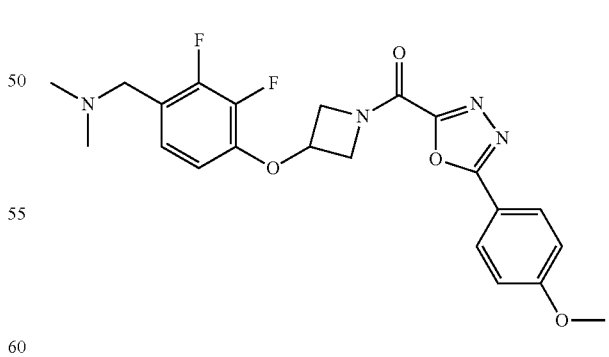

Using a similar protocol as described in Example 36 employing 39A (0.18 g, 0.57 mmol) and ethyl 5-(4-methoxyphenyl)-1,3,4-oxadiazole-2-carboxylate (0.19 g, 0.77 mmol) as starting materials afforded 170 mg (69%) of 40 as a solid. $^1$H NMR (500 MHz, CDCl$_3$): δ 2.26 (s, 6H), 3.47 (s, 2H), 3.89 (s, 3H), 4.39 (d, 1H), 4.65 (dd, 1H), 4.81 (m, 1H), 5.13 (m, 2H), 6.51 (t, 1H), 7.02 (m, 3H), 8.09 (d, 2H), MS (APCI+) m/z 445 [M+H]+, LC purity: 94%.

Example 41

(3-(4-(Azetidin-1-ylmethyl)phenoxy)azetidin-1-yl)(5-(4-methoxyphenyl)-1,3,4-oxadiazol-2-yl)methanone

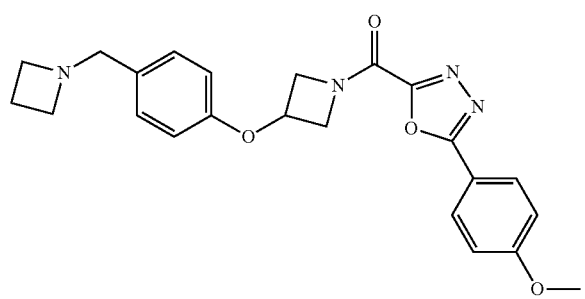 [SMILES: COc1ccc(-c2nnc(C(=O)N3CC(Oc4ccc(CN5CCC5)cc4)C3)o2)cc1]

41A. 1-(4-(Azetidin-3-yloxy)benzyl)azetidine

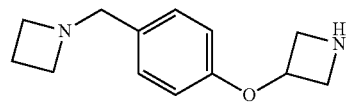 [SMILES: c1cc(OC2CNC2)ccc1CN1CCC1]

Using similar protocols as described in Examples 20A, 20B and 20C employing azetidine and 4-hydroxybenzaldehyde as starting material afforded 0.44 g (39%) of 41A as an oil. ¹H NMR (500 MHz, CDCl₃): δ 2.06 (m, 2H), 3.18 (m, 4H), 3.35 (t, 1H), 3.48 (s, 2H), 3.66 (t, 1H), 3.8-5.0 (m, 3H), 6.71 (m, 2H), 7.16 (d, 2H).

41. (3-(4-(Azetidin-1-ylmethyl)phenoxy)azetidin-1-yl)(5-(4-methoxyphenyl)-1,3,4-oxadiazol-2-yl)methanone Using a similar protocol as described in Example 36 employing 41A (0.10 g, 0.46 mmol) and ethyl 5-(4-methoxyphenyl)-1,3,4-oxadiazole-2-carboxylate (0.13 g, 0.52 mmol) as starting materials afforded 130 mg (68%) of 41 as a solid. ¹H NMR (500 MHz, CDCl₃): δ 2.08 (m, 2H), 3.19 (t, 4H), 3.51 (s, 2H), 3.89 (s, 3H), 4.32 (d, 1H), 4.64 (dd, 1H), 4.74 (d, 1H), 5.06 (m, 1H), 5.11 (m, 1H), 6.72 (d, 2H), 7.02 (d, 2H), 7.21 (d, 2H), 8.10 (d, 2H), MS (APCI+) m/z 421 [M+H]+, LC purity: 95%.

Example 42

(3-(4-(azetidin-1-ylmethyl)phenoxy)azetidin-1-yl)(5-phenyl-1,3,4-oxadiazol-2-yl)methanone

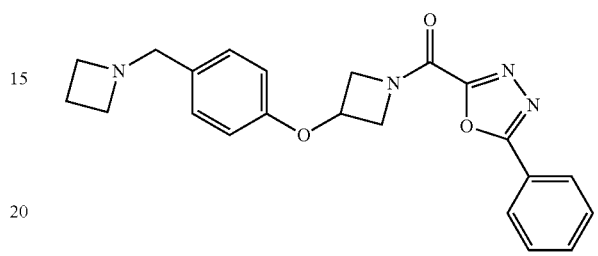

Using a similar protocol as described in Example 36 employing 41A (0.10 g, 0.46 mmol) and ethyl 5-phenyl-1,3,4-oxadiazole-2-carboxylate (0.12 g, 0.55 mmol) as starting materials afforded 135 mg (75%) of 42 as a solid. ¹H NMR (500 MHz, CDCl₃): δ 2.08 (m, 2H), 3.20 (t, 4H), 3.51 (s, 2H), 4.33 (d, 1H), 4.65 (dd, 1H), 4.75 (d, 1H), 5.07 (m, 1H), 5.13 (m, 1H), 6.73 (d, 2H), 7.22 (d, 2H), 7.56 (t, 2H), 7.65 (t, 1H), 8.15 (d, 2H), MS (APCI+) m/z 391 [M+H]+, LC purity: 96%.

Example 43

(5-(4-(Difluoromethoxy)phenyl)-1,3,4-oxadiazol-2-yl)(3-(4-((dimethylamino)methyl)-3-methylphenoxy)azetidin-1-yl)methanone Using a similar protocol as described in Example 36 employing 20C (0.24 g, 1.09 mmol) and 37A (0.31 g, 1.09 mmol) as starting materials afforded 200 mg (40%) of 43 as a solid. ¹H NMR (500 MHz, CDCl₃): δ 2.24 (s, 6H), 2.36 (s, 3H), 3.33 (s, 2H), 4.33 (dd, 1H), 4.65 (dd, 1H), 4.74 (dd, 1H), 5.07 (m, 1H), 5.12 (m, 1H), 6.55 (d, 1H), 6.62 (t, 1H), 7.18 (d, 1H), 7.27 (d, 2H), 8.19 (d, 2H), MS (APCI+) m/z 459 [M+H]⁺, LC purity: 97%.

Example 44

(5-(4-Chlorophenyl)-1,3,4-oxadiazol-2-yl)(3-(4-((dimethylamino)methyl)-3-methylphenoxy)azetidin-1-yl)methanone

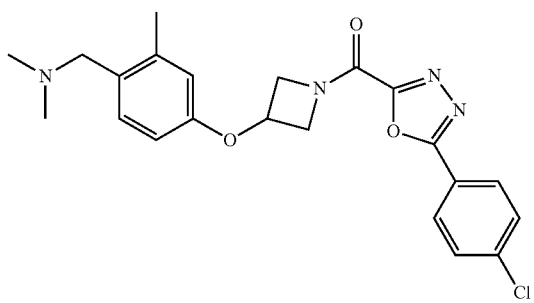 [SMILES: Cc1cc(OC2CN(C(=O)c3nnc(-c4ccc(Cl)cc4)o3)C2)ccc1CN(C)C]

Using a similar protocol as described in Example 36 employing 20C (0.24 g, 1.09 mmol) and 5-(4-chlorophenyl)-1,3,4-oxadiazole-2-carboxylate (0.28 g, 1.11 mmol) as starting materials afforded 320 mg (69%) of 44 as a solid. $^1$H NMR (500 MHz, CDCl₃): δ 2.25 (s, 6H), 2.34 (s, 3H), 3.37 (s, 2H), 4.33 (dd, 1H), 4.65 (dd, 1H), 4.74 (dd, 1H), 5.05 (m, 1H), 5.12 (m, 1H), 6.55 (dd, 1H), 6.60 (d, 1H), 7.17 (d, 1H), 7.52 (d, 2H), 8.10 (d, 2H), MS (APCI+) m/z 427 [M+H]⁺, LC purity: 97%.

Example 45

(5-Phenyl-1,3,4-oxadiazol-2-yl)(3-(4-(pyrrolidin-1-ylmethyl)-3-(trifluoromethyl)phenoxy)azetidin-1-yl)methanone

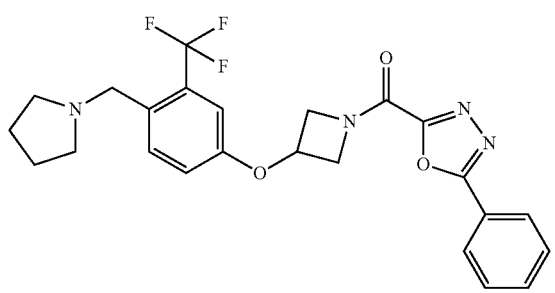 [SMILES: O=C(c1nnc(-c2ccccc2)o1)N1CC(Oc2ccc(CN3CCCC3)c(C(F)(F)F)c2)C1]

45A. 1-(4-(Azetidin-3-yloxy)-2-(trifluoromethyl)benzyl)pyrrolidine

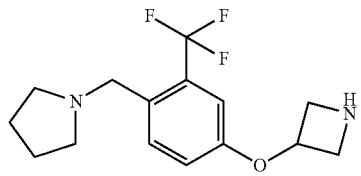 [SMILES: FC(F)(F)c1cc(OC2CNC2)ccc1CN1CCCC1]

Using similar protocols as described in Examples 29A, 29B, 29C and 29D employing pyrrolidine and 4-methoxy-2-(trifluoromethyl)benzaldehyde as starting materials afforded 0.58 g (20%) of 45A as an oil. $^1$H NMR (500 MHz, CDCl₃): δ 1.78 (s, 4H), 2.53 (d, 4H), 3.71 (s, 2H), 3.80 (m, 2H), 3.93 (m, 2H), 5.01 (m, 1H), 6.87 (dd, 1H), 7.00 (d, 1H), 7.64 (d, 1H), MS (APCI+) m/z 301 [M+H]⁺.

45. (5-Phenyl-1,3,4-oxadiazol-2-yl)(3-(4-(pyrrolidin-1-ylmethyl)-3-(trifluoromethyl)phenoxy)azetidin-1-yl)methanone Using a similar protocol as described in Example 16 employing 45A (0.19 g, 0.65 mmol) and ethyl 5-phenyl-1,3,4-oxadiazole-2-carboxylate (0.15 g, 0.71 mmol) as starting materials afforded 230 mg (77%) of 45 as a solid. $^1$H NMR (500 MHz, CDCl₃): δ 1.81 (s, 4H), 2.55 (s, 4H), 3.74 (s, 2H), 4.35 (dd, 1H), 4.67 (dd, 1H), 4.78 (dd, 1H), 5.14 (m, 2H), 6.93 (d, 1H), 7.05 (d, 1H), 7.54 (t, 2H), 7.60 (t, 1H), 7.73 (d, 1H), 8.17 (d, 2H), MS (APCI+) m/z 473 [M+H]⁺, LC purity: 97%.

Example 46

(5-(4-Methoxyphenyl)-1,3,4-oxadiazol-2-yl)(3-(4-(pyrrolidin-1-ylmethyl)-3-(trifluoromethyl)phenoxy)azetidin-1-yl)methanone

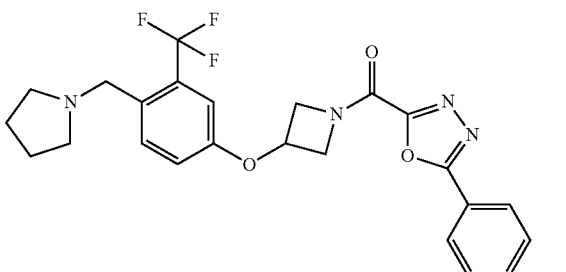

Using a similar protocol as described in Example 16 employing 45A (0.18 g, 0.59 mmol) and ethyl 5-(4-methoxyphenyl)-1,3,4-oxadiazole-2-carboxylate (0.16 g, 0.65 mmol) as starting materials afforded 210 mg (70%) of 46 as a solid. $^1$H NMR (500 MHz, CDCl₃): δ 1.81 (s, 4H), 2.55 (s, 4H), 3.74 (s, 2H), 3.90 (s, 3H), 4.33 (dd, 1H), 4.67 (dd, 1H), 4.76 (dd, 1H), 5.12 (m, 2H), 6.92 (d, 1H), 7.03 (m, 3H), 7.73 (d, 1H), 8.10 (d, 2H), MS (APCI+) m/z 503 [M+H]+, LC purity: 97%.

Example 47

(3-(3-Chloro-4-((dimethylamino)methyl)phenoxy)azetidin-1-yl)(5-(4-methoxyphenyl)-1,3,4-oxadiazol-2-yl)methanone

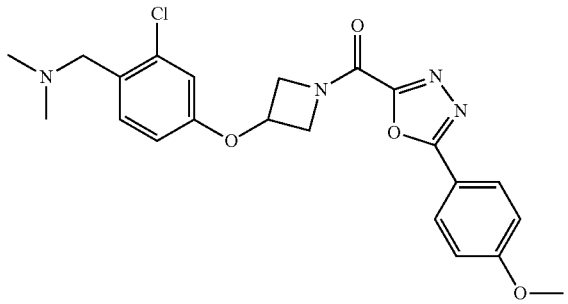

47A. 1-(4-(Azetidin-3-yloxy)-2-chlorophenyl)-N,N-dimethylmethanamine

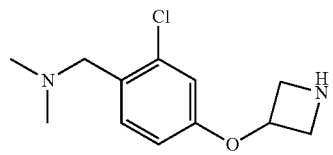 [SMILES: CN(C)Cc1ccc(OC2CNC2)cc1Cl]

Using similar protocols as described in Examples 20A, 20B and 20C employing dimethylamine and 2-chloro-4-hydroxybenzaldehyde as starting material afforded 0.13 g (10%) of 47A as an oil. ¹H NMR (500 MHz, CDCl₃): δ 2.26 (s, 6H), 3.45 (s, 2H), 3.78 (m, 2H), 3.92 (m, 2H), 4.96 (m, 1H), 6.65 (d, 1H), 6.76 (d, 1H), 7.27 (m, 1H).

47. (3-(3-Chloro-4-((dimethylamino)methyl)phenoxy)azetidin-1-yl)(5-(4-methoxyphenyl)-1,3,4-oxadiazol-2-yl)methanone Using a similar protocol as described in Example 16 employing 47A (70 mg, 0.29 mmol) and ethyl 5-(4-methoxyphenyl)-1,3,4-oxadiazole-2-carboxylate (75 mg, 0.30 mmol) as starting materials afforded 105 mg (82%) of 47 as a solid. ¹H NMR (500 MHz, CDCl₃): δ 2.20 (s, 6H), 3.48 (s, 2H), 3.90 (s, 3H), 4.32 (dd, 1H), 4.65 (dd, 1H), 4.74 (dd, 1H), 5.06 (m, 1H), 5.13 (dd, 1H), 6.68 (dd, 1H), 6.80 (d, 1H), 7.02 (d, 2H), 7.35 (d, 1H), 8.10 (d, 2H), MS (APCI+) m/z 443 [M+H]+, LC purity: 91%.

Example 48

(3-(3-Chloro-4-((dimethylamino)methyl)phenoxy)azetidin-1-yl)(5-phenyl-1,3,4-oxadiazol-2-yl)methanone

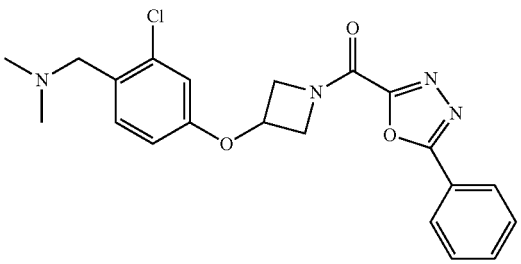 [SMILES: CN(C)Cc1ccc(OC2CN(C(=O)c3nnc(-c4ccccc4)o3)C2)cc1Cl]

Using a similar protocol as described in Example 16 employing 47A (70 mg, 0.29 mmol) and ethyl 5-phenyl-1,3,4-oxadiazole-2-carboxylate (70 mg, 0.32 mmol) as starting materials afforded 70 mg (58%) of 48 as a solid. ¹H NMR (500 MHz, CDCl₃): δ 2.20 (s, 6H), 3.41 (s, 2H), 4.25 (dd, 1H), 4.59 (dd, 1H), 4.70 (dd, 1H), 4.99 (m, 1H), 5.07 (dd, 1H), 6.62 (dd, 1H), 6.74 (d, 1H), 7.28 (d, 1H), 7.47 (t, 2H), 7.52 (t, 1H), 8.10 (d, 2H), MS (APCI+) m/z 413 [M+H]+, LC purity: 95%.

Example 49

(3-(3-Chloro-4-((4-methylpiperazin-1-yl)methyl)phenoxy)azetidin-1-yl)(5-(4-methoxyphenyl)-1,3,4-oxadiazol-2-yl)methanone

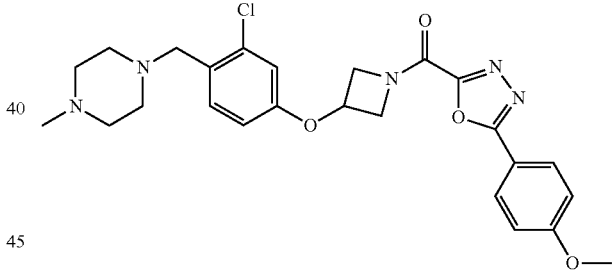

49A. 1-(4-(Azetidin-3-yloxy)-2-chlorobenzyl)-4-methylpiperazine

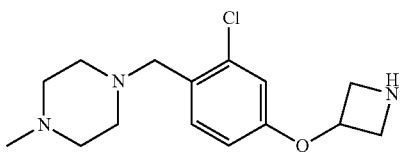 [SMILES: CN1CCN(Cc2ccc(OC3CNC3)cc2Cl)CC1]

Using similar protocols as described in Examples 20A, 20B and 20C employing 1-methylpiperazine and 2-chloro-4-hydroxybenzaldehyde as starting material afforded 0.32 g (32%) of 49A as an oil. ¹H NMR (500 MHz, CDCl₃): δ 2.29 (s, 3H), 2.3-2.7 (m, 8H), 3.55 (s, 2H), 3.78 (m, 2H), 3.92 (m, 2H), 4.96 (m, 1H), 6.64 (d, 1H), 6.74 (d, 1H), 7.31 (m, 1H), MS (APCI+) m/z 296 [M+H]+.

49. (3-(3-chloro-4-((4-methylpiperazin-1-yl)methyl) phenoxy)azetidin-1-yl)(5-(4-methoxyphenyl)-1,3,4-oxadiazol-2-yl)methanone Using a similar protocol as described in Example 16 employing 49A (2.7 g, 9.1 mmol) and ethyl 5-(4-methoxyphenyl)-1,3,4-oxadiazole-2-carboxylate (2.5 g, 10.0 mmol) as starting materials afforded 2.9 g (64%) of 49 as a solid. $^1$H NMR (500 MHz, CDCl$_3$): δ 2.28 (s, 3H), 2.3-2.7 (m, 8H), 3.56 (s, 2H), 3.88 (s, 3H), 4.32 (dd, 1H), 4.63 (dd, 1H), 4.74 (dd, 1H), 5.05 (m, 1H), 5.11 (m, 1H), 6.67 (dd, 1H), 6.78 (d, 1H), 7.02 (d, 2H), 7.39 (d, 1H), 8.09 (d, 2H), MS (APCI+) m/z 498 [M+H]$^+$, LC purity: 95%.

Example 50

(3-(3-Chloro-4-((4-methylpiperazin-1-yl)methyl) phenoxy)azetidin-1-yl)(5-phenyl-1,3,4-oxadiazol-2-yl)methanone

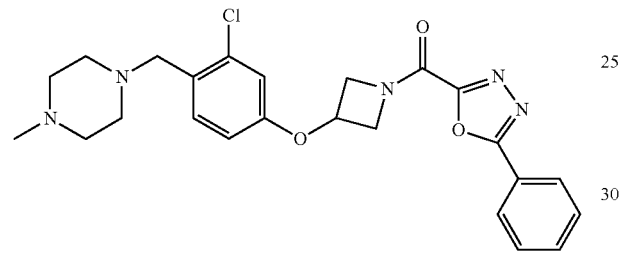

Using a similar protocol as described in Example 16 employing 49A (0.14 g, 0.47 mmol) and ethyl 5-phenyl-1,3,4-oxadiazole-2-carboxylate (0.15 g, 0.69 mmol) as starting materials afforded 70 mg (31%) of 50 as a solid. $^1$H NMR (500 MHz, DMSO-d$_6$): δ 2.13 (s, 3H), 2.3-2.5 (m, 8H), 3.45 (s, 2H), 4.09 (dd, 1H), 4.53 (dd, 1H), 4.62 (dd, 1H), 5.09 (m, 1H), 5.17 (m, 1H), 6.88 (dd, 1H), 6.97 (d, 1H), 7.37 (d, 1H), 7.62 (t, 2H), 7.68 (t, 1H), 8.05 (d, 2H), MS (APCI+) m/z 468 [M+H]$^+$, LC purity: 98%.

Example 51

(5-(4-(Difluoromethoxy)phenyl)-1,3,4-oxadiazol-2-yl)(3-(4-((dimethylamino)methyl)-3-fluorophenoxy) azetidin-1-yl)methanone

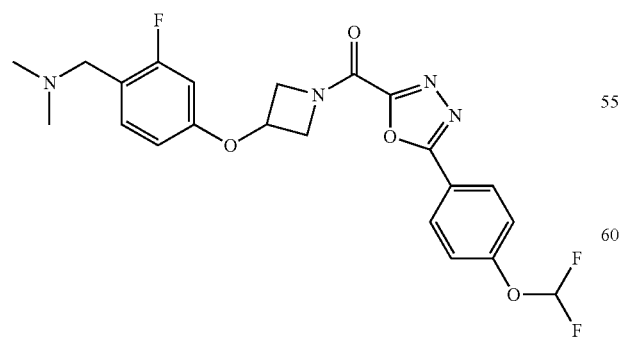

Using a similar protocol as described in Example 16 employing 26C (0.15 g, 0.65 mmol) and 37A (0.20 g, 0.71 mmol) as starting materials afforded 35 mg (12%) of 51 as a solid. $^1$H NMR (500 MHz, CDCl$_3$): δ 2.25 (s, 6H), 3.43 (s, 2H), 4.33 (dd, 1H), 4.65 (dd, 1H), 4.74 (dd, 1H), 5.06 (m, 1H), 5.13 (m, 1H), 6.51 (m, 2H), 7.27 (m, 3H), 8.17 (d, 2H), MS (APCI+) m/z 463 [M+H]$^+$, LC purity: 95%.

Example 52

(3-(3-Methoxy-2-methyl-4-(pyrrolidin-1-ylmethyl) phenoxy)azetidin-1-yl)(5-(4-methoxyphenyl)-1,3,4-oxadiazol-2-yl)methanone

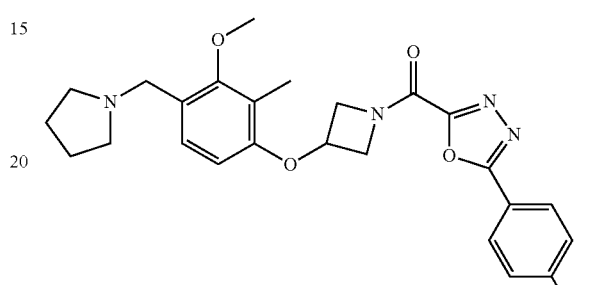

52A. 4-Hydroxy-2-methoxy-3-methylbenzaldehyde

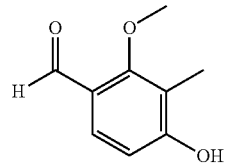

2-Methoxy-3-methyl-4-(tetrahydro-2H-pyran-2-yloxy) benzaldehyde—for preparation see e.g. *Journal of Medicinal Chemistry*, 41, 4819-4832 (1998)—(2.10 g, 8.4 mmol) was dissolved in ethanol (40 mL) and then HCl (2M, 40 mL) was added. After 20 minutes the solution was concentrated under reduced pressure. The aqueous residue was extracted twice with EtOAc and the combined organic solutions were washed with brine. The solution was dried over Na$_2$SO$_4$ and the solvent was removed by evaporation. The product was washed with petroleum-ether. There was obtained 1.0 g (72%) of 52A as a solid. $^1$H NMR (500 MHz, CDCl$_3$): δ 2.05 (s, 3H), 3.78 (s, 3H), 6.74 (d, 1H), 7.49 (d, 1H), 10.05 (s, 1H).

52B. 1-(4-(Azetidin-3-yloxy)-2-methoxy-3-methylbenzyl)pyrrolidine

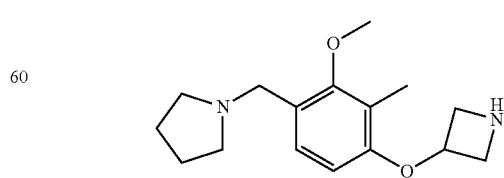

Using similar protocols as described in Examples 31A, 31B and 31C employing pyrrolidine and 52A as starting materials afforded 0.25 g (30%) of 52B as an oil. $^1$H NMR (500 MHz, CDCl$_3$): δ 1.75 (s, 4H), 2.16 (s, 3H), 2.51 (s, 4H), 3.70 (s, 2H), 3.74 (s, 3H), 3.79 (m, 2H), 3.91 (m, 2H), 4.97 (m, 1H), 6.29 (d, 1H), 7.11 (d, 1H), MS (APCI+) m/z 277 [M+H]$^+$.

52. (3-(3-M ethoxy-2-methyl-4-(pyrrolidin-1-ylmethyl)phenoxy)azetidin-1-yl)(5-(4-methoxyphenyl)-1,3,4-oxadiazol-2-yl)methanone Using a similar protocol as described in Example 16 employing 52B (0.25 g, 0.90 mmol) and ethyl 5-(4-methoxyphenyl)-1,3,4-oxadiazole-2-carboxylate (0.34 g, 1.36 mmol) as starting materials afforded 160 mg (37%) of 52 as a solid. $^1$H NMR (500 MHz, CDCl$_3$): δ 1.77 (s, 4H), 2.19 (s, 3H), 2.52 (s, 4H), 3.60 (s, 2H), 3.76 (s, 3H), 3.89 (s, 3H), 4.35 (dd, 1H), 4.66 (dd, 1H), 4.75 (dd, 1H), 5.07 (m, 1H), 5.13 (dd, 1H), 6.29 (d, 1H), 7.02 (d, 2H), 7.17 (d, 1H), 8.10 (d, 2H), MS (APCI+) m/z 479 [M+H]$^+$, LC purity: 95%.

Example 53

(3-(3-Methyl-4-((methylamino)methyl)phenoxy)azetidin-1-yl)(5-phenyl-1,3,4-oxadiazol-2-yl)methanone

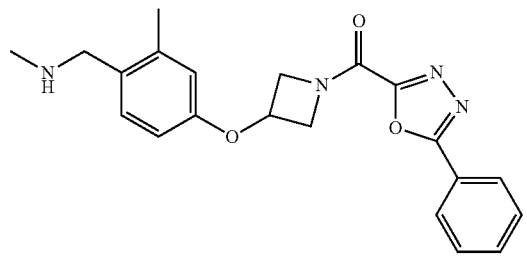 [SMILES: CNCc1ccc(OC2CN(C(=O)c3nnc(-c4ccccc4)o3)C2)cc1C]

53A. (3-Hydroxyazetidin-1-yl)(5-phenyl-1,3,4-oxadiazol-2-yl)methanone

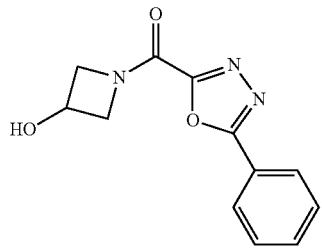 [SMILES: O=C(c1nnc(-c2ccccc2)o1)N1CC(O)C1]

To a clear solution of ethyl 5-phenyl-1,3,4-oxadiazole-2-carboxylate (0.40 g, 1.83 mmol) in dry methanol (5 mL) was added sodium cyanide (18 mg, 0.37 mmol). A solution of 3-hydroxyazetidine hydrochloride (0.45 g, 2.84 mmol) and triethylamine (0.40 mL, 2.84 mmol) in methanol (5 mL) was added at ambient temperature. After stirring for 20 min water (20 mL) and dichloromethane (30 mL) were added. The layers were separated and the aqueous phase was extracted twice with dichloromethane (30 mL). The combined organic layers were evaporated. The crude product was then treated with toluene (5 mL), filtered, washed with toluene (5 mL) and dried in vacuo. There was obtained 0.40 g (90%) of 53A as a solid. $^1$H NMR (400 MHz, DMSO-d$_6$): δ 3.84 (dd, 1H), 4.31 (m, 2H), 4.56 (m, 1H), 4.79 (dd, 1H), 5.87 (d, 1H), 7.64 (m, 3H), 8.05 (d, 2H), MS (APCI+) m/z 246 [M+H]$^+$.

53B. 1-(5-Phenyl-1,3,4-oxadiazole-2-carbonyl)azetidin-3-yl methanesulfonate

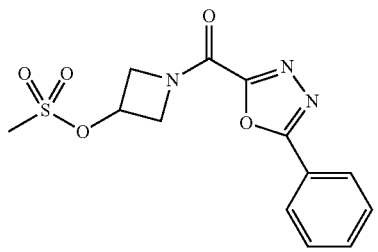 [SMILES: CS(=O)(=O)OC1CN(C(=O)c2nnc(-c3ccccc3)o2)C1]

A suspension of 53A (2.00 g, 8.16 mmol) in dichloromethane (200 mL) was cooled in an ice-bath. Triethylamine (1.58 mL, 11.42 mmol) was added followed by methanesulfonyl chloride (0.85 mL, 11.01 mmol). After the addition, the cooling bath was removed. The mixture was stirred overnight and then transferred to a separatory funnel. The mixture was washed with water and then with aqueous NaHCO$_3$. The organic solution was dried (phase separator) and evaporated. There was obtained 2.58 g (98%) of 53B as a solid. $^1$H NMR (500 MHz, CDCl$_3$): δ 3.13 (s, 3H), 4.43 (dd, 1H), 4.64 (dd, 1H), 4.87 (dd, 1H), 5.12 (dd, 1H), 5.40 (m, 1H), 7.54 (t, 2H), 7.59 (t, 1H), 8.15 (d, 2H), MS (APCI+) m/z 324 [M+H]$^+$.

53C. 2-Methyl-4-(1-(5-phenyl-1,3,4-oxadiazole-2-carbonyl)azetidin-3-yloxy)benzaldehyde

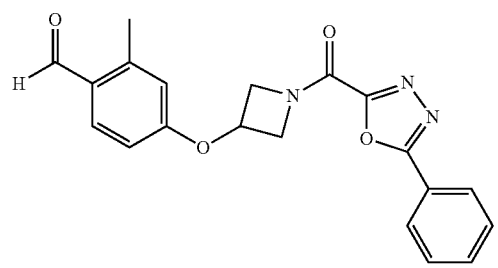 [SMILES: Cc1cc(OC2CN(C(=O)c3nnc(-c4ccccc4)o3)C2)ccc1C=O]

To a solution of 4-hydroxy-2-methylbenzaldehyde (0.11 g, 0.79 mmol) and 53B (0.20 g, 0.62 mmol) in DMF (10 mL) under nitrogen was added Cs$_2$CO$_3$ (0.24 g, 0.74 mmol). The mixture was stirred at 90° C. for 20 h, cooled to RT and then diluted with DCM. The solids were filtered off and the filtrate was evaporated. The product was purified on two occasions by preparative HPLC (Kromasil, C8) eluting with a gradient of acetonitrile and a mixture of acetic acid and water (0.2%). The pure fractions were iii combined and concentrated. The aqueous residues were extracted with DCM and the organic solutions were evaporated. There was obtained 162 mg (72%) of 53C as a solid. $^1$H NMR (500 MHz, CDCl$_3$): δ 2.66 (s, 3H), 4.34 (d, 1H), 4.69 (dd, 1H), 4.76 (d, 1H), 5.17 (m, 2H), 6.64 (d, 1H), 6.72 (dd, 1H), 7.53 (t, 2H), 7.59 (t, 1H), 7.78 (d, 1H), 8.15 (d, 1H), 10.14 (s, 1H), MS (APCI+) m/z 364 [M+H]$^+$.

53. (3-(3-Methyl-4-((methylamino)methyl)phenoxy) azetidin-1-yl)(5-phenyl-1,3,4-oxadiazol-2-yl)methanone Titanium(IV) isopropoxide (0.20 mL, 0.68 mmol) was added to a methanol solution of methylamine (0.75 mL 2M, 1.50 mmol). The resulting solution was added to 53C (162 mg, 0.45 mmol) and then methanol (1 mL) was added. After 60 min, DCM (5 mL) was added and the solution was stirred for 2 h. Sodium borohydride (21 mg, 0.56 mmol) was added and the mixture was stirred for 60 min. Water was added and the mixture was filtered through Celite and the solid was washed extensively with DCM. The filtrate was further filtered through a phase separator and the organic solution was evaporated. The product was purified by preparative HPLC (Kromasil, C8) eluting with a gradient of acetonitrile and a mixture of acetic acid and water (0.2%). The pure fractions were combined and freeze-dried twice. There was obtained 74 mg (44%) of 53 as a solid. $^1$H NMR (500 MHz, CDCl$_3$): δ 2.27 (s, 3H), 2.3-2.6 (m, 4H), 3.62 (m, 2H), 4.24 (dd, 1H), 4.56 (dd, 1H), 4.66 (dd, 1H), 4.99 (m, 1H), 5.04 (m, 1H), 6.49 (d, 1H), 6.54 (s, 1H), 7.15 (d, 1H), 7.46 (t, 2H), 7.51 (t, 1H), 8.08 (d, 2H), MS (APCI+) m/z 379 [M+H]$^+$, LC purity: 99%.

Example 54

(5-(4-Methoxyphenyl)-1,3,4-oxadiazol-2-yl)(3-(2-methyl-4-((methylamino)methyl)phenoxy)azetidin-1-yl)methanone

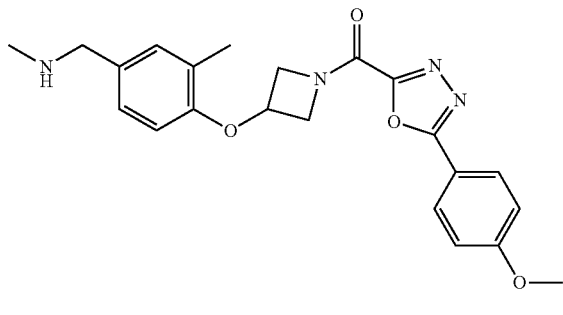

54A. 4-(1-(5-(4-Methoxyphenyl)-1,3,4-oxadiazole-2-carbonyl)azetidin-3-yloxy)-3-methylbenzaldehyde

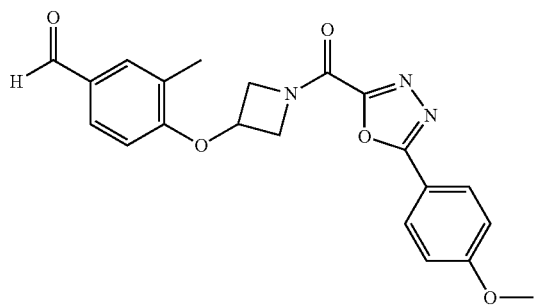 [SMILES: COc1ccc(-c2nnc(C(=O)N3CC(Oc4ccc(C=O)cc4C)C3)o2)cc1]

Using similar protocols as described in Example 53A, 53B and 53C employing ethyl 5-(4-methoxyphenyl)-1,3,4-oxadiazole-2-carboxylate as starting material afforded 0.37 g (38%) of 54A as a solid. $^1$H NMR (500 MHz, CDCl$_3$): δ 2.32 (s, 3H), 3.89 (s, 3H), 4.36 (d, 1H), 4.72 (dd, 1H), 4.80 (d, 1H), 5.17 (m, 2H), 6.62 (d, 1H), 7.02 (d, 2H), 7.71 (d, 1H), 7.74 (s, 1H), 8.10 (d, 2H), 9.89 (s, 1H), MS (APCI+) m/z 394 [M+H]$^+$.

54. (5-(4-Methoxyphenyl)-1,3,4-oxadiazol-2-yl)(3-(2-methyl-4-((methylamino)methyl)phenoxy)azetidin-1-yl)methanone Using a similar protocol as described in Example 53 employing 54A (0.33 g, 0.84 mmol) as starting material afforded 130 mg (38%) of 54 as a solid. $^1$H NMR (500 MHz, CDCl$_3$): δ 2.25 (s, 3H), 2.46 (s, 3H), 3.67 (s, 2H), 3.89 (s, 3H), 4.33 (m, 1H), 4.65 (m, 1H), 4.75 (m, 1H), 5.06 (m, 1H), 5.13 (m, 1H), 6.45 (d, 1H), 7.03 (d, 2H), 7.08 (d, 1H), 7.16 (s, 1H), 8.10 (d, 2H), MS (APCI+) m/z 409 [M+H]$^+$, LC purity: 98%.

Example 55

(3-(4-((3-Methoxyazetidin-1-yl)methyl)phenoxy) azetidin-1-yl)(5-(4-methoxyphenyl)-1,3,4-oxadiazol-2-yl)methanone

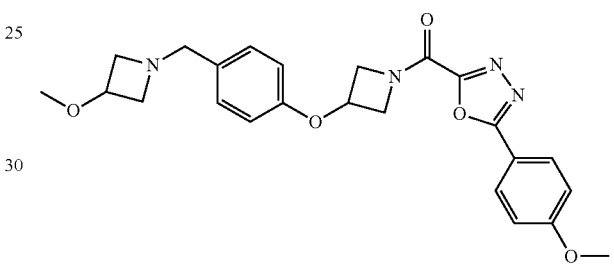

55A. 4-(1-(5-(4-Methoxyphenyl)-1,3,4-oxadiazole-2-carbonyl)azetidin-3-yloxy)benzaldehyde

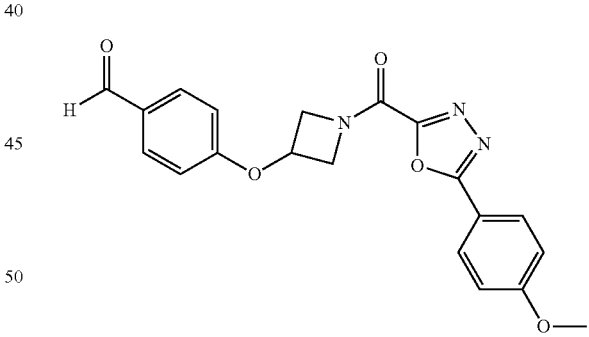

Using similar protocols as described in Example 53A, 53B and 53C employing ethyl 5-(4-methoxyphenyl)-1,3,4-oxadiazole-2-carboxylate as starting material afforded 0.47 g (32%) of 55A as a solid. $^1$H NMR (500 MHz, CDCl$_3$): δ 3.89 (s, 3H), 4.36 (d, 1H), 4.70 (dd, 1H), 4.79 (m, 1H), 5.18 (m, 2H), 6.91 (d, 2H), 7.03 (d, 2H), 7.88 (d, 2H), 8.10 (d, 2H), 9.93 (s, 1H), MS (APCI+) m/z 380 [M+H]$^+$.

55. (3-(4-(3-Methoxyazetidin-1-yl)methyl)phenoxy) azetidin-1-yl)(5-(4-methoxyphenyl)-1,3,4-oxadiazol-2-yl)methanone Intermediate 55A (0.15 g, 0.40 mmol) was dissolved in dry DCM (6 mL) and 3-methoxyazetidine hydrochloride (64 mg, 0.51 mmol) was added followed by triethylamine (0.071 mL, 0.51 mmol). The reaction mixture was stirred at RT for 30 min and then sodium triacetoxyborohydride (126 mg, 0.59 mmol) was added. The mixture was stirred for 2 h and then diluted with DCM and transferred to a separatory funnel. The organic layer was washed with an aqueous solution of Na$_2$CO$_3$, dried (phase separator) and evaporated. The crude product was purified by flash column chromatography eluting with a mixture of DCM and MeOH, which contained 2M NH$_3$ (30:1). There was obtained 135 mg (76%) of 55 as a solid. $^1$H NMR (500 MHz, CDCl$_3$): δ 2.93 (m, 2H), 3.25 (s, 3H), 3.58 (m, 4H), 3.89 (s, 3H), 4.05 (m, 1H), 4.32 (m, 1H), 4.63 (m, 1H), 4.75 (m, 1H), 5.06 (m, 1H), 5.11 (m, 1H), 6.73 (d, 1H), 7.02 (d, 2H), 7.22 (d, 2H), 8.10 (d, 2H), MS (APCI+) m/z 451 [M+H]$^+$, LC purity: 97%.

Example 56

(3-(4-((3-Cyclopropyl-3-hydroxyazetidin-1-yl)methyl)phenoxy)azetidin-1-yl)(5-(4-methoxyphenyl)-1,3,4-oxadiazol-2-yl)methanone

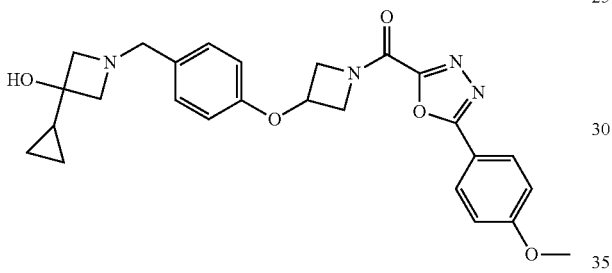

Using a similar protocol as described in Example 55 employing 55A (0.15 g, 0.40 mmol) and 3-cyclopropylazetidin-3-ol (77 mg, 0.51 mmol)—for preparation see e.g. WO2009018415—as starting materials afforded 166 mg (88%) of 56 as a solid. $^1$H NMR (500 MHz, CDCl$_3$): δ 0.44 (m, 2H), 0.55 (m, 2H), 1.20 (m, 1H), 3.03 (d, 2H), 3.22 (d, 3H), 3.60 (s, 2H), 3.89 (s, 3H), 4.32 (m, 1H), 4.64 (m, 1H), 4.75 (m, 1H), 5.06 (m, 1H), 5.11 (m, 1H), 6.73 (d, 2H), 7.02 (d, 2H), 7.23 (d, 2H), 8.10 (d, 2H), MS (APCI+) m/z 477 [M+H]$^+$, LC purity: 92%.

Example 57

(3-(2-Chloro-4-((3-methoxyazetidin-1-yl)methyl)phenoxy)azetidin-1-yl)(5-phenyl-1,3,4-oxadiazol-2-yl)methanone

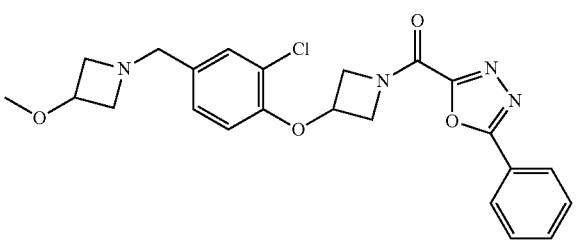 [SMILES: COC1CN(Cc2ccc(OC3CN(C(=O)c4nnc(-c5ccccc5)o4)C3)c(Cl)c2)C1]

57A. 3-Chloro-4-(1-(5-phenyl-1,3,4-oxadiazole-2-carbonyl)azetidin-3-yloxy)benzaldehyde

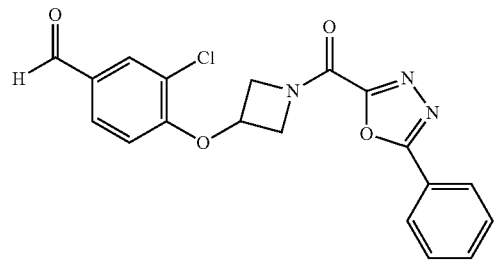

Using a similar protocol as described in Example 53C employing 53B (1.0 g, 3.10 mmol) and 3-chloro-4-hydroxybenzaldehyde (0.50 g, 3.19 mmol) as starting materials afforded 0.54 g (45%) of 57A as a solid. $^1$H NMR (500 MHz, CD$_3$OD): δ 4.34 (m, 1H), 4.77 (m, 2H), 5.25 (m, 1H), 5.36 (m, 1H), 7.05 (d, 1H), 7.62 (m, 3H), 7.7-8.1 (m, 2H), 8.14 (d, 2H), 9.87 (s, 1H), MS (APCI+) m/z 384 [M+H]$^+$.

57. (3-(2-Chloro-4-((3-methoxyazetidin-1-yl)methyl)phenoxy)azetidin-1-yl)(5-phenyl-1,3,4-oxadiazol-2-yl)methanone Using a similar protocol as described in Example 55 employing 57A (0.12 g, 0.31 mmol) and 3-methoxyazetidine hydrochloride (50 mg, 0.40 mmol) as starting materials afforded 60 mg (43%) of 57 as a solid. $^1$H NMR (500 MHz, CD$_3$OD): δ 3.02 (m, 2H), 3.25 (s, 3H), 3.55 (m, 2H), 3.59 (s, 2H), 4.04 (m, 1H), 4.29 (d, 1H), 4.73 (m, 2H), 5.19 (m, 2H), 6.84 (d, 1H), 7.21 (d, 1H), 7.38 (s, 1H), 7.59 (t, 2H), 7.65 (t, 1H), 8.14 (d, 2H), MS (APCI+) m/z 456 [M+H]$^+$, LC purity: 96%.

Example 58

(3-(2-Chloro-4-((3-hydroxyazetidin-1-yl)methyl)phenoxy)azetidin-1-yl)(5-phenyl-1,3,4-oxadiazol-2-yl)methanone

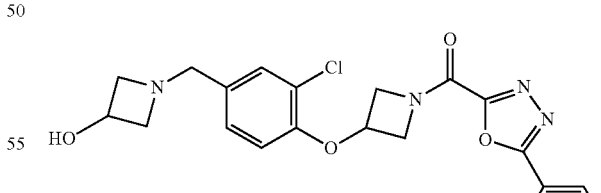

Using a similar protocol as described in Example 55 employing 57A (0.12 g, 0.31 mmol) and 3-hydroxyazetidine hydrochloride (40 mg, 0.37 mmol) as starting materials afforded 50 mg (36%) of 58 as a solid. $^1$H NMR (500 MHz, CD$_3$OD): δ 2.65 (m, 2H), 2.95 (m, 2H), 3.58 (m, 2H), 4.28 (dd, 1H), 4.35 (m, 1H), 4.73 (m, 2H), 5.19 (m, 2H), 6.83 (d, 1H), 7.20 (d, 1H), 7.37 (s, 1H), 7.59 (t, 2H), 7.64 (t, 1H), 8.14 (d, 2H), MS (APCI+) m/z 441 [M+H]+, LC purity: 97%.

Example 59

(5-(4-Methoxyphenyl)-1,3,4-oxadiazol-2-yl)(3-(4-(pyrrolidin-1-ylmethyl)phenylthio)azetidin-1-yl)methanone

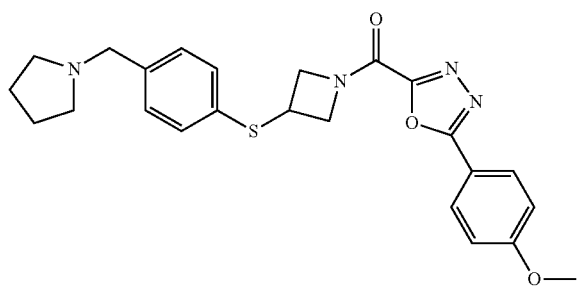

59A. tert-Butyl 3-(4-(methoxycarbonyl)phenylthio)azetidine-1-carboxylate

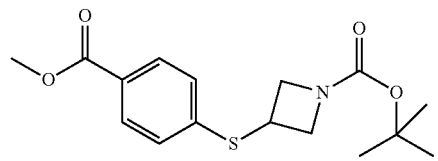 [SMILES: COC(=O)c1ccc(SC2CN(C(=O)OC(C)(C)C)C2)cc1]

Methyl 4-mercaptobenzoate (3.00 g, 17.8 mmol) and tert-butyl 3-(methylsulfonyloxy)azetidine-1-carboxylate (4.48 g, 17.8 mmol) were dissolved in DMF (30 mL). Cs$_2$CO$_3$ (6.97 g, 21.4 mmol) was added and the mixture was stirred at 90° C. for 3 hours, then cooled to room temperature. EtOAc (50 ml) was added and the solids were filtered off. The filtrate was washed with a saturated aqueous K$_2$CO$_3$ solution (20 mL), dried (MgSO$_4$) and then evaporated. The residue was purified by column chromatography eluting with heptane, EtOAc/heptane (5:95, then 10:90). There was obtained 3.10 g (53%) of 59A as a solid. $^1$H NMR (500 MHz, CDCl$_3$): δ 1.45 (s, 9H), 3.89 (m, 2H), 3.90 (s, 3H), 4.11 (m, 1H), 4.42 (t, 2H), 7.16 (d, 2H), 7.95 (d, 2H).

59B. 4-(1-(tert-Butoxycarbonyl)azetidin-3-ylthio)benzoic acid

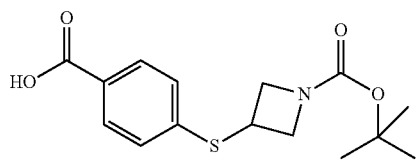 [SMILES: CC(C)(C)OC(=O)N1CC(Sc2ccc(C(=O)O)cc2)C1]

A solution of LiOH (0.33 g, 13.7 mmol) in water (30 mL) was added dropwise to a solution of 59A (2.2 g, 6.8 mmol) in THF (30 mL). The mixture was stirred at RT for 15 h and then concentrated on a rotavapor when most of the organic solvent was removed. The aqueous solution was cooled by an external ice-bath and the pH was adjusted to pH 3 by adding aqueous HCl (0.2M) dropwise in the presence of EtOAc. The aqueous layer was further extracted with EtOAc and the combined organic solutions were washed with brine. The solution was dried over Na$_2$SO$_4$ and then evaporated. There was obtained 2.0 g (95%) of 59A as a powder. $^1$H NMR (500 MHz, CDCl$_3$): δ 1.44 (s, 9H), 3.90 (m, 2H), 4.13 (m, 1H), 4.44 (t, 2H), 7.19 (d, 2H), 8.01 (d, 2H).

59C. tert-Butyl 3-(4-(pyrrolidine-1-carbonyl)phenylthio)azetidine-1-carboxylate

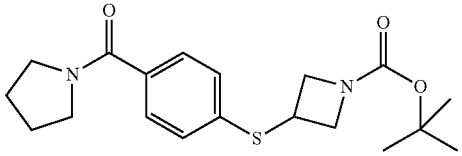 [SMILES: CC(C)(C)OC(=O)N1CC(Sc2ccc(C(=O)N3CCCC3)cc2)C1]

Pyrrolidine (0.60 g, 8.4 mmol) was added to a solution of 59B (2.0 g, 6.5 mmol) and DCM (25 mL). The mixture was cooled to 0° C. and then DIPEA and TBTU were added in the given order. The mixture was stirred at 0° C. for 20 min and then at RT for 1.5 h. The solution was washed with aqueous Na$_2$CO$_3$ (1M) and then the organic solution was evaporated. The product was purified by silica-gel chromatography using 1-5% methanol in DCM. There was obtained 2.3 g (98%) of 59C as an oil. $^1$H NMR (500 MHz, CDCl$_3$): δ 1.42 (s, 9H), 1.89 (m, 4H), 3.41 (m, 2H), 3.62 (m, 2H), 3.86 (m, 2H), 4.04 (m, 1H), 4.34 (m, 2H), 7.19 (d, 2H), 7.45 (d, 2H), MS (APCI+) m/z 363 [M+H]+.

59D. (4-(Azetidin-3-ylthio)phenyl)(pyrrolidin-1-yl)methanone

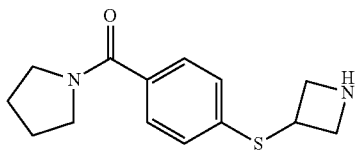 [SMILES: O=C(c1ccc(SC2CNC2)cc1)N1CCCC1]

To a solution of 59C (1.40 g, 3.89 mmol) in dioxane (20 mL) was added a solution of HCl (4M in dioxane, 20 mL). The mixture was stirred at RT over night and then the solvent was removed by evaporation. The residue was partitioned between DCM and water. The Organic solution was extracted with an aqueous solution of HCl (0.1 M). The combined aqueous solutions were pH adjusted to pH>11 by carefully adding a saturated aqueous solution of Na$_2$CO$_3$. The mixture was extracted several times with DCM. The solvent was removed by evaporation. There was obtained 0.56 g (55%) of 59D as an oil. $^1$H NMR (500 MHz, CDCl$_3$): δ 1.88 (m, 2H), 1.94 (m, 2H), 3.43 (m, 2H), 3.62 (m, 2H), 3.68 (m, 2H), 4.04 (m, 2H), 4.29 (m, 1H), 7.19 (d, 2H), 7.44 (d, 2H), MS (APCI+) m/z 263 [M+H]$^+$.

59E. 1-(4-(Azetidin-3-ylthio)benzyl)pyrrolidine

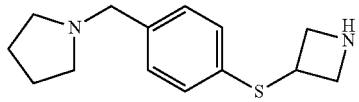 [SMILES: c1cc(SC2CNC2)ccc1CN1CCCC1]

Intermediate 59D (0.56 g, 2.1 mmol) was dissolved in dry THF (4 mL) under nitrogen. A THF solution of LiAlH$_4$ (5 mL 1M, 5 mmol) was added dropwise. The mixture was stirred at 50° C. for 5 h. Water (0.2 mL), aqueous 15% NaOH solution (0.2 mL) and then water (0.2 mL) were added carefully in the given order while cooling. The mixture was stirred for one hour and the solid was filtered off. The solvent was removed by evaporation. There was obtained 0.37 g (70%) of 59D as an oil. $^1$H NMR (500 MHz, DMSO-d$_6$): δ 1.64 (m, 4H), 2.37 (m, 4H), 2.9-4.2 (m, 6H), 7.0-7.3 (m, 4H), MS (APCI+) m/z 249 [M+H]$^+$.

59. (5-(4-Methoxyphenyl)-1,3,4-oxadiazol-2-yl)(3-(4-(pyrrolidin-1-ylmethyl)phenylthio)azetidin-1-yl)methanone Intermediate 59E (0.37 g, 1.5 mmol) and ethyl 5-(4-methoxyphenyl)-1,3,4-oxadiazole-2-carboxylate (0.48 g, 1.9 mmol) were mixed and heated to 120° C. for 2 h using an oil-bath. The product was purified by flash-chromatography using 1-5% methanol/DCM where the methanol contained ammonia (2M). The product crystallised when adding ether and the solid was dried in vacuo. There was obtained 0.16 g (24%) of 59 as a solid. $^1$H NMR (500 MHz, CDCl$_3$): δ 1.81 (m, 4H), 2.51 (m, 4H), 3.62 (m, 2H), 3.89 (s, 3H), 4.18 (m, 2H), 4.63 (m, 2H), 5.11 (m, 1H), 7.02 (d, 2H), 7.27 (m, 4H), 8.09 (d, 2H), MS (APCI+) m/z 451 [M+H]$^+$, LC purity: 97%.

Example 60

(3-(4-((Dimethylamino)methyl)phenylthio)azetidin-1-yl)(5-phenyl-1,3,4-oxadiazol-2-yl)methanone

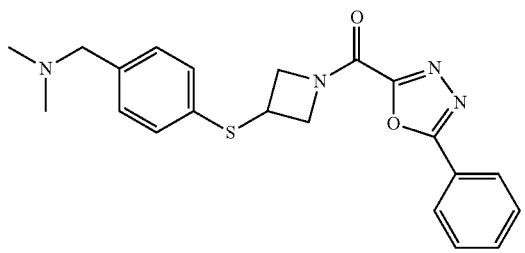 [SMILES: CN(C)Cc1ccc(SC2CN(C(=O)c3nnc(-c4ccccc4)o3)C2)cc1]

60A. (3-(4-(Hydroxymethyl)phenylthio)azetidin-1-yl)(5-phenyl-1,3,4-oxadiazol-2-yl)methanone

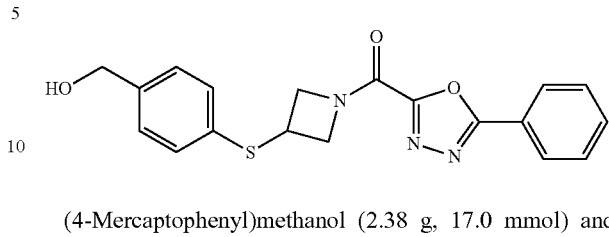

(4-Mercaptophenyl)methanol (2.38 g, 17.0 mmol) and 53B (5.00 g, 15.5 mmol) were mixed in DMF (80 mL). Cs$_2$CO$_3$ (6.05 g, 18.56 mmol) was added. The mixture was stirred at 90° C. overnight and then cooled room temperature. Ethyl acetate (150 mL) was added and the mixture was washed with water (50 mL). The aqueous layer was extracted with ethyl acetate (100 mL). The organic phases were combined, dried (MgSO$_4$) and evaporated to dryness. The residue was purified by column chromatography eluting with ethyl acetate/heptane (20:80, 40:60 and then 60:40). There was obtained 3.5 g (61%) of 60A as a solid. $^1$H NMR (500 MHz, CDCl$_3$): δ 4.19 (m, 2H), 4.64 (m, 2H), 4.69 (s, 2H), 5.10 (m, 1H), 7.34 (m, 4H), 7.53 (t, 2H), 7.59 (t, 1H), 8.15 (d, 2H), MS (APCI+) m/z 368 [M−H]$^+$.

60B. (3-(4-(Chloromethyl)phenylthio)azetidin-1-yl)(5-phenyl-1,3,4-oxadiazol-2-yl)methanone

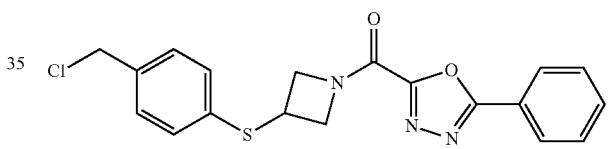

Intermediate 60A (3.48 g, 9.47 mmol) was dissolved in dichloromethane (150 mL) and the mixture was cooled in an ice bath. While stirring, thionyl chloride (0.76 mL, 10.4 mmol) was added dropwise. The cooling bath was removed after 30 min. The mixture was stirred for 2.5 h and then evaporated to dryness. The residue was purified by column chromatography eluting with dichloromethane. There was obtained 2.93 g (80%) of 60B as a solid. $^1$H NMR (500 MHz, CDCl$_3$): δ 4.22 (m, 2H), 4.57 (s, 2H), 4.65 (m, 2H), 5.14 (m, 1H), 7.29 (d, 2H), 7.36 (d, 2H), 7.53 (t, 2H), 7.59 (t, 1H), 8.16 (d, 2H), MS (APCI+) m/z 386 [M+H]$^+$.

60. (3-(4-((Dimethylamino)methyl)phenylthio)azetidin-1-yl)(5-phenyl-1,3,4-oxadiazol-2-yl)methanone Dimethylamine hydrochloride (0.10 g, 1.24 mmol) and 60B (0.16 g, 0.41 mmol) were mixed in DCM (5 ml). Triethylamine (0.290 ml, 2.07 mmol) was added and the mixture was stirred at RT for 2.5 h. More of triethylamine (0.290 ml, 2.07 mmol) and dimethylamine hydrochloride (0.10 g, 1.24 mmol) were added. The mixture was stirred overnight at RT and then diluted with DCM (10 ml). The mixture was washed with water, filtered through a phase separator and then evaporated. The residue was purified by column chromatography eluting with NH$_3$ in MeOH (2M)/DCM (1:99, 2:98). There was obtained 0.14 g (84%) of 60 as a solid. $^1$H NMR (500 MHz, CDCl$_3$): δ 2.20 (s, 6H), 3.38 (s, 2H), 4.16 (m, 2H), 4.61

(m, 2H), 5.07 (m, 1H), 7.50 (t, 2H), 7.56 (t, 1H), 8.12 (d, 2H), MS (APCI+) m/z 395 [M+H]+, LC purity: 97%.

Example 61

(3-(4-(((2-Methoxyethyl)(methyl)amino)methyl)phenylthio)azetidin-1-yl)(5-phenyl-1,3,4-oxadiazol-2-yl)methanone hydrochloride

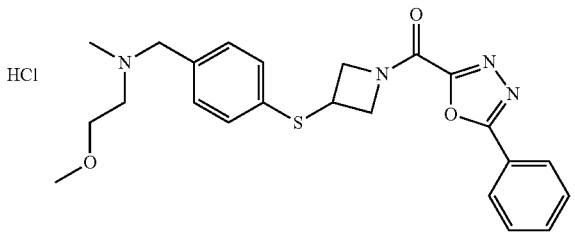 [SMILES: Cl ; COCCN(C)Cc1ccc(SC2CN(C(=O)c3nnc(-c4ccccc4)o3)C2)cc1]

Using a similar protocol as described in Example 60 employing 60B (0.16 g, 0.41 mmol) and 2-methoxy-N-methylethanamine (0.037 g, 0.41 mmol) as starting materials afforded the desired compound in neutral form as a gum. The residue was then dissolved in MeOH (2 ml) whereupon HCl in MeOH (1.25 M, 2 ml) was added. After a little while, it was evaporated to dryness. The residue was triturated with MeOH/diethyl ether. There was obtained 0.16 g (80%) of 61 as a solid. $^1$H NMR (500 MHz, DMSO-$d_6$): δ 2.64 (s, 3H), 3.15 (m, 1H), 3.23 (m, 1H), 3.27 (s, 3H), 3.73 (m, 2H), 3.98 (m, 1H), 4.25 (dd, 1H), 4.34 (dd, 1H), 4.47 (m, 2H), 4.68 (m, 1H), 5.15 (m, 1H), 7.35 (d, 2H), 7.5-7.7 (m, 5H), 8.04 (d, 2H), 11.0 (m, 1H), MS (APCI+) m/z 439 [M+H]+, LC purity: 88%.

Example 62

(3-(4-((3-Methoxyazetidin-1-yl)methyl)phenylthio)azetidin-1-yl)(5-phenyl-1,3,4-oxadiazol-2-yl)methanone

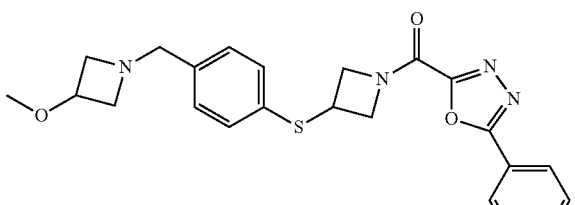

Using a similar protocol as described in Example 60 employing 60B (0.16 g, 0.41 mmol) and 3-methoxyazetidine (0.070 g, 0.83 mmol) as starting materials afforded 0.15 g (82%) of 62 as a gum. $^1$H NMR (500 MHz, CDCl$_3$): δ 2.90 (t, 2H), 3.21 (s, 3H), 3.55 (m, 4H), 4.01 (m, 1H), 4.14 (m, 2H), 4.59 (m, 2H), 5.07 (m, 1H), 7.23 (m, 4H), 7.49 (t, 2H), 7.54 (t, 1H), 8.10 (d, 2H), MS (APCI+) m/z 437 [M+H]+, LC purity: 94%.

Example 63

(3-(4-((Methylamino)methyl)phenylthio)azetidin-1-yl)(5-phenyl-1,3,4-oxadiazol-2-yl)methanone hydrochloride

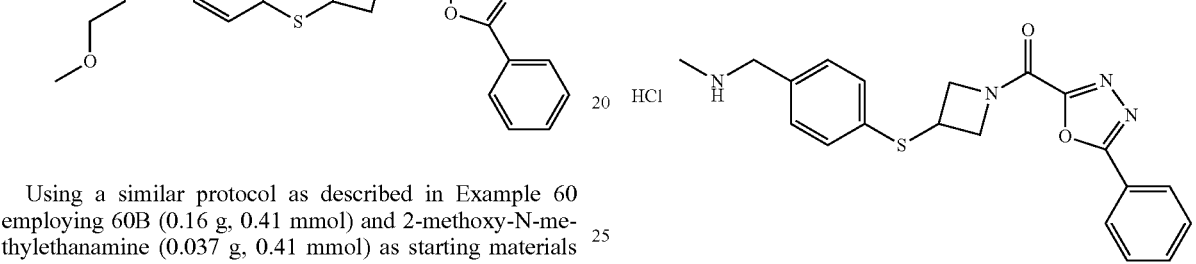

Using a similar protocol as described in Example 60 (salt formation see Example 61) employing 60B (0.16 g, 0.41 mmol) and methylamine (1.7 mL 2M in THF, 3.3 mmol) as starting materials afforded 0.12 g (68%) of 63 as a solid. $^1$H NMR (500 MHz, DMSO-$d_6$): δ 2.51 (s, 3H), 3.98 (m, 1H), 4.07 (m, 2H), 4.44 (m, 2H), 4.68 (m, 1H), 5.13 (m, 1H), 7.36 (d, 2H), 7.52 (d, 2H), 7.63 (t, 2H), 7.68 (t, 1H), 8.04 (d, 2H), 9.27 (m, 1H), MS (APCI+) m/z 381 [M+H]+, LC purity: 97%.

Example 64

(3-(4-((Methyl)tetrahydro-2H-pyran-4-yl)amino)methyl)phenylthio)azetidin-1-yl)(5-phenyl-1,3,4-oxadiazol-2-yl)methanone

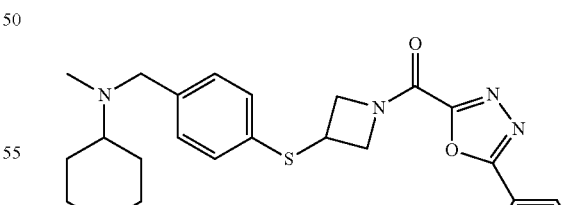

Using similar protocol as described in Example 60 employing 60B (0.18 g, 0.47 mmol) and N-methyltetrahydro-2H-pyran-4-amine (0.064 g, 0.56 mmol) as starting materials afforded 0.14 g (65%) of 64 as a solid. $^1$H NMR (500 MHz, CDCl$_3$): δ 1.61 (m, 2H), 1.71 (m, 2H), 2.13 (s, 3H), 2.57 (m, 1H), 3.32 (t, 2H), 3.52 (s, 2H), 3.98 (m, 2H), 4.14 (m, 2H), 4.58 (m, 2H), 5.05 (m, 1H), 7.25 (s, 4H), 7.47 (t, 2H), 7.53 (t, 1H), 8.09 (d, 2H), MS (APCI+) m/z 465 [M+H]+, LC purity: 98%.

Example 65

(3-(4-((Methyl((tetrahydrofuran-3-yl)methyl)amino)methyl)phenylthio)azetidin-1-yl)(5-phenyl-1,3,4-oxadiazol-2-yl)methanone

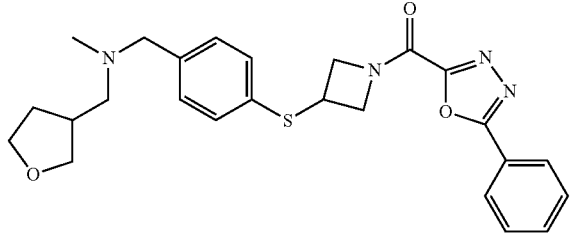 [SMILES: CN(Cc1ccc(SC2CN(C(=O)c3nnc(-c4ccccc4)o3)C2)cc1)CC1CCOC1]

Using similar protocol as described in Example 60 employing 60B (0.17 g, 0.44 mmol) and N-methyl-1-(tetrahydrofuran-3-yl)methanamine (0.066 g, 0.57 mmol) as starting materials afforded 0.092 g (45%) of 65 as a solid. ¹H NMR (500 MHz, CDCl₃): δ 1.56 (m, 1H), 1.97 (m, 1H), 2.16 (s, 3H), 2.32 (m, 2H), 2.46 (m, 1H), 3.44 (m, 3H), 3.69 (m, 1H), 3.77 (m, 1H), 3.83 (m, 1H), 4.17 (m, 2H), 4.60 (m, 2H), 5.06 (m, 1H), 7.25 (s, 4H), 7.49 (t, 2H), 7.55 (t, 1H), 8.10 (d, 2H), MS (APCI+) m/z 465 [M+H]+, LC purity: 97%.

Example 66

(3-(4-((Cyclopropylamino)methyl)phenylthio)azetidin-1-yl)(5-phenyl-1,3,4-oxadiazol-2-yl)methanone

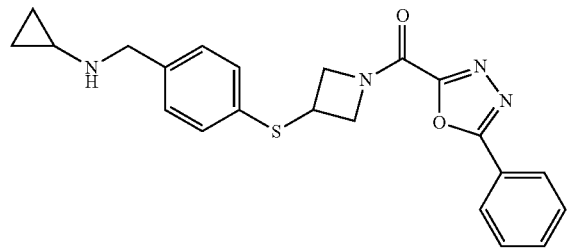 [SMILES: O=C(c1nnc(-c2ccccc2)o1)N1CC(Sc2ccc(CNC3CC3)cc2)C1]

Using similar protocol as described in Example 60 employing 60B (0.18 g, 0.47 mmol) and cyclopropylamine (0.080 g, 1.40 mmol) as starting materials afforded 0.090 g (48%) of 66 as a solid. ¹H NMR (500 MHz, CDCl₃): δ 0.36 (m, 4H), 2.00 (m, 1H), 3.78 (s, (s, 2H), 4.14 (m, 2H), 4.58 (m, 2H), 5.04 (m, 1H), 7.25 (s, 4H), 7.47 (t, 2H), 7.55 (t, 1H), 8.10 (d, 2H), MS (APCI+) m/z 407 [M+H]+, LC purity: 97%.

Example 67

(3-(4-((3-(Hydroxymethyl)azetidin-1-yl)methyl)phenylthio)azetidin-1-yl)(5-phenyl-1,3,4-oxadiazol-2-yl)methanone

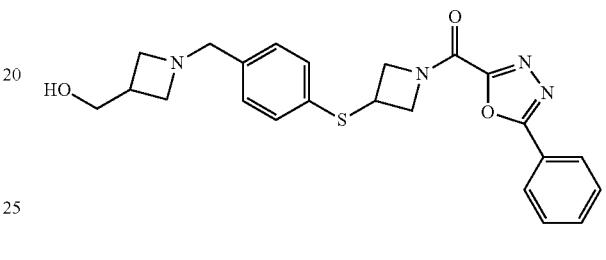

Azetidin-3-ylmethanol hydrochloride (55 mg, 0.44 mmol) and 60B (156 mg, 0.40 mmol) were mixed in acetonitrile (10 ml). To the suspension was added potassium carbonate (0.13 g, 0.93 mmol). The mixture was heated to 80° C. (oil bath) for 3 hours. The mixture was cooled to room temperature. Acetonitrile (10 ml) was added and the mixture was filtered. The filtrate was evaporated to dryness. The residue was purified by preparative HPLC using a gradient of 20-85% acetonitrile in water/acetonitrile/ammonia 95/5/0.2 buffer over 25 minutes with a flow rate of 19 mL/min. There was obtained 99 mg (56%) of 67 as a solid. ¹H NMR (500 MHz, CDCl₃): δ 2.61 (m, 1H), 3.0-3.5 (m, 5H), 3.54 (m, 2H), 3.71 (m, 2H), 4.13 (m, 2H), 4.59 (m, 2H), 5.06 (m, 1H), 7.23 (m, 4H), 7.47 (t, 2H), 7.55 (t, 1H), 8.10 (d, 2H), MS (APCI+) m/z 437 [M+H]+, LC purity: 97%.

Example 68

(3-(4-((3-(Difluoromethyl)azetidin-1-yl)methyl)phenoxy)azetidin-1-yl)(5-phenyl-1,3,4-oxadiazol-2-yl)methanone

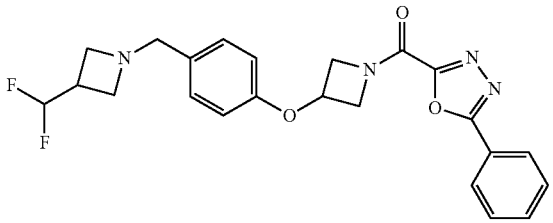 [SMILES: O=C(c1nnc(-c2ccccc2)o1)N1CC(Oc2ccc(CN3CC(C(F)F)C3)cc2)C1]

68A. 4-(1-(5-Phenyl-1,3,4-oxadiazole-2-carbonyl)azetidin-3-yloxy)benzaldehyde

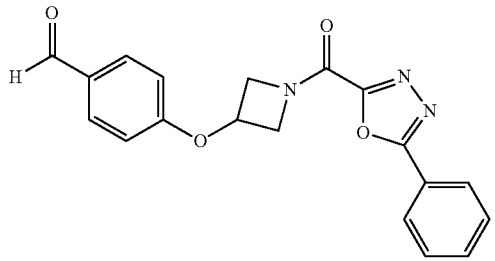 [SMILES: O=Cc1ccc(OC2CN(C(=O)c3nnc(-c4ccccc4)o3)C2)cc1]

4-Hydroxybenzaldehyde (1.10 g, 9.17 mmol), cesium carbonate (3.49 g, 10.70 mmol) and 53B (2.70 g, 7.64 mmol) were mixed with DMF (80 mL). The mixture was stirred at 110° C. for 18 h and then cooled to RT. The solids were filtered off and the filtrate was evaporated. The residue was treated with methanol and the formed solid was collected by filtration. Drying under vacuum afforded 1.8 g (62%) of 68A as a beige solid. $^1$H NMR (500 MHz, DMSO-$d_6$): δ 3.85 (s, 3H), 4.13 (dd, 1H), 4.57 (dd, 1H), 4.65 (dd, 1H), 5.12 (dd, 1H), 5.29 (m, 1H), 7.10 (d, 2H), 7.16 (d, 2H), 7.90 (d, 2H), 8.00 (d, 2H), 9.90 (s, 1H), MS (APCI+) m/z 380 [M+H]$^+$.

68B. tert-Butyl 3-(difluoromethyl)azetidine-1-carboxylate

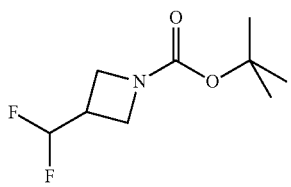

tert-Butyl 3-formylazetidine-1-carboxylate (0.93 g, 5.02 mmol) was dissolved in DCM (2 mL) under nitrogen. Deoxofluor (1.9 g, 8.60 mmol) dissolved in DCM (2 mL) was added and then, while stirring, a catalytic amount of ethanol (60 μL) was added. The mixture was stirred at RT for 24 h and then poured into a mixture of DCM (50 mL) and aqueous NaHCO$_3$ (50 mL). The two layers were stirred vigorously until no more gas was liberated. The organic solution was filtered through a phase separator and then the solvent was removed by evaporation. There was obtained 1.10 g (96%) of 68B as an oil. $^1$H NMR (500 MHz, CDCl$_3$): δ 1.44 (s, 9H), 2.93 (m, 1H), 3.88 (m, 2H), 4.00 (m, 2H), 5.94 (t, 1H).

68C. 3-(Difluoromethyl)azetidine hydrochloride

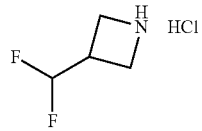

68B (1.10 g, 5.31 mmol) was dissolved in a solution of HCl in dioxane (4M, 5 mL). The mixture was stirred at RT for one day and then evaporated and co-evaporated several times together with ethanol. There was obtained 0.8 g (100%) of the HCl adduct as a yellow oil. $^1$H NMR (500 MHz, DMSO-$d_6$): δ 3.07 (m, 1H), 3.85 (m, 2H), 4.00 (m, 2H), 6.34 (t, 1H).

68. (3-(4-((3-(Difluoromethyl)azetidin-1-yl)methyl)phenoxy)azetidin-1-yl)(5-phenyl-1,3,4-oxadiazol-2-yl)methanone To a suspension of 68A (0.20 g, 0.57 mmol) in DCM (3 mL) was added 68C (0.25 g, 1.72 mmol) followed by DIPEA (0.30 mL, 1.72 mmol). Sodium triacetoxyborohydride (0.24 g, 1.15 mmol) was added. The mixture was stirred at RT for 5 h and then diluted with DCM. The solution was washed with an aqueous solution of NaHCO$_3$ and then filtered through a phase separator. The solvent was removed by evaporation. The product was purified on a silica gel column using 1-4% methanol in DCM where the methanol contained 2M ammonia. The product was triturated from ether and after drying in the hood there was obtained 47 mg (19%) of 68 as a solid. $^1$H NMR (500 MHz, CDCl$_3$): δ 2.86 (m, 1H), 3.19 (m, 2H), 3.36 (m, 2H), 3.55 (s, 2H), 4.34 (dd, 1H), 4.64 (dd, 1H), 4.78 (dd, 1H), 5.07 (m, 1H), 5.11 (m, 1H), 5.99 (t, 1H), 6.74 (d, 2H), 7.22 (d, 2H), 7.54 (t, 2H), 7.59 (t, 1H), 8.16 (d, 2H), MS (APCI+) m/z 441 [M+H]$^+$, LC purity: 90%. A sample of (3-(4-((3-(difluoromethyl)azetidin-1-yl)methyl)phenoxy)azetidin-1-yl)(5-phenyl-1,3,4-oxadiazol-2-yl)methanone was recrystallised from DCM/Et$_2$O had m. p. 147° C. (purity 99%).

Example 69

(3-(4-(4-(Hydroxymethyl)-4-methylpiperidin-1-yl)methyl)-3-methylphenoxy)azetidin-1-yl)(5-phenyl-1,3,4-oxadiazol-2-yl)methanone

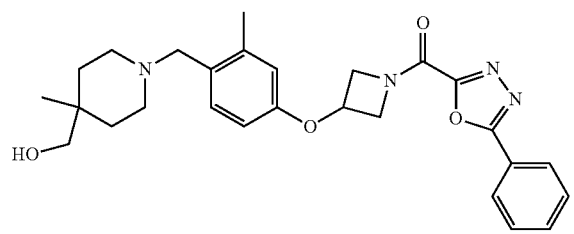 [SMILES: Cc1cc(OC2CN(C(=O)c3nnc(-c4ccccc4)o3)C2)ccc1CN1CCC(C)(CO)CC1]

69A. tert-Butyl 3-(4-formyl-3-methylphenoxy)azetidine-1-carboxylate

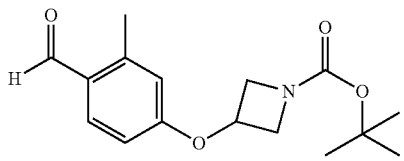 [SMILES: Cc1cc(OC2CN(C(=O)OC(C)(C)C)C2)ccc1C=O]

A slurry of sodium hydride (60%, 0.12 g, 3.10 mmol) in DMF (4 ml) was cooled by an ice-bath. Under nitrogen, 4-hydroxy-2-methylbenzaldehyde in DMF (2 ml) was added. The mixture was stirred for 30 min and then tert-butyl 3-(methylsulfonyloxy)azetidine-1-carboxylate in DMF (4 ml) was added. The mixture was heated to 100° C. using an oil bath for 3 days and then cooled to RT. Water (100 ml) was added while stirring. The mixture was extracted trice with EtOAc. The combined organic solutions were dried (MgSO₄) and then evaporated. The residue was purified by silica gel chromatography eluting with EtOAc/heptane (10:90). There was obtained 120 mg (20%) of partly purified 69A as an oil. ¹H NMR (500 MHz, CDCl₃): δ 1.46 (s, 9H), 2.64 (s, 3H), 4.01 (m, 2H), 4.33 (m, 2H), 4.94 (m, 1H), 6.60 (d, 1H), 6.66 (dd, 1H), 7.76 (d, 1H), 10.13 (s, 1H).

69B. tert-Butyl 3-(4-((4-(hydroxymethyl)-4-methylpiperidin-1-yl)methyl)-3-methylphenoxy)azetidine-1-carboxylate

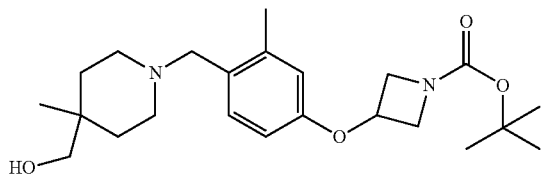 [SMILES: Cc1cc(OC2CN(C(=O)OC(C)(C)C)C2)ccc1CN1CCC(C)(CO)CC1]

To a solution of 69A (3.00 g, 10.3 mmol) in DCM (50 mL) was added (4-methylpiperidin-4-yl)methanol (2.56 g, 15.5 mmol) followed by DIPEA (3.60 mL, 20.6 mmol). The reaction mixture was stirred at RT for 20 min and then sodium triacetoxyborohydride (6.55 g, 30.9 mmol) was added. The mixture was stirred at RT overnight and then washed with a saturated aqueous solution of Na₂CO₃. The aqueous layer was extracted several times with DCM. The organic layers were filtered through a phase separator and then evaporated. There was obtained 3.1 g (74%) of the product as an oil. ¹H NMR (500 MHz, CDCl₃): δ 0.95 (s, 3H), 1.33 (m, 2H), 1.45 (s, 9H), 1.51 (m, 2H), 2.26 (m, 2H), 2.30 (s, 3H), 2.51 (m, 2H), 3.38 (s, 2H), 3.39 (s, 2H), 3.99 (m, 2H), 4.27 (m, 2H), 4.84 (m, 1H), 6.48 (dd, 1H), 6.56 (d, 1H), 7.16 (d, 1H), MS (APCI+) m/z 405 [M+H]⁺.

69C. (1-(4-(Azetidin-3-yloxy)-2-methylbenzyl)-4-methylpiperidin-4-yl)methanol

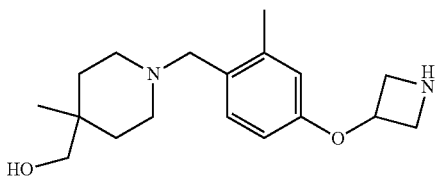 [SMILES: Cc1cc(OC2CNC2)ccc1CN1CCC(C)(CO)CC1]

To a solution of 69B (3.10 g, 7.66 mmol) in DCM (100 mL) was added TFA (30 mL) and the reaction mixture was stirred at RT for 2 h. The mixture was transferred to a reparatory funnel and water was added. The aqueous phase was carefully basified with Na₂CO₃. The organic layer was separated and the basic aqueous layer was extracted ten times with. The combined organic layers were filtered through a phase separator and the solvent was removed by evaporation. The residue was dissolved in a mixture of THF (30 mL) and an aqueous solution of NaOH (1M, 40 mL). The mixture was stirred at RT for 4 h and then the solution was concentrated using a rotavapor. The aqueous residue was extracted several times with DCM. The aqueous layer was diluted with a saturated solution of NaHCO₃ and the mixture was further extracted with DCM. The combined organic layers were filtered through a phase separator and the solvent was removed by evaporation. There was obtained 1.65 g (71%) of 69C as an oil. ¹H NMR (500 MHz, CDCl₃): δ 0.95 (s, 3H), 1.32 (m, 2H), 1.54 (m, 2H), 2.32 (m, 2H), 2.54 (m, 2H), 3.38 (s, 2H), 3.42 (s, 2H), 3.83 (m, 2H), 3.95 (m, 2H), 4.97 (m, 1H), 6.50 (dd, 1H), 6.57 (s, 1H), 7.16 (d, 1H), MS (APCI+) m/z 305 [M+H]⁺.

69. (3-(4-((4-(Hydroxymethyl)-4-methylpiperidin-1-yl)methyl)-3-methylphenoxy)azetidin-1-yl)(5-phenyl-1,3,4-oxadiazol-2-yl)methanone To a solution of 69C (1.65 g, 5.42 mmol) in methanol (25 mL) was added commercially available ethyl 5-phenyl-1,3,4-oxadiazole-2-carboxylate (1.30 g, 5.96 mmol) followed by sodium cyanide (53 mg, 1.10 mmol). The reaction mixture was stirred at RT overnight. The solvent was removed by evaporation and the residue was dissolved in DCM. The solution was washed with NaHCO₃, filtered through a phase separator and then evaporated to near dryness. Ether was added and the formed solid was filtered off and washed with ether. The product was dried in vacuo to afford 1.85 g (72%) of 69 as a crystalline solid, m. p. 167° C. ¹H NMR (500 MHz, CDCl₃): δ 0.96 (s, 3H), 1.31 (m, 2H), 1.52 (m, 2H) 2.28 (m, 2H), 2.34 (s, 3H), 2.51 (m, 2H), 3.38 (s, 2H), 3.40 (s, 2H), 4.31 (dd, 1H), 4.62 (dd, 1H), 4.73 (dd, 1H), 5.05 (m, 1H), 5.13 (m, 1H), 6.54 (dd, 1H), 6.60 (d, 1H), 7.18 (d, 1H), 7.53 (t, 2H), 7.59 (t, 1H), 8.17 (d, 2H), MS (APCI+) m/z 477 [M+H]⁺, LC purity: 99%.

Example 70

(3-(4-((3-Ethyl-3-hydroxyazetidin-1-yl)methyl)phenoxy)azetidin-1-yl)(5-(4-methoxyphenyl)-1,3,4-oxadiazol-2-yl)methanone

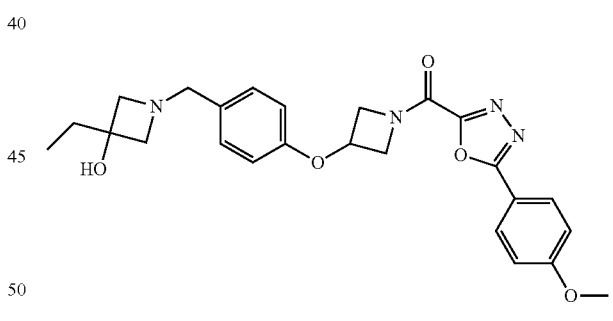

70A. 3-Ethylazetidin-3-ol trifluoroacetate

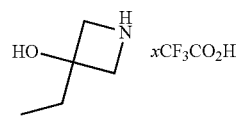

tert-Butyl 3-ethyl-3-hydroxyazetidine-1-carboxylate (2.3 g, 11.43 mmol) was dissolved in DCM (10 mL) and TFA (15 mL) was added. The reaction mixture was stirred at RT for 2.5 h and then the mixture was evaporated. Ethanol was added and the mixture was again evaporated to afford 3.0 g (100%) of 70A. $^1$H NMR (500 MHz, CDCl$_3$): δ 0.96 (t, 3H), 1.81 (q, 2H), 3.94 (m, 4H).

70. (3-(4-((3-Ethyl-3-hydroxyazetidin-1-yl)methyl) phenoxy)azetidin-1-yl)(5-(4-methoxyphenyl)-1,3,4-oxadiazol-2-yl)methanone To a solution of 55A (0.20 g, 0.53 mmol) in DCM (10 mL) was added 70A (0.20 g, 0.93 mmol) followed by DIPEA (0.17 mL, 0.95 mmol). The mixture was stirred at RT for 20 min and then sodium triacetoxyborohydride (0.22 g, 1.05 mmol) was added. The mixture was stirred at RT overnight and then washed with an aqueous solution of Na$_2$CO$_3$. The organic solution was filtered through a phase separator and then the solvent was removed by evaporation. The product was purified on a silica gel column using ethyl acetate and then 5% methanol in DCM where the methanol contained 2M ammonia. There was obtained 128 mg (52%) of 70 as a solid. $^1$H NMR (500 MHz, CDCl$_3$): δ 0.95 (t, 3H), 1.77 (q, 2H), 3.02 (d, 2H), 3.30 (d, 2H), 3.60 (s, 2H), 3.88 (s, 3H), 4.32 (m, 1H), 4.63 (m, 1H), 4.72 (m, 1H), 5.10 (m, 2H), 6.71 (d, 2H), 7.01 (d, 2H), 7.22 (d, 2H), 8.10 (d, 2H), MS (APCI+) m/z 465 [M+H]$^+$, LC purity: 97%.

Example 71

(3-(4-((3-Ethyl-3-hydroxyazetidin-1-yl)methyl)phenoxy)azetidin-1-yl)(5-phenyl-1,3,4-oxadiazol-2-yl)methanone 71A. 4-(1-(5-Phenyl-1,3,4-oxadiazole-2-carbonyl) azetidin-3-yloxy)benzaldehyde

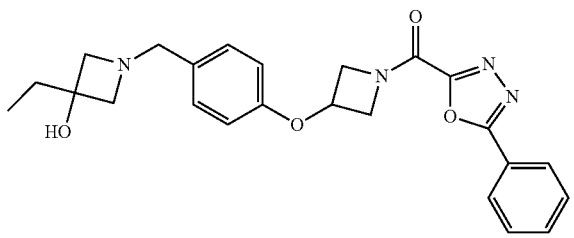 [SMILES: CCC1(O)CN(Cc2ccc(OC3CN(C(=O)c4nnc(-c5ccccc5)o4)C3)cc2)C1]

Intermediate 53B (5.0 g, 15.5 mmol) was dissolved in DMA (40 mL) and 4-hydroxybenzaldehyde (2.17 g, 17.8 mmol) was added followed by Cs$_2$CO$_3$ (5.8 g, 17.8 mmol). The mixture was stirred at 110° C. for 5 h. Water was added and the mixture was extracted trice with DCM. The solution was filtered through a phase separator and the solvent was removed by evaporation. Ether was added to the residue and the formed solid was filtered and washed with ether. The product was dried in vacuo to give 3.58 g (66%) of 71A as a beige solid. $^1$H NMR (500 MHz, CDCl$_3$): δ 4.37 (m, 1H), 4.70 (m, 1H), 4.79 (m, 1H), 5.18 (m, 2H), 6.91 (d, 2H), 7.53 (t, 2H), 7.60 (t, 1H), 7.87 (d, 2H), 8.16 (d, 2H), 9.92 (s, 1H).

71. (3-(4-((3-Ethyl-3-hydroxyazetidin-1-yl)methyl) phenoxy)azetidin-1-yl)(5-phenyl-1,3,4-oxadiazol-2-yl)methanone Using a similar protocol as described in Example 70 employing 71A and 70A as starting materials afforded 185 mg (30%) of 71 as a solid. $^1$H NMR (500 MHz, CDCl$_3$): δ 0.95 (t, 3H), 1.76 (q, 2H), 3.02 (d, 2H), 3.26 (d, 2H), 3.58 (s, 2H), 4.29 (m, 1H), 4.61 (m, 1H), 4.72 (m, 1H), 5.10 (m, 2H), 6.71 (d, 2H), 7.21 (d, 2H), 7.51 (t, 2H), 7.55 (t, 1H), 8.13 (d, 2H), MS (APCI+) m/z 435 [M+H]$^+$, LC purity: 94%.

Example 72

(3-(4-((3-Ethyl-3-hydroxyazetidin-1-yl)methyl)-2-methylphenoxy)azetidin-1-yl)(5-(4-methoxyphenyl)-1,3,4-oxadiazol-2-yl)methanone Using a similar protocol as described in Example 70 employing MA and 70A as starting materials afforded 93 mg (38%) of 72 as a solid. $^1$H NMR (500 MHz, CDCl$_3$): δ 0.95 (t, 3H), 1.77 (q, 2H), 2.23 (s, 3H), 3.02 (d, 2H), 3.29 (d, 2H), 3.57 (s, 2H), 3.89 (s, 3H), 4.33 (m, 1H), 4.65 (m, 1H), 4.72 (m, 1H), 5.07 (m, 1H), 5.11 (m, 1H), 6.44 (d, 1H), 7.05 (m, 4H), 8.09 (d, 2H), MS (APCI+) m/z 479 [M+H]$^+$, LC purity: 99%.

Example 73

(3-(4-((3-Ethyl-3-hydroxyazetidin-1-yl)methyl)-3-methylphenoxy)azetidin-1-yl)(5-(4-methoxyphenyl)-1,3,4-oxadiazol-2-yl)methanone

73A. (3-Hydroxyazetidin-1-yl)(5-(4-methoxyphenyl)-1,3,4-oxadiazol-2-yl)methanone

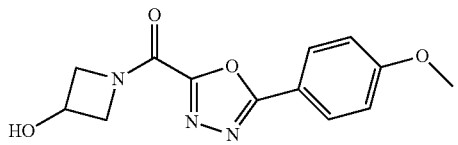 [SMILES: COc1ccc(-c2nnc(C(=O)N3CC(O)C3)o2)cc1]

To a suspension of ethyl 5-(4-methoxyphenyl)-1,3,4-oxadiazole-2-carboxylate—see e.g. *Journal fuer Praktische Chemie*, 327, 109-116 (1985)—(0.50 g, 2.01 mmol) in dry methanol (10 ml) was added sodium cyanide (20 mg, 0.40 mmol). A solution of 3-hydroxyazetidine hydrochloride (0.26 g, 2.42 mmol) in methanol (2 ml) and then triethylamine (0.34 mL, 2.42 mmol) were added at ambient temperature. The reaction mixture was stirred at ambient temperature overnight. Water (20 ml) and dichloromethane (30 ml) were added. Some of the desired product precipitated and was filtered off. The two layers after filtration were separated and the aqueous phase was extracted twice with dichloromethane (30 ml). The combined organic layers were dried over $MgSO_4$ and the solution was evaporated. In total, there was obtained 0.43 g (77%) of 73A as a solid. $^1H$ NMR (400 MHz, DMSO-$d_6$): δ 3.82 (dd, 1H), 3.84 (s, 3H), 4.30 (m, 2H), 4.55 (m, 1H), 4.77 (dd, 1H), 5.85 (d, 1H), 7.16 (d, 2H), 7.98 (d, 2H), MS (APCI+) m/z 276 [M+H]$^+$.

73B. 1-(5-(4-Methoxyphenyl)-1,3,4-oxadiazole-2-carbonyl)azetidin-3-yl methanesulfonate

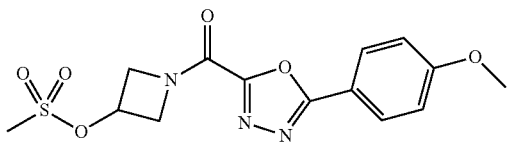

A suspension of 73A (5.45 g, 19.8 mmol) in dichloromethane (100 ml) was cooled in an ice-bath. Triethylamine (4.4 mL, 31.7 mmol) was added followed by methanesulfonyl chloride (2.3 mL, 29.7 mmol). After the addition, the cooling bath was removed. The mixture was stirred for 7 h. The mixture was transferred to a reparatory funnel and was washed with water followed by aqueous $NaHCO_3$ (sat.). The organic solution was dried (phase separator) and evaporated. Dichloromethane (50 mL) and diethyl ether (200 mL) were added and the solid product was filtered. The product was washed twice with diethyl ether and then dried in vacuo. There was obtained 5.03 g (72%) of 73B as a solid. $^1H$ NMR (500 MHz, CDCl$_3$): δ 3.13 (s, 3H), 3.90 (s, 3H), 4.42 (dd, 1H), 4.64 (dd, 1H), 4.86 (dd, 1H), 5.11 (dd, 1H), 5.40 (m, 1H), 7.02 (d, 2H), 8.09 (d, 2H), MS (APCI+) m/z 354 [M+H]$^+$.

73C. 4-(1-(5-(4-Methoxyphenyl)-1,3,4-oxadiazole-2-carbonyl)azetidin-3-yloxy)-2-methylbenzaldehyde

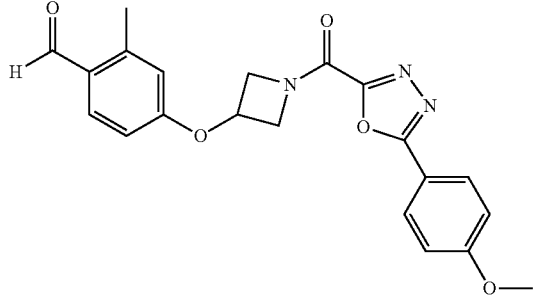 [SMILES: COc1ccc(-c2nnc(C(=O)N3CC(Oc4ccc(C=O)c(C)c4)C3)o2)cc1]

Using a similar protocol as described in Example 71A employing 73B and 4-hydroxy-2-methylbenzaldehyde as starting materials afforded 9.4 g (67%) of 73C as a solid. $^1H$ NMR (500 MHz, CDCl$_3$): δ 2.67 (s, 3H), 3.89 (s, 3H), 4.37 (m, 1H), 4.70 (m, 1H), 4.78 (m, 1H), 5.15 (m, 2H), 6.65 (s, 1H), 6.74 (d, 1H), 7.02 (d, 2H), 7.78 (d, 1H), 8.11 (d, 2H), 10.2 (s, 1H).

73. (3-(4-((3-Ethyl-3-hydroxyazetidin-1-yl)methyl)-3-methylphenoxy)azetidin-1-yl)(5-(4-methoxyphenyl)-1,3,4-oxadiazol-2-yl)methanone Using a similar protocol as described in Example 70 employing 73C and 70A as starting materials afforded 100 mg (41%) of 73 as a solid. $^1H$ NMR (500 MHz, CDCl$_3$): δ 0.98 (t, 3H), 1.80 (q, 2H), 2.30 (s, 3H), 2.98 (m, 2H), 3.33 (d, 2H), 3.57 (s, 2H), 3.89 (s, 3H), 4.32 (m, 1H), 4.63 (m, 1H), 4.73 (m, 1H), 5.05 (m, 1H), 5.11 (m, 1H), 6.54 (d, 1H), 6.59 (s, 1H), 7.03 (d, 2H), 7.16 (d, 1H), 8.10 (d, 2H), MS (APCI+) m/z 479 [M+H]$^+$, LC purity: 96%.

Example 74

(3-(4-((3-Ethyl-3-hydroxyazetidin-1-yl)methyl)-2-methylphenoxy)azetidin-1-yl)(5-phenyl-1,3,4-oxadiazol-2-yl)methanone

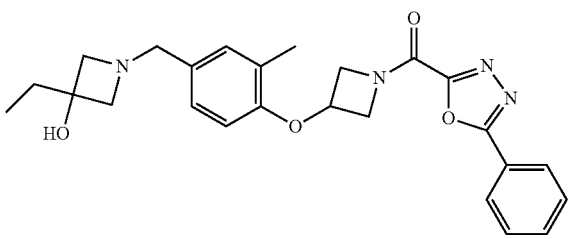 [SMILES: CCC1(O)CN(Cc2ccc(OC3CN(C(=O)c4nnc(-c5ccccc5)o4)C3)c(C)c2)C1]

74A. 3-Methyl-4-(1-(5-Phenyl-1,3,4-oxadiazole-2-carbonyl)azetidin-3-yloxy)benzaldehyde

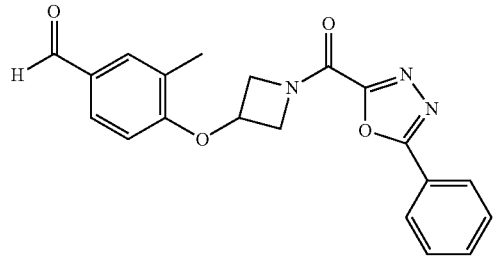 [SMILES: Cc1cc(C=O)ccc1OC1CN(C(=O)c2nnc(-c3ccccc3)o2)C1]

Using a similar protocol as described in Example 71A employing 53B and 4-hydroxy-3-methylbenzaldehyde as starting materials afforded 0.8 g (28%) of 74A as a solid. $^1$H NMR (500 MHz, CDCl$_3$): δ 2.33 (s, 3H), 4.40 (m, 1H), 4.71 (m, 1H), 4.82 (m, 1H), 5.19 (m, 2H), 6.61 (s, 1H), 7.54 (t, 2H), 7.60 (t, 1H), 7.73 (d, 1H), 7.75 (s, 1H), 8.18 (d, 2H), 9.89 (s, 1H).

74. (3-(4-((3-Ethyl-3-hydroxyazetidin-1-yl)methyl)-2-methylphenoxy)azetidin-1-yl)(5-phenyl-1,3,4-oxadiazol-2-yl)methanone Using a similar protocol as described in Example 70 employing 74A and 70A as starting materials afforded 35 mg (11%) of 74 as a solid. $^1$H NMR (500 MHz, CDCl$_3$): δ 0.95 (t, 3H), 1.78 (q, 2H), 2.24 (s, 3H), 3.01 (d, 2H), 3.31 (d, 2H), 3.57 (s, 2H), 4.35 (m, 1H), 4.68 (m, 1H), 4.75 (m, 1H), 5.07 (m, 1H), 5.12 (m, 1H), 6.45 (d, 1H), 7.06 (d, 1H), 7.11 (s, 1H), 7.52 (t, 2H), 7.60 (t, 1H), 8.16 (d, 1H), MS (APCI+) m/z 449 [M+H]$^+$, LC purity: 97%.

Example 75

(3-(4-((3-Ethyl-3-hydroxyazetidin-1-yl)methyl)-3-methylphenoxy)azetidin-1-yl)(5-phenyl-1,3,4-oxadiazol-2-yl)methanone

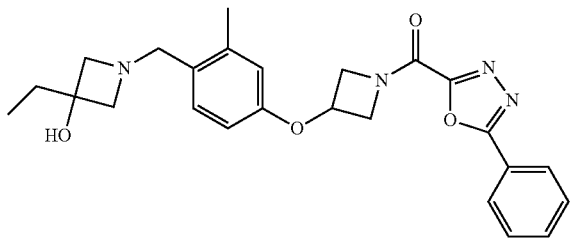 [SMILES: CCC1(O)CN(Cc2ccc(OC3CN(C(=O)c4nnc(-c5ccccc5)o4)C3)cc2C)C1]

Using a similar protocol as described in Example 70 employing 53C and 70A as starting materials afforded 189 mg (50%) of 75 as a solid. $^1$H NMR (600 MHz, DMSO-d$_6$): δ 0.84 (t, 3H), 1.59 (q, 2H), 2.21 (s, 3H), 2.79 (d, 2H), 3.16 (d, 2H), 3.46 (s, 2H), 4.04 (m, 1H), 4.48 (m, 1H), 4.59 (m, 1H), 4.97 (s, 1H), 5.05 (m, 2H), 6.62 (d, 1H), 6.66 (s, 1H), 7.12 (d, 1H), 7.62 (t, 2H), 7.66 (t, 1H), 8.04 (d, 2H), MS (APCI+) m/z 449 [M+H]$^+$, LC purity: 91%.

Example 76

(3-(4-((3-Hydroxy-3-methylazetidin-1-yl)methyl)phenoxy)azetidin-1-yl)(5-(4-methoxyphenyl)-1,3,4-oxadiazol-2-yl)methanone

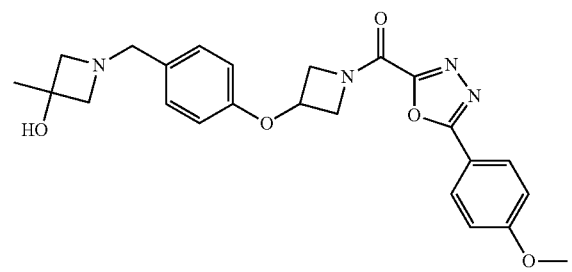

Using a similar protocol as described in Example 70 employing 55A and 3-methylazetidin-3-ol hydrochloride as starting materials afforded 124 mg (52%) of 76 as a solid. $^1$H NMR (500 MHz, CDCl$_3$): δ 1.45 (s, 3H), 3.42 (d, 2H), 3.56 (d, 2H), 3.77 (s, 2H), 3.89 (s, 3H), 4.31 (m, 1H), 4.65 (m, 1H), 4.76 (m, 1H), 5.08 (m, 1H), 5.13 (m, 1H), 6.78 (d, 2H), 7.02 (d, 2H), 7.29 (d, 2H), 8.10 (d, 2H), MS (APCI+) m/z 451 [M+H]$^+$, LC purity: 96%.

Example 77

(3-(4-((3-Hydroxy-3-methylazetidin-1-yl)methyl)phenoxy)azetidin-1-yl)(5-phenyl-1,3,4-oxadiazol-2-yl)methanone

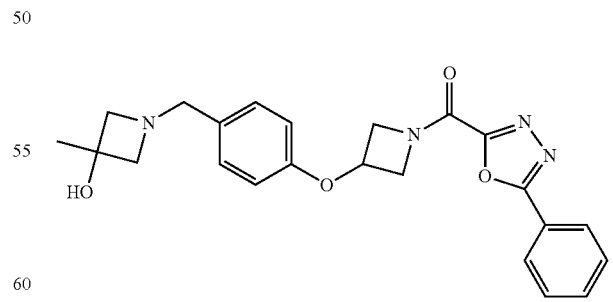

Using a similar protocol as described in Example 70 employing 71A and 3-methylazetidin-3-ol hydrochloride as starting materials afforded 20 mg (16%) of 77 as a solid. $^1$H NMR (500 MHz, CDCl$_3$): δ 1.50 (s, 3H), 3.14 (d, 2H), 3.33 (d, 2H), 3.63 (s, 2H), 4.32 (m, 1H), 4.64 (m, 1H), 4.76 (m, 1H), 5.05 (m, 1H), 5.12 (m, 1H), 6.74 (d, 2H), 7.24 (d, 2H), 7.53 (t, 2H), 7.59 (t, 1H), 8.16 (d, 2H), MS (APCI+) m/z 421 [M+H]+, LC purity: 88%.

7.35 (s, 1H), 7.53 (t, 2H), 7.59 (t, 1H), 8.16 (d, 2H), MS (APCI+) m/z 455 [M+H]+, LC purity: 93%.

Example 78

(3-(2-Chloro-4-((3-hydroxy-3-methylazetidin-1-yl)methyl)phenoxy)azetidin-1-yl)(5-phenyl-1,3,4-oxadiazol-2-yl)methanone

Example 79

(3-(2-Chloro-4-((3-hydroxy-3-methylazetidin-1-yl)methyl)phenoxy)azetidin-1-yl)(5-(4-methoxyphenyl)-1,3,4-oxadiazol-2-yl)methanone

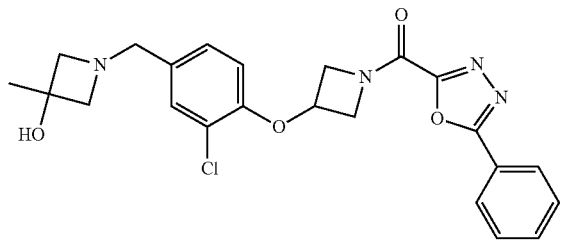 [SMILES: CC1(O)CN(Cc2ccc(OC3CN(C(=O)c4nnc(-c5ccccc5)o4)C3)c(Cl)c2)C1]
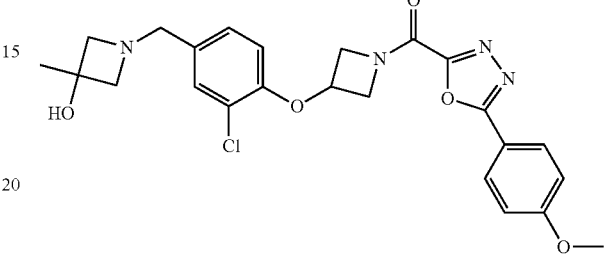

78A. 3-Chloro-4-(1-(5-phenyl-1,3,4-oxadiazole-2-carbonyl)azetidin-3-yloxy)benzaldehyde 79A. 3-Chloro-4-(1-(5-(4-methoxyphenyl)-1,3,4-oxadiazole-2-carbonyl)azetidin-3-yloxy)benzaldehyde

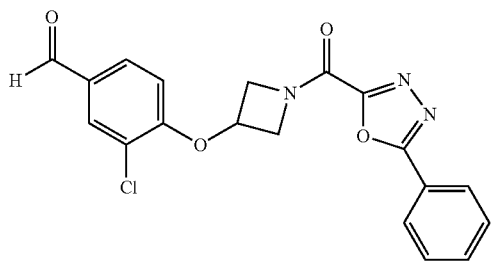 [SMILES: O=Cc1ccc(OC2CN(C(=O)c3nnc(-c4ccccc4)o3)C2)c(Cl)c1]

Using a similar protocol as described in Example 71A employing 53B and 3-chloro-4-hydroxybenzaldehyde as starting materials afforded 51 mg (10%) of 78A as a solid. ¹H NMR (500 MHz, CDCl₃): δ 4.44 (m, 1H), 4.75 (m, 1H), 4.87 (m, 1H), 5.22 (m, 2H), 6.75 (s, 1H), 7.53 (t, 2H), 7.61 (t, 1H), 7.80 (d, 1H), 7.98 (s, 1H), 8.18 (d, 2H), 9.90 (s, 1H).

78. (3-(2-Chloro-4-((3-hydroxy-3-methylazetidin-1-yl)methyl)phenoxy)azetidin-1-yl)(5-phenyl-1,3,4-oxadiazol-2-yl)methanone Using a similar protocol as described in Example 70 employing 78A and 3-methylazetidin-3-ol hydrochloride as starting materials afforded 34 mg (56%) of 78 as a solid. ¹H NMR (500 MHz, CDCl₃): δ 1.50 (s, 3H), 3.07 (d, 2H), 3.30 (d, 2H), 3.57 (s, 2H), 4.39 (m, 1H), 4.65 (m, 1H), 4.81 (m, 1H), 5.13 (m, 2H), 5.29 (s, 1H), 6.59 (m, 2H), 7.13 (d, 1H), Using a similar protocol as described in Example 71A employing 73B and 3-chloro-4-hydroxybenzaldehyde as starting materials afforded 80 mg (15%) of 79A as a solid. ¹H NMR (500 MHz, CDCl₃): δ 3.89 (s, 3H), 4.43 (m, 1H), 4.74 (m, 1H), 4.85 (m, 1H), 5.21 (m, 2H), 6.75 (s, 1H), 7.02 (d, 2H), 7.79 (d, 1H), 7.97 (s, 1H), 8.11 (d, 2H), 9.89 (s, 1H).

79. (3-(2-Chloro-4-((3-hydroxy-3-methylazetidin-1-yl)methyl)phenoxy)azetidin-1-yl)(5-phenyl-1,3,4-oxadiazol-2-yl)methanone Using a similar protocol as described in Example 70 employing 79A and 3-methylazetidin-3-ol hydrochloride as starting materials afforded 29 mg (31%) of 79 as a solid. ¹H NMR (500 MHz, CDCl₃): δ 1.51 (s, 3H), 3.04 (d, 2H), 3.28 (d, 2H), 3.57 (s, 2H), 3.89 (s, 3H), 4.41 (m, 1H), 4.65 (m, 1H), 4.80 (m, 1H), 5.10 (m, 2H), 5.30 (s, 1H), 7.01 (d, 2H), 7.13 (s, 1H), 7.36 (s, 1H), 8.09 (d, 2H), MS (APCI+) m/z 485 [M+H]+, LC purity: 88%.

Example 80

(3-(4-((3-Hydroxy-3-methylazetidin-1-yl)methyl)-3-methylphenoxy)azetidin-1-yl)(5-(4-methoxyphenyl)-1,3,4-oxadiazol-2-yl)methanone

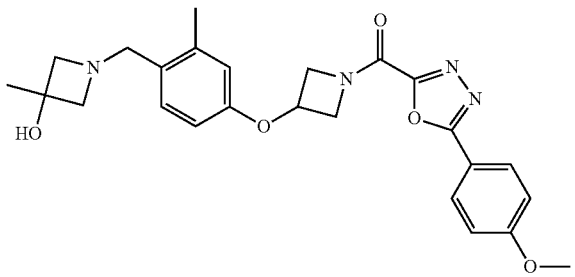

73C (0.12 g, 0.31 mmol) and 3-methylazetidin-3-ol hydrochloride (0.041 g, 0.34 mmol) were mixed with DCM (3 ml). Triethylamine (0.085 ml, 0.61 mmol) and then sodium triacetoxyborohydride (0.129 g, 0.61 mmol) were added. The mixture was stirred at RT overnight and then diluted with DCM (10 ml). The mixture was washed with aqueous NaHCO$_3$ (sat. 4 ml) and then the organic solution was filtered through a phase separator. The solvent was removed by evaporation and the residue was purified by silica gel chromatography eluting the product with 1-2% methanol in DCM where the methanol contained ammonia (2 M). The product was triturated from DCM/diethyl ether. There was obtained 81 mg (57%) of the title compound which was recrystallised from ethyl acetate to give a crystalline solid m. p. 121° C., 137° C. and 145° C. $^1$H NMR (500 MHz, CDCl$_3$): δ 1.51 (s, 3H), 2.30 (s, 3H), 3.01 (d, 2H), 3.30 (d, 2H), 3.56 (s, 2H), 3.89 (s, 3H), 4.30 (m, 1H), 4.62 (m, 1H), 4.72 (m, 1H), 5.03 (m, 1H), 5.10 (m, 1H), 6.53 (d, 1H), 6.60 (s, 1H), 7.03 (d, 2H), 7.16 (d, 1H), 8.09 (d, 2H), MS (APCI+) m/z 465 [M+H]+, LC purity: 97%.

Example 81

(3-(4-((4-Fluoro-4-(hydroxymethyl)piperidin-1-yl)methyl)phenoxy)azetidin-1-yl)(5-(4-methoxyphenyl)-1,3,4-oxadiazol-2-yl)methanone

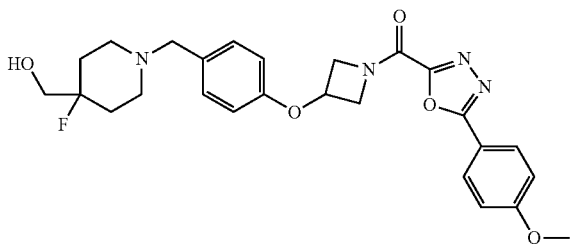 [SMILES: COc1ccc(-c2nnc(C(=O)N3CC(Oc4ccc(CN5CCC(F)(CO)CC5)cc4)C3)o2)cc1]

81A. (4-Fluoropiperidin-4-yl)methanol hydrochloride

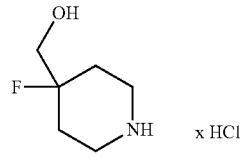

To a stirred solution of tert-butyl 4-fluoro-4-(hydroxymethyl)piperidine-1-carboxylate (21 g, 0.09 mol) in dry ether (200 mL) was added HCl/ether (4M, 100 mL) drop-wise at 0° C. under N$_2$. After addition, the mixture was allowed to warm to RT and stirred overnight. The reaction mixture was concentrated to remove solvent and the residue was washed with ether. $^1$H NMR (400 MHz, D$_2$O): δ 1.78 (m, 2H), 2.05 (m, 2H), 3.15 (m, 2H), 3.31 (m, 2H), 3.57 (d, 2H), m/z 134 [M+H]+.

81. (3-(4-((4-Fluoro-4-(hydroxymethyl)piperidin-1-yl)methyl)phenoxy)azetidin-1-yl)(5-(4-methoxyphenyl)-1,3,4-oxadiazol-2-1 methanone Using a similar protocol as described in Example 70 employing 55A and 81A as starting materials afforded 21 mg (16%) of 81 as a solid. $^1$H NMR (500 MHz, CDCl$_3$): δ 1.60 (m, 4H), 2.15 (m, 2H), 2.57 (m, 2H), 3.36 (m, 2H), 3.83 (s, 2H), 4.05 (m, 1H), 4.50 (m, 1H), 4.59 (m, 1H), 4.88 (m, 2H), 5.08 (m, 1H), 6.82 (d, 2H), 7.15 (d, 2H), 7.22 (m, 2H), 7.98 (d, 2H), MS (APCI+) m/z 497 [M+H]+, LC purity: 95%.

Example 82

(3-(4-((4-(Hydroxymethyl)-4-methylpiperidin-1-yl)methyl)-3-methylphenoxy)azetidin-1-yl)(5-(4-methoxyphenyl)-1,3,4-oxadiazol-2-yl)methanone

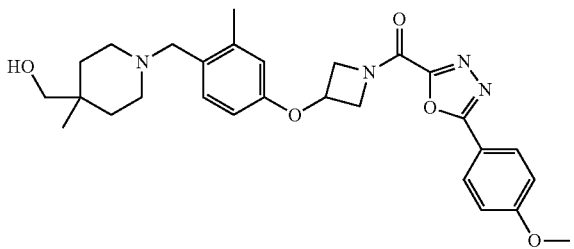 [SMILES: COc1ccc(-c2nnc(C(=O)N3CC(Oc4ccc(CN5CCC(C)(CO)CC5)c(C)c4)C3)o2)cc1]

73C (0.12 g, 0.31 mmol) and (4-methylpiperidin-4-yl)methanol hydrochloride (0.051 g, 0.31 mmol) were mixed with DCM (3 ml). Triethylamine (0.085 ml, 0.61 mmol) and then sodium triacetoxyborohydride (0.129 g, 0.61 mmol) were added. The mixture was stirred at RT overnight and then diluted with DCM (10 ml). The mixture was washed with aqueous NaHCO$_3$ (sat. 4 ml) and then the organic solution was filtered through a phase separator. The solvent was removed by evaporation and the residue was purified by silica gel chromatography eluting the product with 1-3% methanol in DCM where the methanol contained ammonia (2 M). The product was triturated from DCM/diethylether. There was obtained 102 mg (66%) of the title compound as a solid. $^1$H NMR (500 MHz, CDCl$_3$): δ 0.95 (s, 3H), 1.32 (m, 2H), 1.53

(m, 2H), 2.30 (m, 2H), 2.34 (s, 3H), 2.53 (m, 2H), 3.38 (m, 2H), 3.42 (s, 2H), 3.89 (s, 3H), 4.32 (m, 1H), 4.63 (m, 1H), 4.72 (m, 1H), 5.04 (m, 2H), 5.10 (m, 1H), 6.55 (d, 2H), 6.59 (s, 1H), 7.03 (d, 2H), 7.19 (m, 2H), 8.10 (d, 2H), MS (APCI+) m/z 507 [M+H]+, LC purity: 98%.

Example 83

(3-(4-((4-(Hydroxymethyl)-4-methylpiperidin-1-yl)methyl)phenoxy)azetidin-1-yl)(5-(4-methoxyphenyl)-1,3,4-oxadiazol-2-yl)methanone

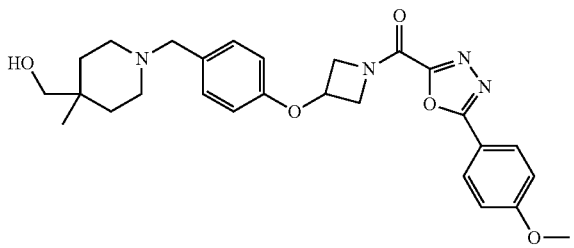

To a solution of 55A (5.03 g, 13.3 mmol) in DCM (250 mL) was added (4-methylpiperidin-4-yl)methanol hydrochloride (2.4 g, 14.6 mmol) followed by DIPEA (2.5 mL, 14.6 mmol). The mixture was stirred at RT for 20 min before the addition of sodium triacetoxyborohydride (5.6 g, 26.5 mmol) and MeOH (5 mL). The reaction mixture was stirred at RT overnight. Further (4-methylpiperidin-4-yl)methanol (360 mg, 2.7 mmol), DIPEA (0.5 ml) and sodium triacetoxyborohydride (1.1 g, 5.2 mmol) were added and the mixture was stirred at RT for 3 days. Even more sodium triacetoxyborohydride (2 g, 9.5 mmol) was added and the mixture was stirred for another 2 h. Yet another portion of sodium triacetoxyborohydride (4 g, 19 mmol) was added and the mixture was left at RT overnight. The mixture was then washed with a saturated aqueous solution of $Na_2CO_3$. The organic layer was filtered through a phase separator and the solvent was removed by evaporation. The crude product was purified by flash chromatography starting with EtOAc and then eluting the product with 5% methanol in DCM where the methanol contained ammonia (2 M). The pure fractions were combined and evaporated. The residue was triturated with diethyl ether and there was obtained 3.55 g (54%) of the product as a crystalline solid, m. p. 102° C. and 146° C. $^1$H NMR (500 MHz, $CDCl_3$): δ 0.94 (s, 3H), 1.33 (m, 2H), 1.55 (m, 2H), 2.28 (m, 2H), 2.53 (m, 2H), 3.37 (m, 2H), 3.47 (s, 2H), 3.88 (s, 3H), 4.33 (m, 1H), 4.62 (m, 1H), 4.72 (m, 1H), 5.06 (m, 1H), 5.11 (m, 1H), 6.71 (d, 2H), 7.00 (d, 2H), 7.26 (m, 2H), 8.08 (d, 2H), MS (APCI+) m/z 493 [M+H]+, LC purity: 97%.

Example 84

(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone

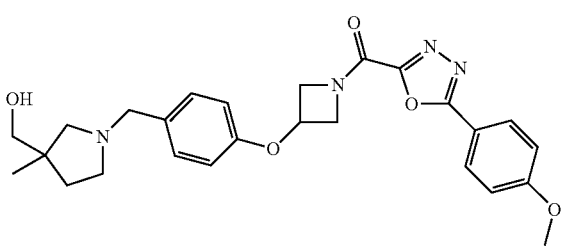 [SMILES: COc1ccc(-c2nnc(C(=O)N3CC(Oc4ccc(CN5CCC(C)(CO)C5)cc4)C3)o2)cc1]

84A. (3-methylpyrrolidin-3-yl)methanol hydrochloride

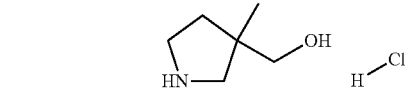

tert-butyl 3-(hydroxymethyl)-3-methylpyrrolidine-1-carboxylate (0.31 g, 1.44 mmol, see WO 2009132986) was dissolved in HCl in methanol (1.25M, 3.5 mL, 4.32 mmol). The reaction mixture was stirred at RT overnight and then the mixture was evaporated. Ethanol was added and the mixture was again evaporated to afford 243 mg. The crude product was used in the next step without further purification.

84. (3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone Intermediate 55A (0.165 g, 0.43 mmol), intermediate 84A (3-methylpyrrolidin-3-yl)methanol hydrochloride (0.099 g, 0.65 mmol) and TEA (0.241 mL, 1.74 mmol) were mixed in dichloromethane (4 mL). The mixture was stirred at RT for 30 min and then sodium triacetoxyhydroborate (0.184 g, 0.87 mmol) was added and the mixture was stirred at RT overnight. Aqueous $NaHCO_3$ (sat., 4 mL) and dichloromethane (4 mL) were added and the mixture was filtered through a phase separator and the solvent was removed by evaporation. The product was purified by preparative reverse-phase HPLC at pH 10 than re-purified at pH3 to give 21 mg (10%). $^1$H NMR (600 MHz, DMSO) δ 1.01 (s, 3H), 1.31-1.39 (m, 1H), 1.57-1.65 (m, 1H), 2.07 (d, 1H), 2.43-2.49 (m, 2H), 3.13-3.25 (m, 3H), 3.46-3.53 (m, 2H), 3.88 (s, 3H), 4.06-4.14 (m, 1H), 4.51-4.67 (m, 2H), 5.05-5.19 (m, 2H), 6.85 (d, 2H), 7.15-7.31 (m, 4H), 8.02 (d, 2H), LC purity: 93%.

It will be appreciated by those skilled in the art that the title compound is chiral. The individual enantiomers:
(+)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone; and (−)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;

were obtained by chiral chromatography by using a Chiralpak® IA column (supplied by Chiral Technologies Europe) at 40° C. using a mobile phase comprising heptane/THF/triethylamine 65/35/0.2 and a UV wavelength of 315 nM to detect the products.

First fraction E1 (−)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone optical rotation −10.8° [c.1.0, ACN] (EE=99.3%) ($IC_{50}$ 28 nM).

Second fraction E2 (+)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone optical rotation +9.7° [c.1.0, ACN] (EE=83.8%) ($IC_{50}$ 24 nM).

Example 85

(3-(4-((3-(hydroxymethyl)-3-methylpyrrolidin-1-yl)methyl)phenoxy)azetidin-1-yl)(5-phenyl-1,3,4-oxadiazol-2-yl)methanone

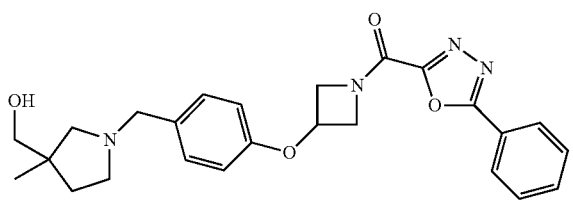 [SMILES: CC1(CO)CCN(Cc2ccc(OC3CN(C(=O)c4nnc(-c5ccccc5)o4)C3)cc2)C1]

Intermediate 71A (0.15 g, 0.43 mmol), intermediate 84A (0.098 g, 0.64 mmol) and TEA (0.238 mL, 1.72 mmol) were mixed in dichloromethane (4 mL). The mixture was stirred at RT for 30 min and then sodium triacetoxyhydroborate (0.182 g, 0.86 mmol) was added and the mixture was stirred at RT overnight. Aqueous $NaHCO_3$ (sat., 4 mL) and dichloromethane (4 mL) were added and the mixture was filtered through a phase separator and the solvent was removed by evaporation. The product was purified by preparative reverse-phase HPLC at pH 10 to give 21 mg (11%). $^1$H NMR (600 MHz, DMSO) δ 1.00 (s, 3H), 1.3-1.39 (m, 1H), 1.57-1.64 (m, 1H), 2.05 (d, 1H), 2.41-2.48 (m, 2H), 3.14-3.24 (m, 2H), 3.43-3.51 (m, 2H), 4.07-4.14 (m, 1H), 4.54-4.73 (m, 3H), 5.07-5.19 (m, 2H), 6.85 (d, 2H), 7.25 (d, 2H), 7.63-7.73 (m, 3H), 8.09 (d, 2H), LC purity: 94%.

It will be appreciated by those skilled in the art that the title compound is chiral. The individual enantiomers:

(+)(3-(4-((3-(hydroxymethyl)-3-methylpyrrolidin-1-yl)methyl)phenoxy)azetidin-1-yl)(5-phenyl-1,3,4-oxadiazol-2-yl)methanone; and (−)(3-(4-((3-(hydroxymethyl)-3-methylpyrrolidin-1-yl)methyl)phenoxy)azetidin-1-yl)(5-phenyl-1,3,4-oxadiazol-2-yl)methanone;

are obtained by chiral chromatography for example as described in Example 84.

Example 86

(3-(4-((4-hydroxyazepan-1-yl)methyl)phenoxy)azetidin-1-yl)(5-(4-methoxyphenyl)-1,3,4-oxadiazol-2-yl)methanone

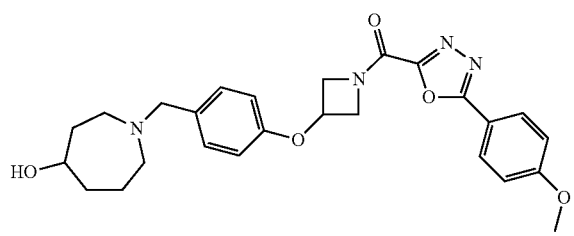 [SMILES: COc1ccc(-c2nnc(C(=O)N3CC(Oc4ccc(CN5CCCC(O)CC5)cc4)C3)o2)cc1]

Intermediate 55A (0.10 g, 0.26 mmol), azepan-4-ol hydrochloride (0.052 g, 0.34 mmol, see WO 2011019090) and TEA (0.146 mL, 1.05 mmol) were mixed in dichloromethane (4 mL). The mixture was stirred at RT for 1 h and then sodium triacetoxyhydroborate (0.112 g, 0.53 mmol) was added and the mixture was stirred at RT overnight. Aqueous $NaHCO_3$ (sat., 3 mL) and dichloromethane (3 mL) were added and the mixture was filtered through a phase separator and the solvent was removed by evaporation. The product was purified by preparative reverse-phase HPLC at pH 10 to give 88 mg (70%). $^1$H NMR (600 MHz, DMSO) δ 1.38-1.85 (m, 7H), 2.37-2.65 (m, 3H), 3.53 (s, 2H), 3.71-3.77 (m, 1H), 3.88 (s, 3H), 4.05-4.14 (m, 1H), 4.31-4.46 (m, 1H), 4.5-4.67 (m, 2H), 5.05-5.2 (m, 2H), 6.85 (d, 2H), 7.17-7.29 (m, 4H), 8-8.05 (m, 2H), LC purity: 94%.

It will be appreciated by those skilled in the art that the title compound is chiral. The individual enantiomers:

(+)(3-(4-((4-hydroxyazepan-1-yl)methyl)phenoxy)azetidin-1-yl)(5-(4-methoxyphenyl)-1,3,4-oxadiazol-2-yl)methanone and (−)(3-(4-((4-hydroxyazepan-1-yl)methyl)phenoxy)azetidin-1-yl)(5-(4-methoxyphenyl)-1,3,4-oxadiazol-2-yl)methanone are obtained by chiral chromatography for example as described in Example 84.

Example 87

(3-(4-((4-hydroxy-4-methylazepan-1-yl)methyl)phenoxy)azetidin-1-yl)(5-phenyl-1,3,4-oxadiazol-2-yl)methanone

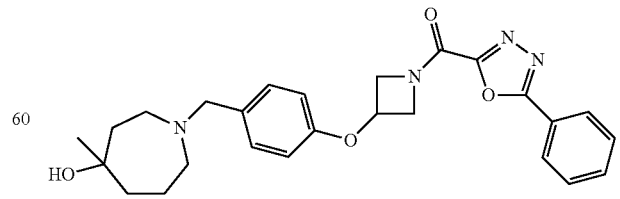

Intermediate 71A (0.15 g, 0.43 mmol), (0.098 g, 0.64 mmol) 4-methylazepan-4-ol hydrochloride (0.062 g, 1.15 mmol, see *Helvetica Chimica Acta*, 45, 1823-32, (1962)) and TEA (0.159 mL, 1.15 mmol) were mixed in dichloromethane (4 mL). The mixture was stirred at RT for 30 min and then sodium triacetoxyhydroborate (0.182 g, 0.86 mmol) was added and the mixture was stirred at RT overnight. Aqueous NaHCO₃ (sat., 3 mL) and dichloromethane (3 mL) were added and the mixture was filtered through a phase separator and the solvent was removed by evaporation. The product was purified twice by preparative reverse-phase HPLC at pH 10 to give 53 mg (40%). ¹H NMR (600 MHz, DMSO) δ 1.11 (s, 3H), 1.35-1.45 (m, 1H), 1.55-1.74 (m, 5H), 2.32-2.64 (m, 4H), 3.46-3.55 (m, 2H), 4.04-4.16 (m, 1H), 4.52-4.67 (m, 2H), 5.05-5.2 (m, 2H), 6.85 (d, 2H), 7.25 (d, 2H), 7.61-7.73 (m, 3H), 8.05-8.11 (m, 2H), LC purity: 96%.

It will be appreciated by those skilled in the art that the title compound is chiral. The individual enantiomers:
(+)(3-(4-((4-hydroxy-4-methylazepan-1-yl)methyl)phenoxy)azetidin-1-yl)(5-phenyl-1,3,4-oxadiazol-2-yl)methanone and
(−)(3-(4-((4-hydroxy-4-methylazepan-1-yl)methyl)phenoxy)azetidin-1-yl)(5-phenyl-1,3,4-oxadiazol-2-yl)methanone are obtained by chiral chromatography for example as described in Example 84.

Example 88

(3-(4-((4-hydroxy-4-methylazepan-1-yl)methyl)phenoxy)azetidin-1-yl)(5-(4-methoxyphenyl)-1,3,4-oxadiazol-2-yl)methanone

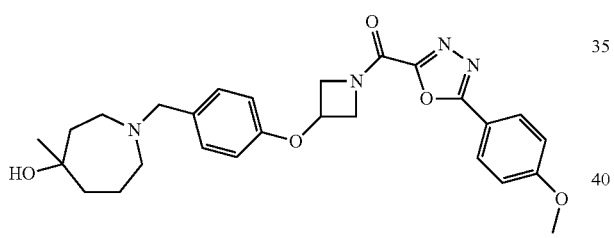

Intermediate 55A (0.10 g, 0.26 mmol), 4-methylazepan-4-ol hydrochloride (0.057 g, 0.34 mmol, see *Helvetica Chimica Acta*, 45, 1823-32, (1962)) and TEA (0.146 mL, 1.05 mmol) were mixed in dichloromethane (4 mL). The mixture was stirred at RT for 1 h and then sodium triacetoxyhydroborate (0.112 g, 0.53 mmol) was added and the mixture was stirred at RT overnight. Aqueous NaHCO₃ (sat., 3 mL) and dichloromethane (3 mL) were added and the mixture was filtered through a phase separator and the solvent was removed by evaporation. The product was purified by preparative reverse-phase HPLC at pH 10 to give 83 mg (64%). ¹H NMR (600 MHz, DMSO) δ 1.11 (s, 3H), 1.35-1.8 (m, 7H), 2.31-2.65 (m, 3H), 3.51 (s, 2H), 3.88 (s, 3H), 4.07-4.12 (m, 1H), 4.51-4.66 (m, 2H), 5.06-5.18 (m, 2H), 6.85 (d, 2H), 7.16-7.3 (m, 4H), 8-8.06 (m, 2H), LC-purity: 92%.

It will be appreciated by those skilled in the art that the title compound is chiral. The individual enantiomers:
(+)(3-(4-((4-hydroxy-4-methylazepan-1-yl)methyl)phenoxy)azetidin-1-yl)(5-(4-methoxyphenyl)-1,3,4-oxadiazol-2-yl)methanone and
(−)(3-(4-((4-hydroxy-4-methylazepan-1-yl)methyl)phenoxy)azetidin-1-yl)(5-(4-methoxyphenyl)-1,3,4-oxadiazol-2-yl)methanone are obtained by chiral chromatography for example as described in Example 84.

Example 89

(3-(4-((4-(hydroxymethyl)piperidin-1-yl)methyl)phenoxy)azetidin-1-yl)(5-(4-methoxyphenyl)-1,3,4-oxadiazol-2-yl)methanone

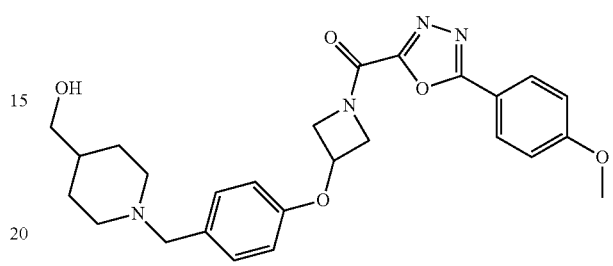

Piperidin-4-ylmethanol (0.04 g, 0.35 mmol) was dissolved in dichloromethane (2 mL) and TEA (0.052 ml, 0.38 mmol) was added. Intermediate 55A (0.11 g, 0.29 mmol) was added followed by addition of sodium triacetoxyhydroborate (0.123 g, 0.58 mmol). The mixture was stirred at RT overnight. Dichloromethane (10 mL) and NaHCO₃ (sat. 2 mL) were added and the mixture was filtered through a phase separator and the solvent was removed by evaporation. The product was purified by preparative reverse-phase HPLC at pH 10 to give 81 mg (58%). ¹H NMR (600 MHz, DMSO) δ 1.05-1.17 (m, 2H), 1.28-1.39 (m, 1H), 1.57-1.66 (m, 2H), 1.82-1.92 (m, 2H), 2.75-2.84 (m, 2H), 3.19-3.27 (m, 3H), 3.83-3.92 (m, 3H), 4.06-4.13 (m, 1H), 4.37-4.45 (m, 1H), 4.5-4.67 (m, 2H), 5.04-5.19 (m, 2H), 6.85 (d, 2H), 7.16-7.27 (m, 4H), 8-8.05 (m, 2H), MS (APCI+) m/z 479 [M+H]⁺, LC-purity: 99%.

Example 90

(3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone

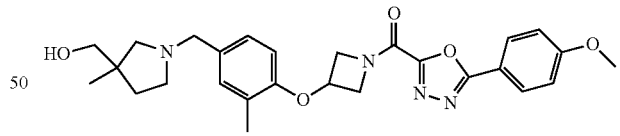

Intermediate 84A (0.095 g, 0.63 mmol) was dissolved in dichloromethane (6 mL), THF (1 mL) and TEA (0.106 mL, 0.76 mmol). Intermediate 74A (0.120 g, 0.31 mmol) was added and the mixture stirred at RT for 5 min. and then sodium triacetoxyhydroborate (0.129 g, 0.61 mmol) was added. The mixture was stirred at RT for 21 h. Aqueous NaHCO₃ (8%, 6 mL) was added and the mixture was filtered through a phase separator, dichloromethane (4 mL) was added and the solvent was removed by evaporation. The product was purified by preparative HPLC under basic conditions followed by lyophilisation to give (0.106 g, 71%). ¹H NMR (400 MHz, CDCl₃) δ 1.01 (s, 3H), 1.57-1.71 (m, 1H), 1.95-2.42 (m, 6H), 2.8-3.09 (m, 2H), 3.3-3.41 (m, 1H), 3.44-3.59 (m, 3H), 3.89 (s, 3H), 4.27-4.38 (m, 1H), 4.59-4.83 (m, 2H), 5-5.22 (m, 2H), 6.44 (d, 1H), 6.96-7.17 (m, 4H), 8.10 (d, 2H), MS (APCI+) m/z 493 [M+H]+, LC Purity: 91%.

It will be appreciated by those skilled in the art that the title compound is chiral. The individual enantiomers:

(+)(3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone and (−)(3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone are obtained by chiral chromatography for example as described in Example 84.

Example 91

(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone

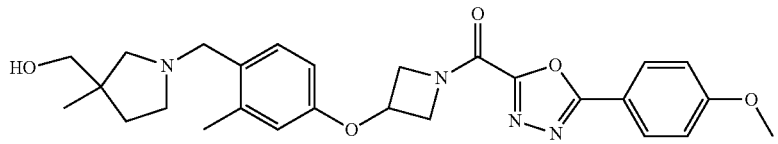 [SMILES: COc1ccc(-c2nnc(C(=O)N3CC(Oc4ccc(CN5CCC(C)(CO)C5)c(C)c4)C3)o2)cc1]

Intermediate 84A (0.097 g, 0.64 mmol) was dissolved in dichloromethane (6 mL), THF (1 mL) and TEA (0.106 mL, 0.76 mmol). Intermediate 73C (0.120 g, 0.31 mmol) was added and the mixture stirred at RT for 5 min. and then sodium triacetoxyhydroborate (0.129 g, 0.61 mmol) was added. The mixture was stirred at RT for 21 h. Aqueous NaHCO$_3$ (8%, 4 mL) was added and the mixture was filtered through a phase separator, dichloromethane (4 mL) was added and the solvent was removed by evaporation. The product was purified by preparative HPLC under basic conditions followed by lyophilisation to give (0.114 g, 76%). $^1$H NMR (400 MHz, CDCl$_3$) δ 1.01 (s, 3H), 1.56-1.71 (m, 1H), 1.93-2.21 (m, 2H), 2.22-2.39 (m, 4H), 2.77-2.92 (m, 1H), 2.94-3.09 (m, 1H), 3.25-3.39 (m, 1H), 3.41-3.62 (m, 3H), 3.89 (s, 3H), 4.25-4.39 (m, 1H), 4.54-4.8 (m, 2H), 4.99-5.18 (m, 2H), 6.47-6.66 (m, 2H), 7.02 (d, 2H), 7.08-7.19 (m, 1H), 8.10 (d, 2H), MS (APCI+) m/z 493 [M+H]+, LC Purity: 99%.

It will be appreciated by those skilled in the art that the title compound is chiral. The individual enantiomers:

(+)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone and (−)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone are obtained by chiral chromatography for example as described in Example 84.

Example 92

(3-(4-((4-Ethyl-4-(hydroxymethyl)piperidin-1-yl)methyl)phenoxy)azetidin-1-yl)(5-(4-methoxyphenyl)-1,3,4-oxadiazol-2-yl)methanone

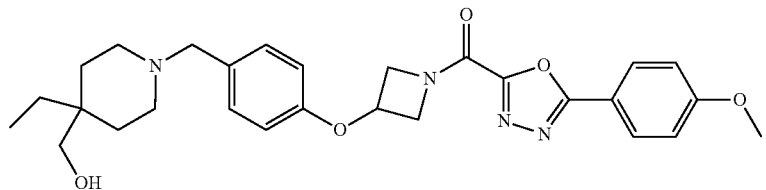 [SMILES: CCC1(CO)CCN(Cc2ccc(OC3CN(C(=O)c4nnc(-c5ccc(OC)cc5)o4)C3)cc2)CC1]

To a solution of 4-(1-(5-(4-methoxyphenyl)-1,3,4-oxadiazole-2-carbonyl)azetidin-3-yloxy)benzaldehyde (0.55 g, 1.45 mmol in DCM (30 mL) were added (4-ethylpiperidin-4-yl)methanol (0.27 g, 1.88 mmol, 1.3 equiv) and sodium triacetoxyborohydride (0.615 g, 2.90 mmol, 2 equiv). The reaction mixture was stirred at room temperature overnight and thereafter transferred to a reparatory funnel, washed with a saturated solution of $Na_2CO_3$, dried (phase separator) and concentrated under reduced pressure. The crude product was purified by automatic flash column chromatography using Biotage (eluting with EtOAc (10 CV), then EtOAc/MeOH (containing 2 M $NH_3$) 20:1) on a 50 g snap column, collecting at UV 291 nm). The pure product fractions were combined and evaporated to afford the product as a white solid. Recrystallisation from DCM/$Et_2O$ afforded 280 mg, 38% of the product as a white solid (purity >99%). $^1$H NMR (400 MHz, $CDCl_3$): δ 0.82 (t, 3H), 1.37-1.56 (m, 6H), 2.30-2.46 (m, 4H), 3.45 (2×s, 4H), 3.89 (s, 3H), 4.33 (dd, 1H), 4.64 (dd, 1H), 4.74 (dd, 1H), 5.03-5.15 (m, 2H), 6.72 (d, 2H), 7.02 (d, 2H), 7.25 (d, 2H), 8.1 (d, 2H), MS (APCI+) m/z 507 [M+H]$^+$.

The invention claimed is:
1. A compound of formula I

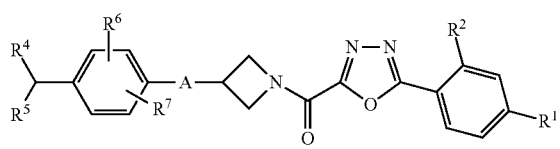

I or a pharmaceutically acceptable salt thereof in which
$R^1$ represents H, fluoro, chloro, bromo, cyano, a $C_{1-4}$alkyl group optionally substituted by one or more fluoro, a $C_{1-2}$alkoxy group optionally substituted by one or more fluoro, or a $C_{1-3}$alkylthio group optionally substituted by one or more fluoro;
$R^2$ represents H or fluoro;
$R^4$ represents a group of formula —$NR^aR^b$ in which
a) $R^a$ and $R^b$ independently represent:
  1) H
  2) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy, a $C_{1-4}$alkoxy group or fluoro
  3) a $C_{3-6}$cycloalkyl group optionally substituted by one or more of the following: hydroxy, a $C_{1-4}$alkoxy group or fluoro
  4) a $C_{1-4}$alkoxy $C_{2-4}$alkylene group in which the alkylene chain is optionally substituted by one or more $C_{1-4}$alkyl groups or
  5) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_{1-4}$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group; or
b) $R^a$ and $R^b$ together with the nitrogen atom to which they are attached represent a saturated 4 to 7 membered monocyclic heterocyclic ring optionally containing an additional oxygen, sulphur, SO or $SO_2$ provided that this additional atom or group is always separated from the nitrogen atom by at least two carbon atoms and wherein the ring is optionally substituted by one or more of the following: fluoro, hydroxy, a $C_{1-4}$alkoxy group, a $C_{1-4}$alkoxycarbonyl group, a $C_{3-6}$cycloalkyl group, or a $C_{1-4}$alkyl group optionally substituted by hydroxy or by a $C_{1-4}$alkoxy group or by one or more fluoro, provided that the substituents linked to the ring by a hetero atom are not located at a carbon atom adjacent to any ring hetero atom; or
c) $R^a$ and $R^b$ together with the nitrogen atom to which they are attached represent a saturated 4 to 7 membered monocyclic heterocyclic ring containing an additional nitrogen optionally substituted at the additional nitrogen atom by a $C_{1-4}$alkanoyl group, benzoyl, a $C_{1-4}$alkoxycarbonyl group, a $C_{1-4}$alkylsulfonyl group, carbamoyl, N—$C_{1-4}$alkylcarbamoyl, N,N-di$C_{1-4}$alkylcarbamoyl or $C_{1-4}$alkyl group;
$R^5$ represents H or a $C_{1-3}$alkyl group optionally substituted by one or more fluoro or one of the following: hydroxy or a $C_{1-4}$alkoxy group;
$R^6$ and $R^7$ independently represent H, fluoro, chloro, bromo, a $C_{1-4}$alkyl group optionally substituted by one or more fluoro, a $C_{1-4}$alkoxy group optionally substituted by one or more fluoro; provided that $R^6$ and $R^7$ are not located meta to each other; and
A represents O or S.
2. A compound of formula I as claimed in claim 1 in which A represents O.
3. A compound of formula I as claimed in claim 1 as represented by formula II

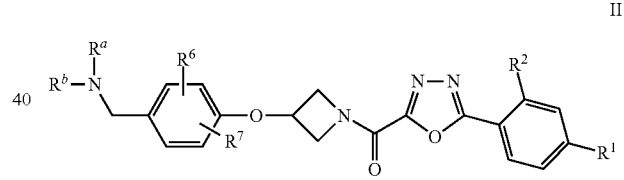

II or a pharmaceutically acceptable salt thereof in which
$R^1$ represents H, fluoro, chloro, bromo, a $C_{1-4}$alkyl group optionally substituted by one or more fluoro or a $C_{1-2}$alkoxy group optionally substituted by one or more fluoro;
$R^2$ represents H or fluoro;
$R^a$ and $R^b$ independently represent
a) $R^a$ and $R^b$ independently represent:
  1) H
  2) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy or by a $C_{1-4}$alkoxy group or by one or more fluoro
  3) a $C_{3-6}$cycloalkyl group optionally substituted by one or more of the following: hydroxy, a $C_{1-4}$alkoxy group or fluoro
  4) a $C_{1-4}$alkoxy $C_{2-4}$alkylene group in which the alkylene chain is optionally substituted by one or more $C_{1-4}$alkyl groups or
  5) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_{1-4}$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group; or b) $R^a$ and $R^b$ together with the nitrogen atom to which they are attached represent
  1) a pyrrolidino ring optionally substituted by one or more of the following: fluoro, a $C_{1-4}$alkoxy group, hydroxy, or a $C_{1-4}$alkyl group optionally substituted by hydroxy, provided that the substituents linked to the ring by a hetero atom are not located at a carbon atom adjacent to the nitrogen atom; or
  2) a morpholino ring; or
  3) a piperazino ring which is optionally substituted at the additional nitrogen atom by a $C_{1-4}$alkanoyl group; a $C_{1-4}$alkylsulfonyl group or a $C_{1-4}$alkyl group; or
  4) an azetidino ring optionally substituted by one or more of the following: fluoro, hydroxy, a $C_{1-4}$alkoxy group, a $C_{3-6}$cycloalkyl group or a $C_{1-4}$alkyl group optionally substituted by hydroxy, by a $C_{1-4}$alkoxy group or by one or more fluoro provided that the substituents linked to the ring by a hetero atom are not located at a carbon atom adjacent to any ring hetero atom; or
  5) a piperidino ring optionally substituted by one or more of the following: fluoro, hydroxy, a $C_{1-4}$alkoxy group, a $C_{3-6}$cycloalkyl group, and a $C_{1-4}$alkyl group optionally substituted by hydroxy, by a $C_{1-4}$alkoxy group or by one or more fluoro;

$R^6$ and $R^7$ independently represent H, fluoro, chloro, a $C_{1-4}$alkyl group or a $C_{1-4}$alkoxy group provided that $R^6$ and $R^7$ are not located meta to each other.

4. A compound of formula I as claimed in claim 1 as represented by formula IIA

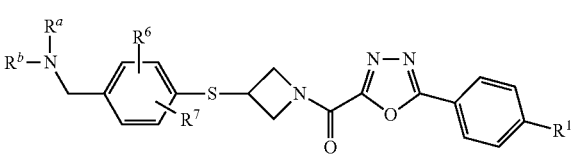

IIA or a pharmaceutically acceptable salt thereof in which $R^1$ represents H, fluoro, chloro, bromo, a $C_{1-4}$alkyl group optionally substituted by one or more fluoro or a $C_{1-2}$alkoxy group optionally substituted by one or more fluoro;

$R^a$ and $R^b$ independently represent a) H, a $C_{1-4}$alkyl group, a $C_{3-6}$cycloalkyl group, a $C_{1-4}$alkoxy $C_{2-4}$alkylene group in which the alkylene chain is optionally substituted by one or more $C_{1-4}$alkyl groups or $R^a$ and $R^b$ independently represent a group -L-$R^8$ in which L represents a bond or a $C_{1-4}$alkylene chain optionally substituted by one or more $C_{1-2}$alkyl groups and $R^8$ represents tetrahydrofuryl or tetrahydropyranyl each of which is optionally substituted by one or more of the following: hydroxy, a $C_{1-4}$alkyl group, a $C_{1-4}$alkoxy group or a $C_{1-4}$alkanoyl group; or b) $R^a$ and $R^b$ together with the nitrogen atom to which they are attached represent
  1) a pyrrolidino ring optionally substituted by one or more of the following: a $C_{1-4}$alkoxy group, hydroxy, or a $C_{1-4}$alkyl group provided that the substituents linked to the ring by a hetero atom are not located at a carbon atom adjacent to the nitrogen atom,
  2) a morpholino ring or
  3) a piperazino ring which is optionally substituted at the additional nitrogen atom by a $C_{1-4}$alkanoyl group; a $C_{1-4}$alkylsulfonyl group or a $C_{1-4}$alkyl group; or
  4) an azetidino ring which is optionally substituted by one or more of the following: hydroxy, a $C_{1-4}$alkoxy group, a $C_{3-6}$cycloalkyl group, or a $C_{1-4}$alkyl group optionally substituted by hydroxy or by a $C_{1-4}$alkoxy group provided that the substituents linked to the ring by a hetero atom are not located at a carbon atom adjacent to any ring hetero atom; or
  5) a piperidino ring optionally substituted by one or more of the following: fluoro, hydroxy, a $C_{1-4}$alkoxy group, a $C_{3-6}$cycloalkyl group, or a $C_{1-4}$alkyl group optionally substituted by hydroxy or by a $C_{1-4}$alkoxy group or by one or more fluoro;

$R^6$ and $R^7$ independently represent H, fluoro, chloro, a $C_{1-4}$alkyl group or a $C_{1-4}$alkoxy group provided that $R^6$ and $R^7$ are not located meta to each other.

5. A compound of formula I as claimed in claim 1 as represented by formula III

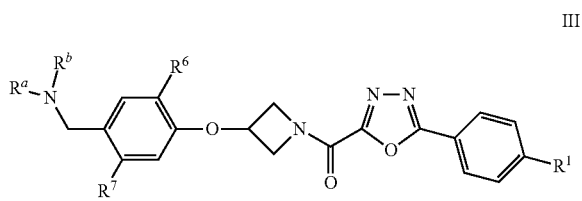

III or a pharmaceutically acceptable salt thereof
in which $R^1$ represents H or methoxy;
$R^a$ and $R^b$ independently represent H or methyl provided that at least one of $R^a$ and $R^b$ represents methyl; and
$R^6$ and $R^7$ independently represent H or methyl provided that at least one of $R^6$ and $R^7$ represents methyl.

6. A compound of formula I as claimed in claim 1 as represented by formula IIIA

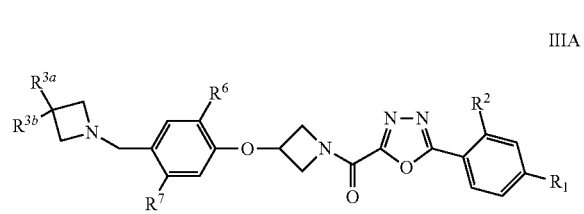

IIIA or a pharmaceutically acceptable salt thereof
in which $R^1$ represents H or methoxy;
in which $R^2$ represents H or fluoro;
$R^6$ and $R^7$ independently represent H, chloro or methyl provided that one of $R^6$ and $R^7$ represents H;
$R^{3a}$ represents H, fluoro, hydroxy or a $C_{1-4}$alkyl group optionally substituted by hydroxy or by one or more fluoro; and $R^{3b}$ represents H or a $C_{1-4}$alkyl group optionally substituted by hydroxy.

7. A compound of formula I as claimed in claim 1 as represented by formula IIIB

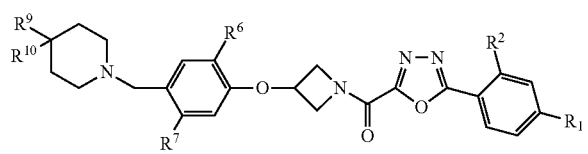

IIIB or a pharmaceutically acceptable salt thereof
in which $R^1$ represents H or methoxy;
$R^2$ represents H or fluoro;
$R^6$ and $R^7$ independently represent H or methyl provided that only one of $R^6$ and $R^7$ represents methyl;
$R^9$ represents H, fluoro, hydroxy or a $C_{1-4}$alkyl group optionally substituted by hydroxy or by one or more fluoro; and
$R^{10}$ represents H or a $C_{1-4}$alkyl group optionally substituted by hydroxy.

8. A compound of formula I as claimed in claim 1 as represented by formula IIIC

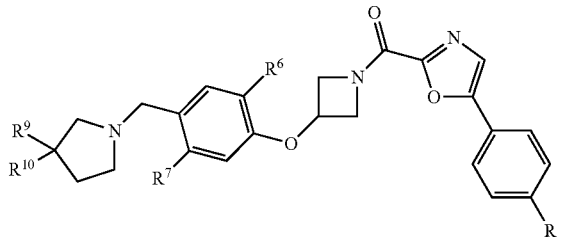

IIIC or a pharmaceutically acceptable salt thereof
in which $R^1$ represents H or methoxy;
$R^6$ and $R^7$ independently represent H or methyl provided that only one of $R^6$ and $R^7$ represents methyl;
$R^9$ represents H, fluoro, hydroxy or a $C_{1-4}$alkyl group optionally substituted by hydroxy or by one or more fluoro; and
$R^{10}$ represents H or a $C_{1-4}$alkyl group optionally substituted by hydroxy.

9. A compound according to claim 1 selected from one or more of the following compounds:
(5-(4-chlorophenyl)-1,3,4-oxadiazol-2-yl)(3-(4-(pyrrolidin-1-ylmethyl)phenoxy)azetidin-1-yl)methanone;
(5-(4-methoxyphenyl)-1,3,4-oxadiazol-2-yl)(3-(4-(pyrrolidin-1-ylmethyl)phenoxy)azetidin-1-yl)methanone;
(5-phenyl-1,3,4-oxadiazol-2-yl)(3-(4-(pyrrolidin-1-ylmethyl)phenoxy)azetidin-1-yl)methanone;
(5-(4-fluorophenyl)-1,3,4-oxadiazol-2-yl)(3-(4-(pyrrolidin-1-ylmethyl)phenoxy)azetidin-1-yl)methanone;
(3-(4-(pyrrolidin-1-ylmethyl)phenoxy)azetidin-1-yl)(5-(4-(trifluoromethyl)phenyl)-1,3,4-oxadiazol-2-yl)methanone;
(3-(4-(pyrrolidin-1-ylmethyl)phenoxy)azetidin-1-yl)(5-p-tolyl-1,3,4-oxadiazol-2-yl)methanone;
(3-(3-methoxy-4-(morpholinomethyl)phenoxy)azetidin-1-yl)(5-phenyl-1,3,4-oxadiazol-2-yl)methanone;
(3-(3-methoxy-4-(morpholinomethyl)phenoxy)azetidin-1-yl)(5-(4-methoxyphenyl)-1,3,4-oxadiazol-2-yl)methanone;
(3-(2-methyl-4-((4-methylpiperazin-1-yl)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(2-methyl-4-((4-methylpiperazin-1-yl)methyl)phenoxy)azetidin-1-yl)methanone;
(3-(2-methyl-4-((4-methylpiperazin-1-yl)methyl)phenoxy)azetidin-1-yl)(5-p-tolyl-1,3,4-oxadiazol-2-yl)methanone;
(5-(4-methoxyphenyl)-1,3,4-oxadiazol-2-yl)(3-(2-methyl-4-(morpholinomethyl)phenoxy)azetidin-1-yl)methanone;
(3-(2-methyl-4-(morpholinomethyl)phenoxy)azetidin-1-yl)(5-p-tolyl-1,3,4-oxadiazol-2-yl)methanone;
(3-(2-methyl-4-(morpholinomethyl)phenoxy)azetidin-1-yl)(5-phenyl-1,3,4-oxadiazol-2-yl)methanone;
(5-(4-chlorophenyl)-1,3,4-oxadiazol-2-yl)(3-(2-methyl-4-(morpholinomethyl)phenoxy)azetidin-1-yl)methanone;
(3-(4-((dimethylamino)methyl)-2-methylphenoxy)azetidin-1-yl)(5-phenyl-1,3,4-oxadiazol-2-yl)methanone;
(3-(4-((dimethylamino)methyl)-2-methylphenoxy)azetidin-1-yl)(5-(4-methoxyphenyl)-1,3,4-oxadiazol-2-yl)methanone;
(3-(4-((dimethylamino)methyl)-2-methylphenoxy)azetidin-1-yl)(5-p-tolyl-1,3,4-oxadiazol-2-yl)methanone;
(5-(4-chlorophenyl)-1,3,4-oxadiazol-2-yl)(3-(2-methyl-4-(pyrrolidin-1-ylmethyl)phenoxy)azetidin-1-yl)methanone;
(3-(4-((dimethylamino)methyl)-3-methylphenoxy)azetidin-1-yl)(5-(4-methoxyphenyl)-1,3,4-oxadiazol-2-yl)methanone;
(3-(4-((dimethylamino)methyl)-3-methylphenoxy)azetidin-1-yl)(5-phenyl-1,3,4-oxadiazol-2-yl)methanone;
(3-(4-((dimethylamino)methyl)-3-methylphenoxy)azetidin-1-yl)(5-p-tolyl-1,3,4-oxadiazol-2-yl)methanone;
1-(4-(4-(1-(5-phenyl-1,3,4-oxadiazole-2-carbonyl)azetidin-3-yloxy)benzyl)piperazin-1-yl)ethanone;
1-(4-(4-(1-(5-(4-methoxyphenyl)-1,3,4-oxadiazole-2-carbonyl)azetidin-3-yloxy)benzyl)piperazin-1-yl)ethanone;
1-(4-(4-(1-(5-(4-chlorophenyl)-1,3,4-oxadiazole-2-carbonyl)azetidin-3-yloxy)benzyl)piperazin-1-yl)ethanone;
(3-(4-((dimethylamino)methyl)-3-fluorophenoxy)azetidin-1-yl)(5-phenyl-1,3,4-oxadiazol-2-yl)methanone;
(3-(4-((dimethylamino)methyl)-3-fluorophenoxy)azetidin-1-yl)(5-(4-methoxyphenyl)-1,3,4-oxadiazol-2-yl)methanone;
(3-(4-((dimethylamino)methyl)-3-fluorophenoxy)azetidin-1-yl)(5-p-tolyl-1,3,4-oxadiazol-2-yl)methanone;
(3-(3-fluoro-4-((4-methylpiperazin-1-yl)methyl)phenoxy)azetidin-1-yl)(5-phenyl-1,3,4-oxadiazol-2-yl)methanone;
(3-(3-fluoro-4-((4-methylpiperazin-1-yl)methyl)phenoxy)azetidin-1-yl)(5-(4-methoxyphenyl)-1,3,4-oxadiazol-2-yl)methanone;
(3-(3-fluoro-4-(pyrrolidin-1-ylmethyl)phenoxy)azetidin-1-yl)(5-phenyl-1,3,4-oxadiazol-2-yl)methanone;
(3-(3-fluoro-4-(pyrrolidin-1-ylmethyl)phenoxy)azetidin-1-yl)(5-(4-methoxyphenyl)-1,3,4-oxadiazol-2-yl)methanone;
(3-(4-((dimethylamino)methyl)phenoxy)azetidin-1-yl)(5-phenyl-1,3,4-oxadiazol-2-yl)methanone;

(3-(4-((dimethylamino)methyl)phenoxy)azetidin-1-yl)(5-(4-(methylthio)phenyl)-1,3,4-oxadiazol-2-yl)methanone;
(3-(4-((dimethylamino)methyl)phenoxy)azetidin-1-yl)(5-(4-(trifluoromethyl)phenyl)-1,3,4-oxadiazol-2-yl)methanone;
(5-(4-chlorophenyl)-1,3,4-oxadiazol-2-yl)(3-(4-((dimethylamino)methyl)phenoxy)azetidin-1-yl)methanone;
(5-(4-(difluoromethoxy)phenyl)-1,3,4-oxadiazol-2-yl)(3-(4-((dimethylamino)methyl)phenoxy)azetidin-1-yl)methanone;
(3-(4-((dimethylamino)methyl)phenoxy)azetidin-1-yl)(5-(4-methoxyphenyl)-1,3,4-oxadiazol-2-yl)methanone;
(3-(4-((dimethylamino)methyl)-2,3-difluorophenoxy)azetidin-1-yl)(5-phenyl-1,3,4-oxadiazol-2-yl)methanone;
(3-(4-((dimethylamino)methyl)-2,3-difluorophenoxy)azetidin-1-yl)(5-(4-methoxyphenyl)-1,3,4-oxadiazol-2-yl)methanone;
(3-(4-(azetidin-1-ylmethyl)phenoxy)azetidin-1-yl)(5-(4-methoxyphenyl)-1,3,4-oxadiazol-2-yl)methanone;
(3-(4-(azetidin-1-ylmethyl)phenoxy)azetidin-1-yl)(5-phenyl-1,3,4-oxadiazol-2-yl)methanone;
(5-(4-(difluoromethoxy)phenyl)-1,3,4-oxadiazol-2-yl)(3-(4-((dimethylamino)methyl)-3-methylphenoxy)azetidin-1-yl)methanone;
(5-(4-chlorophenyl)-1,3,4-oxadiazol-2-yl)(3-(4-((dimethylamino)methyl)-3-methylphenoxy)azetidin-1-yl)methanone;
(5-phenyl-1,3,4-oxadiazol-2-yl)(3-(4-(pyrrolidin-1-ylmethyl)-3-(trifluoromethyl)phenoxy)azetidin-1-yl)methanone;
(5-(4-methoxyphenyl)-1,3,4-oxadiazol-2-yl)(3-(4-(pyrrolidin-1-ylmethyl)-3-(trifluoromethyl)phenoxy)azetidin-1-yl)methanone;
(3-(3-chloro-4-((dimethylamino)methyl)phenoxy)azetidin-1-yl)(5-(4-methoxyphenyl)-1,3,4-oxadiazol-2-yl)methanone;
(3-(3-chloro-4-((dimethylamino)methyl)phenoxy)azetidin-1-yl)(5-phenyl-1,3,4-oxadiazol-2-yl)methanone;
(3-(3-chloro-4-((4-methylpiperazin-1-yl)methyl)phenoxy)azetidin-1-yl)(5-(4-methoxyphenyl)-1,3,4-oxadiazol-2-yl)methanone;
(3-(3-chloro-4-((4-methylpiperazin-1-yl)methyl)phenoxy)azetidin-1-yl)(5-phenyl-1,3,4-oxadiazol-2-yl)methanone;
(5-(4-(difluoromethoxy)phenyl)-1,3,4-oxadiazol-2-yl)(3-(4-((dimethylamino)methyl)-3-fluorophenoxy)azetidin-1-yl)methanone;
(3-(3-methoxy-2-methyl-4-(pyrrolidin-1-ylmethyl)phenoxy)azetidin-1-yl)(5-(4-methoxyphenyl)-1,3,4-oxadiazol-2-yl)methanone;
(3-(3-methyl-4-((methylamino)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(2-methyl-4-((methylamino)methyl)phenoxy)azetidin-1-yl)methanone;
(3-(4-((3-methoxyazetidin-1-yl)methyl)phenoxy)azetidin-1-yl)(5-(4-methoxyphenyl)-1,3,4-oxadiazol-2-yl)methanone;
(3-(4-((3-cyclopropyl-3-hydroxyazetidin-1-yl)methyl)phenoxy)azetidin-1-yl)(5-(4-methoxyphenyl)-1,3,4-oxadiazol-2-yl)methanone;
(3-(2-chloro-4-((3-methoxyazetidin-1-yl)methyl)phenoxy)azetidin-1-yl)(5-phenyl-1,3,4-oxadiazol-2-yl)methanone;
(3-(2-chloro-4-((3-hydroxyazetidin-1-yl)methyl)phenoxy)azetidin-1-yl)(5-phenyl-1,3,4-oxadiazol-2-yl)methanone;
(5-(4-methoxyphenyl)-1,3,4-oxadiazol-2-yl)(3-(4-(pyrrolidin-1-ylmethyl)phenylthio)azetidin-1-yl)methanone;
(3-(4-((dimethylamino)methyl)phenylthio)azetidin-1-yl)(5-phenyl-1,3,4-oxadiazol-2-yl)methanone;
(3-(4-(((2-methoxyethyl)(methyl)amino)methyl)phenylthio)azetidin-1-yl)(5-phenyl-1,3,4-oxadiazol-2-yl)methanone;
(3-(4-((3-methoxyazetidin-1-yl)methyl)phenylthio)azetidin-1-yl)(5-phenyl-1,3,4-oxadiazol-2-yl)methanone;
(3-(4-((methylamino)methyl)phenylthio)azetidin-1-yl)(5-phenyl-1,3,4-oxadiazol-2-yl)methanone;
(3-(4-((methyl(tetrahydro-2H-pyran-4-yl)amino)methyl)phenylthio)azetidin-1-yl)(5-phenyl-1,3,4-oxadiazol-2-yl)methanone;
(3-(4-((methyl((tetrahydrofuran-3-yl)methyl)amino)methyl)phenylthio)azetidin-1-yl)(5-phenyl-1,3,4-oxadiazol-2-yl)methanone;
(3-(4-((cyclopropylamino)methyl)phenylthio)azetidin-1-yl)(5-phenyl-1,3,4-oxadiazol-2-yl)methanone;
(3-(4-((3-(hydroxymethyl)azetidin-1-yl)methyl)phenylthio)azetidin-1-yl)(5-phenyl-1,3,4-oxadiazol-2-yl)methanone;
(3-(4-((3-(difluoromethyl)azetidin-1-yl)methyl)phenoxy)azetidin-1-yl)(5-phenyl-1,3,4-oxadiazol-2-yl)methanone;
(3-(4-((4-(hydroxymethyl)-4-methylpiperidin-1-yl)methyl)-3-methylphenoxy)azetidin-1-yl)(5-phenyl-1,3,4-oxadiazol-2-yl)methanone;
(3-(4-((3-ethyl-3-hydroxyazetidin-1-yl)methyl)phenoxy)azetidin-1-yl)(5-(4-methoxyphenyl)-1,3,4-oxadiazol-2-yl)methanone;
(3-(4-((3-ethyl-3-hydroxyazetidin-1-yl)methyl)phenoxy)azetidin-1-yl)(5-phenyl-1,3,4-oxadiazol-2-yl)methanone;
(3-(4-((3-ethyl-3-hydroxyazetidin-1-yl)methyl)-2-methylphenoxy)azetidin-1-yl)(5-(4-methoxyphenyl)-1,3,4-oxadiazol-2-yl)methanone;
(3-(4-((3-ethyl-3-hydroxyazetidin-1-yl)methyl)-3-methylphenoxy)azetidin-1-yl)(5-(4-methoxyphenyl)-1,3,4-oxadiazol-2-yl)methanone;
(3-(4-((3-ethyl-3-hydroxyazetidin-1-yl)methyl)-2-methylphenoxy)azetidin-1-yl)(5-phenyl-1,3,4-oxadiazol-2-yl)methanone;
(3-(4-((3-ethyl-3-hydroxyazetidin-1-yl)methyl)-3-methylphenoxy)azetidin-1-yl)(5-phenyl-1,3,4-oxadiazol-2-yl)methanone;
(3-(4-((3-hydroxy-3-methylazetidin-1-yl)methyl)phenoxy)azetidin-1-yl)(5-(4-methoxyphenyl)-1,3,4-oxadiazol-2-yl)methanone;
(3-(4-((3-hydroxy-3-methylazetidin-1-yl)methyl)phenoxy)azetidin-1-yl)(5-phenyl-1,3,4-oxadiazol-2-yl)methanone;
(3-(2-chloro-4-((3-hydroxy-3-methylazetidin-1-yl)methyl)phenoxy)azetidin-1-yl)(5-phenyl-1,3,4-oxadiazol-2-yl)methanone;
(3-(2-chloro-4-((3-hydroxy-3-methylazetidin-1-yl)methyl)phenoxy)azetidin-1-yl)(5-(4-methoxyphenyl)-1,3,4-oxadiazol-2-yl)methanone;
(3-(4-((3-hydroxy-3-methylazetidin-1-yl)methyl)-3-methylphenoxy)azetidin-1-yl)(5-(4-methoxyphenyl)-1,3,4-oxadiazol-2-yl)methanone;
(3-(4-((4-fluoro-4-(hydroxymethyl)piperidin-1-yl)methyl)phenoxy)azetidin-1-yl)(5-(4-methoxyphenyl)-1,3,4-oxadiazol-2-yl)methanone;

(3-(4-((4-(hydroxymethyl)-4-methylpiperidin-1-yl)methyl)-3-methylphenoxy)azetidin-1-yl)(5-(4-methoxyphenyl)-1,3,4-oxadiazol-2-yl)methanone;
(3-(4-((4-(hydroxymethyl)-4-methylpiperidin-1-yl)methyl)phenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(+)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(−)(3-(4-((3-(hydroxymethyl)-3-methylpyrrolidin-1-yl)methyl)phenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)phenoxy)azetidin-1-yl)(5-phenyl-1,3,4-oxadiazol-2-yl)methanone;
(+)(3-(4-((3-(hydroxymethyl)-3-methylpyrrolidin-1-yl)methyl)phenoxy)azetidin-1-yl)(5-phenyl-1,3,4-oxadiazol-2-yl)methanone;
(−)(3-(4-((3-(hydroxymethyl)-3-methylpyrrolidin-1-yl)methyl)phenoxy)azetidin-1-yl)(5-phenyl-1,3,4-oxadiazol-2-yl)methanone;
(3-(4-((4-hydroxyazepan-1-yl)methyl)phenoxy)azetidin-1-yl)(5-(4-methoxyphenyl)-1,3,4-oxadiazol-2-yl)methanone;
(+)(3-(4-((4-hydroxyazepan-1-yl)methyl)phenoxy)azetidin-1-yl)(5-(4-methoxyphenyl)-1,3,4-oxadiazol-2-yl)methanone;
(−)(3-(4-((4-hydroxyazepan-1-yl)methyl)phenoxy)azetidin-1-yl)(5-(4-methoxyphenyl)-1,3,4-oxadiazol-2-yl)methanone;
(3-(4-((4-hydroxy-4-methylazepan-1-yl)methyl)phenoxy)azetidin-1-yl)(5-phenyl-1,3,4-oxadiazol-2-yl)methanone;
(+)(3-(4-((4-hydroxy-4-methylazepan-1-yl)methyl)phenoxy)azetidin-1-yl)(5-phenyl-1,3,4-oxadiazol-2-yl)methanone;
(−)(3-(4-((4-hydroxy-4-methylazepan-1-yl)methyl)phenoxy)azetidin-1-yl)(5-phenyl-1,3,4-oxadiazol-2-yl)methanone;
(3-(4-((4-hydroxy-4-methylazepan-1-yl)methyl)phenoxy)azetidin-1-yl)(5-(4-methoxyphenyl)-1,3,4-oxadiazol-2-yl)methanone;
(+)(3-(4-((4-hydroxy-4-methylazepan-1-yl)methyl)phenoxy)azetidin-1-yl)(5-(4-methoxyphenyl)-1,3,4-oxadiazol-2-yl)methanone;
(−)(3-(4-((4-hydroxy-4-methylazepan-1-yl)methyl)phenoxy)azetidin-1-yl)(5-(4-methoxyphenyl)-1,3,4-oxadiazol-2-yl)methanone;
(3-(4-((4-(hydroxymethyl)piperidin-1-yl)methyl)phenoxy)azetidin-1-yl)(5-(4-methoxyphenyl)-1,3,4-oxadiazol-2-yl)methanone;
3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(+)3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(−)3-(4-((3-(hydroxymethyl)-3-methylpyrrolidin-1-yl)methyl)-2-methylphenoxy)azetidin-1-yl)(5-(4-methoxyphenyl)-1,3,4-oxadiazol-2-yl)methanone;
(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone;
(+)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone;
(−)(3-(4-((3-(hydroxymethyl)-3-methylpyrrolidin-1-yl)methyl)-3-methylphenoxy)azetidin-1-yl)(5-(4-methoxyphenyl)-1,3,4-oxadiazol-2-yl)methanone; and
(3-(4-((4-ethyl-4-(hydroxymethyl)piperidin-1-yl)methyl)phenoxy)azetidin-1-yl)(5-(4-methoxyphenyl)-1,3,4-oxadiazol-2-yl)methanone;
or a pharmaceutically acceptable salt thereof.

10. A pharmaceutical composition comprising at least one compound according to claim 1 and a pharmaceutically acceptable carrier and/or diluent.

11. A process for the preparation of a compound of formula I according to claim 1 comprising
 a) reacting a compound of formula IV

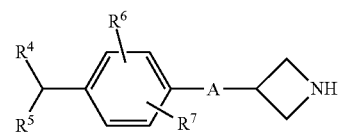

in which $R^4$, $R^5$, $R^6$, $R^7$ and A are as previously defined with a compound of formula V

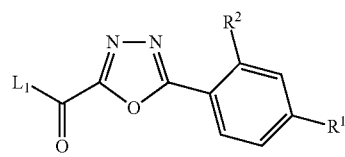

in which $R^1$ and $R^2$ are as previously defined and $L_1$ is $C_{1-4}$alkoxy; or b) reacting a compound of formula VI

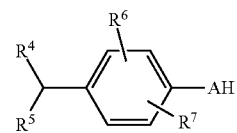

in which $R^4$, $R^5$, $R^6$, $R^7$ and A are as previously defined with a compound of formula VII

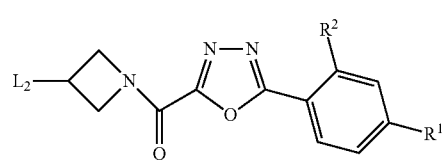

in which $R^1$ and $R^2$ are as previously defined and $L_2$ is mesyloxy or tosyloxy in the presence of a base optionally in the presence of a solvent at a temperature in the range of 0 to 150° C.; or c) reacting a compound of formula VIII

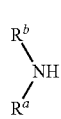

in which $R^a$ and $R^b$ are as previously defined with a compound of formula IX

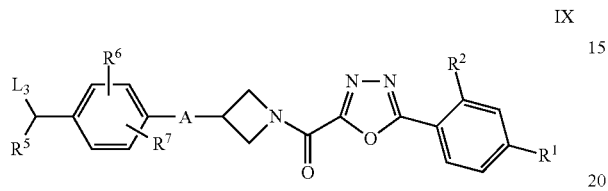

in which $R^1$, $R^2$, $R^5$, $R^6$, $R^7$ and A are as previously defined and $L_3$ is halo optionally in the presence of a solvent and optionally in the presence of a base at a temperature in the range of 0 to 150° C.; or d) reacting a compound of formula VIII in which $R^a$ and $R^b$ are as previously defined with a compound of formula IX in which $R^1$, $R^2$, $R^5$, $R^6$, $R^7$ and A are as previously defined and $L_3$ represents an oxo group in the presence of a reducing agent in an appropriate solvent.

12. A process as claimed in claim 11 wherein $L_3$ in step c) is chloro or bromo.

* * * * *